(12) United States Patent
Liu

(10) Patent No.: US 11,633,454 B2
(45) Date of Patent: Apr. 25, 2023

(54) COMPOSITIONS AND METHODS FOR TREATING METABOLIC DISEASES

(71) Applicant: SHANGHAI HEP PHARMACEUTICAL CO., LTD., Shanghai (CN)

(72) Inventor: Hongli Liu, Shanghai (CN)

(73) Assignee: SHANGHAI HEP PHARMACEUTICAL CO., LTD., Shanghai (CN)

( * ) Notice: Subject to any disclaimer, the term of this patent is extended or adjusted under 35 U.S.C. 154(b) by 365 days.

(21) Appl. No.: 16/305,790

(22) PCT Filed: May 31, 2017

(86) PCT No.: PCT/CN2017/086558
§ 371 (c)(1),
(2) Date: Nov. 29, 2018

(87) PCT Pub. No.: WO2017/206898
PCT Pub. Date: Dec. 7, 2017

(65) Prior Publication Data
US 2020/0323951 A1  Oct. 15, 2020

(30) Foreign Application Priority Data

May 30, 2016  (CN) .......................... 201610370442.4

(51) Int. Cl.
| | | |
|---|---|---|
| A61K 38/16 | (2006.01) | |
| A61P 3/06 | (2006.01) | |
| A61P 3/10 | (2006.01) | |
| A61K 9/00 | (2006.01) | |
| A61K 45/06 | (2006.01) | |

(52) U.S. Cl.
CPC .............. *A61K 38/162* (2013.01); *A61P 3/06* (2018.01); *A61P 3/10* (2018.01); *A61K 9/0021* (2013.01); *A61K 45/06* (2013.01)

(58) Field of Classification Search
None
See application file for complete search history.

(56) References Cited

FOREIGN PATENT DOCUMENTS

| | | | |
|---|---|---|---|
| CN | 104130316 A | | 11/2014 |
| EP | 3 181 146 A1 | | 6/2017 |
| EP | 15200494.1 | † | 6/2017 |
| EP | 15200568.2 | † | 6/2017 |
| EP | 3 189 850 A1 | | 7/2017 |
| WO | 2014/072524 A1 | † | 5/2014 |
| WO | WO 2014/072524 A1 | | 5/2014 |
| WO | WO2014/105939 A1 | | 7/2014 |
| WO | WO 2016/055534 A2 | | 4/2016 |

OTHER PUBLICATIONS

Zheng, J., et al. 2015 Front Med 9(2): 173-186. (Year: 2015).*
Ballantyne et al., "Effects of Cyclosporine Therapy on Plasma Lipoprotein Levels," JAMA, 262(1):53-56 (1989), 4 pages.
Bauer et al, "Polypharmacy in people with Type 1 and Type 2 diabetes is justified by current guidelines—a comprehensive assessment of drug prescriptions in patients needing inpatient treatment for diabetes-associated problems," Diabetic Medicine, 31:1078-85 (2014), 8 pages.
Beaudoin et al., "Caffeine ingestion impairs insulin sensitivity in a dose-dependent manner in both men and women," Appl. Physiol. Nutr. Metab. 38(2):140-47 (2013), 8 pages.
Boden et al., "Hypolipidemic effect of type Ia antiarrhythmic agents in postinfarction patients," Circulation, 85(6):2039-44 (1992), 7 pages.
Dresner et al., "Effects of Cyclosporine on Glucose Metabolism," Surgery, 106(2):163-69 (1989), 8 pages.
Garcia-Perez et al, "Adherence to therapies in patients with type 2 diabetes," Diabetes Therapy, 4:175-94 (2013), 20 pages.
Gripon et al., "Efficient Inhibition of Hepatitis B Virus Infection by Acylated Peptides Derived from the Large Viral Surface Protein ," J. Virol. 79(3):1613-22 (2005), 10 pages.
Kim et al, "Modulation by Drugs of Human Hepatic Sodium-Dependent Bile Acid Transporter (Sodium Taurocholate Cotransporting Polypeptide) Activity," J. Pharmacol. Exp. Ther. 291(3): 1204-09 (1999), 6 pages.
Liu, et al., "GenBank Accession No. EU554535.1, Hepatitis B virus isolate S472-20, complete genome," NCBI GenBank, Apr. 8, 2008, 3 pages.
Oehler, et al., "Binding of Hepatitis B Virus to Its Cellular Receptor Alters the Expression Profile of Genes of Bile Acid Metabolism," Hepatology, vol. 60, No. 5, Nov. 2014, 21 pages.
PCT International Search Report dated Aug. 22, 2017, issued in corresponding International Application No. PCT/CN2017/086558, 7 pages.
Phillips et al., "Hypoglycaemia and antimalarial drugs: quinidine and release of insulin," Br. Med. J. 292:1319-21 (1986), 3 pages.
Slijepcevic, et al., "Impaired Uptake of Conjugated Bile Acids and Hepatitis B Virus Pres1-Binding in Na+-Taurocholate Cotransporting Polypeptide Knockout Mice," Hepatology, vol. 62, No. 1, Jul. 31, 2015, 13 pages.
Thelle et al., "The TromsØ Heart Study—Does Coffee Raise Serum Cholesterol?," N. Engl. J. Med. 308(24):1454-57 (1983), 4 pages.
Tian, et al., "Recent advances in the study of a receptor for HBV: The sodium-taurocholate cotransporting polypeptide (NTCP)," Journal of Pathogen Biology, vol. 10, No. 7, Jul. 31, 2015, 4 pages.
Vaz et al., "Sodium taurocholate cotransporting polypeptide (SLC10A1) deficiency: Conjugated hypercholanemia without a clear clinical phenotype," Hepatology, 61(1):260-267 (2015), 8 pages.

(Continued)

*Primary Examiner* — Marsha Tsay
(74) *Attorney, Agent, or Firm* — Finnegan, Henderson, Farabow, Garrett & Dunner, LLP

(57) ABSTRACT

The disclosure provides compositions and methods of treating a metabolic disease, such as, e.g., diabetes and hyperlipidemia, in a subject, by administering to the subject a therapeutically effective amount of a polypeptide derived from hepatitis B virus or a pharmaceutical composition comprising the polypeptide.

19 Claims, 23 Drawing Sheets

Specification includes a Sequence Listing.

(56) References Cited

OTHER PUBLICATIONS

Watashi et al, "Cyclosporin A and its analogs inhibit hepatitis B virus entry into cultured hepatocytes through targeting a membrane transporter, sodium taurocholate cotransporting polypeptide (NTCP)," Hepatology, 59:1726-37 (2014), 12 pages.

Wei et al., "Development of the diagnostic immunoassay to detect anti-PreS1(21-47aa) antibody—a marker suggesting the health improvement of hepatitis B patients," Clinica. Chimica. Acta. 317:159-69 (2002), 11 pages.

Yan et al., "Sodium taurocholate cotransporting polypeptide is a functional receptor for human hepatitis B and D virus," eLife, 1:e00049.001 (2012), 28 pages.

Yan, et al., "Viral Entry of Hepatitis B and D Viruses and Bile Salts Transportation Share Common Molecular Determinants on Sodium Taurocholate Cotransporting Polypeptide," Journal of Virology, vol. 88, No. 6, Jan. 3, 2014, 21 pages.

Dong, et al, "Structure-Activity Relationship for FDA Approved Drugs As Inhibitors of the Human Sodium Taurocholate Cotransporting Polypeptide (NTCP)," Molecular Pharmaceutics, vol. 10, No. 3, Feb. 12, 2013, pp. 1008-1019.

Donkers, et al., "26 Inhibitors of the sodium taurocholate co-transporting poly- peptide (NTCP) to study improved metabolism by prolonged bile acid signaling," XXIII International Bile Acid Meeting Bile Acids as Signal Integrators and Metabolic Modulators; Oct. 8-9, 2014, Freiburg, Germany, vol. 194, Jan. 1, 2014 (4 pages).

Geier, Hepatitis B Virus: The "Metabolovirus" highjacks Cholesterol and Bile acid Metabolism, Hepatology, vol. 60, No. 5, Jul. 31, 2014, pp. 1458-1460.

Savvidaki, et al., "Ezetimibe is effective in the treatment of persistent hyperlipidemia of renal allograft recipients," Clinical Nephrology, vol. 75, No. 02, Feb. 1, 2011, pp. 107-112.

The Extended European Search Report issued by European Patent Office in corresponding with the application No. 17805843.4, dated Jan. 29, 2020. (15 pages).

\* cited by examiner
† cited by third party

A.

B.

A.
B.

BLANK-L02
NTCP-L02

FITC-Cmyr-47  FITC-Control Peptide

A.

B.

C.

D.

E.

F.

```
                       SEQUENCE LISTING

<160> NUMBER OF SEQ ID NOS: 49

<210> SEQ ID NO 1
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 1

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly Ala
        35                  40                  45

Gly Ala Phe Gly Pro Gly Phe Thr Pro Pro His Gly
    50                  55                  60

<210> SEQ ID NO 2
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
```

<223> OTHER INFORMATION: C-term NH2

<400> SEQUENCE: 2

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly Ala
        35                  40                  45

Gly Ala Phe Gly Pro Gly Phe
    50                  55

<210> SEQ ID NO 3
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 3

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
        35                  40                  45

<210> SEQ ID NO 4
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 4

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp
        35                  40

<210> SEQ ID NO 5
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 5

-continued

```
Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro
        35

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 6

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp
            20                  25                  30

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myr
<220> FEATURE:
<223> OTHER INFORMATION: C-term NH2

<400> SEQUENCE: 7

Gly Thr Asn Leu Ser Val Pro Asn Pro Leu Gly Phe Phe Pro Asp His
1               5                   10                  15

Gln Leu Asp Pro Ala Phe Gly Ala Asn
            20                  25

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myr
<220> FEATURE:
<223> OTHER INFORMATION: C-term NH2

<400> SEQUENCE: 8

Gly Thr Asn Leu Ser Val Pro Asn Pro Leu Gly Phe Phe Pro Asp His
1               5                   10                  15

Gln Leu Asp Pro
            20

<210> SEQ ID NO 9
<211> LENGTH: 58
<212> TYPE: PRT
<213> ORGANISM: Artificial Sequence
<220> FEATURE:
<223> OTHER INFORMATION: Description of Artificial Sequence: Synthetic
```

```
     polypeptide
<220> FEATURE:
<223> OTHER INFORMATION: N-term Myr
<220> FEATURE:
<223> OTHER INFORMATION: C-term NH2

<400> SEQUENCE: 9

Gly Gly Trp Ser Ser Lys Pro Arg Gln Gly Met Gly Thr Asn Leu Ser
1               5                   10                  15

Val Pro Asn Pro Leu Gly Phe Phe Pro Asp His Gln Leu Asp Pro Ala
            20                  25                  30

Phe Gly Ala Asn Ser Asn Asn Pro Asp Trp Asp Phe Asn Pro Asn Lys
        35                  40                  45

Asp His Trp Pro Glu Ala Asn Gln Val Gly
    50                  55

<210> SEQ ID NO 10
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 10

Gly Leu Ser Trp Thr Val Pro Leu Glu Trp Gly Thr Asn Leu Ser Val
1               5                   10                  15

Pro Asn Pro Leu Gly Phe Phe Pro Asp His Gln Leu Asp Pro Ala Phe
            20                  25                  30

Gly Ala Asn Ser Asn Asn Pro Asp Trp Asp Phe Asn Pro Asn Lys Asp
        35                  40                  45

His Trp Pro Glu Ala Asn Gln Val Gly
    50                  55

<210> SEQ ID NO 11
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Plam
<220> FEATURE:
<223> OTHER INFORMATION: C-term NH2

<400> SEQUENCE: 11

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
        35                  40                  45

<210> SEQ ID NO 12
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: N-term Stearoyl
<220> FEATURE:
<223> OTHER INFORMATION: C-term NH2

<400> SEQUENCE: 12

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
        35                  40                  45

<210> SEQ ID NO 13
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Chol
<220> FEATURE:
<223> OTHER INFORMATION: C-term NH2

<400> SEQUENCE: 13

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
        35                  40                  45

<210> SEQ ID NO 14
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 14

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Val Lys Asp Asp Trp Pro Ala Ala Asn Gln Val Gly
        35                  40                  45

<210> SEQ ID NO 15
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 15
```

```
Gly Thr Asn Leu Ser Val Pro Asn Pro Leu Gly Phe Phe Pro Asp His
1               5                   10                  15

Gln Leu Asp Pro Ala Phe Lys Ala Asn Ser Glu Asn Pro Asp Trp Asp
            20                  25                  30

Leu Asn Pro Asn Lys Asp Asn Trp Pro Asp Ala Asn Lys Val Gly
        35                  40                  45
```

<210> SEQ ID NO 16
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 16

```
Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45
```

<210> SEQ ID NO 17
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 17

```
Gly Lys Asn Ile Ser Thr Thr Asn Pro Leu Gly Phe Phe Pro Asp His
1               5                   10                  15

Gln Leu Asp Pro Ala Phe Arg Ala Asn Thr Arg Asn Pro Asp Trp Asp
            20                  25                  30

His Asn Pro Asn Lys Asp His Trp Thr Glu Ala Asn Lys Val Gly
        35                  40                  45
```

<210> SEQ ID NO 18
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 18

```
Gly Gln Asn Leu Ser Val Pro Asn Pro Leu Gly Phe Phe Pro Asp His
1               5                   10                  15

Gln Leu Asp Pro Leu Phe Arg Ala Asn Ser Ser Pro Asp Trp Asp
            20                  25                  30

Phe Asn Thr Asn Lys Asp Ser Trp Pro Met Ala Asn Lys Val Gly
        35                  40                  45
```

```
<210> SEQ ID NO 19
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 19

Gly Lys Asn Leu Ser Ala Ser Asn Pro Leu Gly Phe Leu Pro Asp His
1               5                   10                  15

Gln Leu Asp Pro Ala Phe Arg Ala Asn Thr Asn Asn Pro Asp Trp Asp
            20                  25                  30

Phe Asn Pro Lys Lys Asp Pro Trp Pro Glu Ala Asn Lys Val Gly
        35                  40                  45

<210> SEQ ID NO 20
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Myr
<220> FEATURE:
<223> OTHER INFORMATION: C-term NH2

<400> SEQUENCE: 20

Gly Gln Asn Leu Ser Val Pro Asn Pro Leu Gly Phe Phe Pro Asp His
1               5                   10                  15

Gln Leu Asp Pro Leu Phe Arg Ala Asn Ser Ser Ser Pro Asp Trp Asp
            20                  25                  30

Phe Asn Thr Asn Lys Asp Asn Trp Pro Met Ala Asn Lys Val Gly
        35                  40                  45

<210> SEQ ID NO 21
<211> LENGTH: 60
<212> TYPE: PRT
<213> ORGANISM: Hepatitis B virus

<400> SEQUENCE: 21

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly Ala
        35                  40                  45

Gly Ala Phe Gly Pro Gly Phe Thr Pro Pro His Gly
    50                  55                  60

<210> SEQ ID NO 22
<211> LENGTH: 55
<212> TYPE: PRT
<213> ORGANISM: Hepatitis B virus

<400> SEQUENCE: 22

Gly Thr Asn Leu Ser Val Pro Asn Pro Leu Gly Phe Phe Pro Asp His
```

```
                1               5                  10                 15
            Gln Leu Asp Pro Ala Phe Gly Ala Asn Ser Asn Asn Pro Asp Trp Asp
                            20                  25                  30

Phe Asn Pro Asn Lys Asp His Trp Pro Glu Ala Asn Gln Val Gly Ala
                        35                  40                  45

Gly Ala Phe Gly Pro Gly Phe
                        50                  55

<210> SEQ ID NO 23
<211> LENGTH: 47
<212> TYPE: PRT
<213> ORGANISM: Hepatitis B virus

<400> SEQUENCE: 23

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
        35                  40                  45

<210> SEQ ID NO 24
<211> LENGTH: 40
<212> TYPE: PRT
<213> ORGANISM: Hepatitis B virus

<400> SEQUENCE: 24

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp
        35                  40

<210> SEQ ID NO 25
<211> LENGTH: 35
<212> TYPE: PRT
<213> ORGANISM: Hepatitis B virus

<400> SEQUENCE: 25

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro
        35

<210> SEQ ID NO 26
<211> LENGTH: 30
<212> TYPE: PRT
<213> ORGANISM: Hepatitis B virus

<400> SEQUENCE: 26

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp
            20                  25                  30

<210> SEQ ID NO 27
<211> LENGTH: 25
```

```
<212> TYPE: PRT
<213> ORGANISM: Hepatitis B virus

<400> SEQUENCE: 27

Gly Thr Asn Leu Ser Val Pro Asn Pro Leu Gly Phe Phe Pro Asp His
1               5                   10                  15

Gln Leu Asp Pro Ala Phe Gly Ala Asn
            20                  25

<210> SEQ ID NO 28
<211> LENGTH: 20
<212> TYPE: PRT
<213> ORGANISM: Hepatitis B virus

<400> SEQUENCE: 28

Gly Thr Asn Leu Ser Val Pro Asn Pro Leu Gly Phe Phe Pro Asp His
1               5                   10                  15

Gln Leu Asp Pro
            20

<210> SEQ ID NO 29
<211> LENGTH: 58
<212> TYPE: PRT
<213> ORGANISM: Hepatitis B virus

<400> SEQUENCE: 29

Gly Gly Trp Ser Ser Lys Pro Arg Gln Gly Met Gly Thr Asn Leu Ser
1               5                   10                  15

Val Pro Asn Pro Leu Gly Phe Phe Pro Asp His Gln Leu Asp Pro Ala
            20                  25                  30

Phe Gly Ala Asn Ser Asn Asn Pro Asp Trp Asp Phe Asn Pro Asn Lys
        35                  40                  45

Asp His Trp Pro Glu Ala Asn Gln Val Gly
    50                  55

<210> SEQ ID NO 30
<211> LENGTH: 57
<212> TYPE: PRT
<213> ORGANISM: Hepatitis B virus

<400> SEQUENCE: 30

Gly Leu Ser Trp Thr Val Pro Leu Glu Trp Gly Thr Asn Leu Ser Val
1               5                   10                  15

Pro Asn Pro Leu Gly Phe Phe Pro Asp His Gln Leu Asp Pro Ala Phe
            20                  25                  30

Gly Ala Asn Ser Asn Asn Pro Asp Trp Asp Phe Asn Pro Asn Lys Asp
        35                  40                  45

His Trp Pro Glu Ala Asn Gln Val Gly
    50                  55

<210> SEQ ID NO 31
<211> LENGTH: 47
<212> TYPE: PRT
<213> ORGANISM: Hepatitis B virus

<400> SEQUENCE: 31

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30
```

Phe Asn Pro Asn Lys Asp His Trp Pro Glu Ala Asn Gln Val Gly
            35                  40                  45

<210> SEQ ID NO 32
<211> LENGTH: 47
<212> TYPE: PRT
<213> ORGANISM: Hepatitis B virus

<400> SEQUENCE: 32

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
            35                  40                  45

<210> SEQ ID NO 33
<211> LENGTH: 47
<212> TYPE: PRT
<213> ORGANISM: Hepatitis B virus

<400> SEQUENCE: 33

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
            35                  40                  45

<210> SEQ ID NO 34
<211> LENGTH: 47
<212> TYPE: PRT
<213> ORGANISM: Hepatitis B virus

<400> SEQUENCE: 34

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Val Lys Asp Asp Trp Pro Ala Ala Asn Gln Val Gly
            35                  40                  45

<210> SEQ ID NO 35
<211> LENGTH: 47
<212> TYPE: PRT
<213> ORGANISM: Hepatitis B virus

<400> SEQUENCE: 35

Gly Thr Asn Leu Ser Val Pro Asn Pro Leu Gly Phe Phe Pro Asp His
1               5                   10                  15

Gln Leu Asp Pro Ala Phe Lys Ala Asn Ser Glu Asn Pro Asp Trp Asp
            20                  25                  30

Leu Asn Pro Asn Lys Asp Asn Trp Pro Asp Ala Asn Lys Val Gly
            35                  40                  45

<210> SEQ ID NO 36
<211> LENGTH: 47
<212> TYPE: PRT
<213> ORGANISM: Hepatitis B virus

<400> SEQUENCE: 36

Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 37
<211> LENGTH: 47
<212> TYPE: PRT
<213> ORGANISM: Hepatitis B virus

<400> SEQUENCE: 37

Gly Lys Asn Ile Ser Thr Thr Asn Pro Leu Gly Phe Phe Pro Asp His
1               5                   10                  15

Gln Leu Asp Pro Ala Phe Arg Ala Asn Thr Arg Asn Pro Asp Trp Asp
            20                  25                  30

His Asn Pro Asn Lys Asp His Trp Thr Glu Ala Asn Lys Val Gly
        35                  40                  45

<210> SEQ ID NO 38
<211> LENGTH: 47
<212> TYPE: PRT
<213> ORGANISM: Hepatitis B virus

<400> SEQUENCE: 38

Gly Gln Asn Leu Ser Val Pro Asn Pro Leu Gly Phe Phe Pro Asp His
1               5                   10                  15

Gln Leu Asp Pro Leu Phe Arg Ala Asn Ser Ser Ser Pro Asp Trp Asp
            20                  25                  30

Phe Asn Thr Asn Lys Asp Ser Trp Pro Met Ala Asn Lys Val Gly
        35                  40                  45

<210> SEQ ID NO 39
<211> LENGTH: 47
<212> TYPE: PRT
<213> ORGANISM: Hepatitis B virus

<400> SEQUENCE: 39

Gly Lys Asn Leu Ser Ala Ser Asn Pro Leu Gly Phe Leu Pro Asp His
1               5                   10                  15

Gln Leu Asp Pro Ala Phe Arg Ala Asn Thr Asn Asn Pro Asp Trp Asp
            20                  25                  30

Phe Asn Pro Lys Lys Asp Pro Trp Pro Glu Ala Asn Lys Val Gly
        35                  40                  45

<210> SEQ ID NO 40
<211> LENGTH: 47
<212> TYPE: PRT
<213> ORGANISM: Hepatitis B virus

<400> SEQUENCE: 40

Gly Gln Asn Leu Ser Val Pro Asn Pro Leu Gly Phe Phe Pro Asp His
1               5                   10                  15

Gln Leu Asp Pro Leu Phe Arg Ala Asn Ser Ser Ser Pro Asp Trp Asp
            20                  25                  30

Phe Asn Thr Asn Lys Asp Asn Trp Pro Met Ala Asn Lys Val Gly
        35                  40                  45

<210> SEQ ID NO 41

```
<211> LENGTH: 3221
<212> TYPE: DNA
<213> ORGANISM: Hepatitis B virus

<400> SEQUENCE: 41
ttccactgcc ttccaccaag ctctgcagga tcccaaagtc aggggtctgt attttcctgc      60
tggtggctcc agttcaggaa cagtcaaccc tgctccaaat attgcctctc acatctcgtc     120
aatctccgcg aggactgggg accctgtgcc gaacatggag aacatcacat caggattcct     180
aggacccctg ctcgtgttac aggcggggtt tttcttgttg acaagaatcc tcacaatacc     240
gcagagtcta gactcgtggt ggacttctct caattttcta gggggatcac ccgtgtgtct     300
tggccaaaat tcgcagtccc caacctccaa tcactcacca acctcctgtc ctccaatttg     360
tcctggttat cgctggatgt gtctgcggcg ttttatcata ttcctcttca tcctgctgct     420
atgcctcatc ttcttattgg ttcttctgga ttatcaaggt atgttgcccg tttgtcctct     480
aattccagga tcaacaacaa ccagtacggg accatgcaaa acctgcacga ctcctgctca     540
aggcaactct atgtttccct catgttgctg tacaaaacct atggatggaa attgcacctg     600
tattcccatc ccatcgtcct gggctttcgc aaaataccta tgggagtggg cctcagtccg     660
tttctcttgg ctcagtttac tagtgccatt tgttcagtgg ttcgtagggc tttcccccac     720
tgtttggctt tcagctatat ggatgatgtg gtattggggg ccaagtctgt acagcatcgt     780
gagtcccttt ataccgctgt taccaatttt cttttgtctc tgggtataca tttaaaccct     840
aacaaaacaa aaagatgggg ttattcccta aacttcatgg tctacataat tggaagttgg     900
ggaacgttgc cacaggatca tattgtacaa aagatcaaac actgttttag aaaacttcct     960
gttaacagac ctattgattg gaaagtatgt caaagaattg tgggtctttt gggctttgct    1020
gctccattta ctcaatgtgg atatcctgcc ttaatgcctt gtatgcatg tatacaagct    1080
aaacaggctt ttactttctc gccaacttac aaggcctttc taagtaaaca gtatatgaac    1140
ctttaccccg ttgctcggca acggcctggt ctgtgccaag tgtttgctga cgcaaccccc    1200
actggctggg gcttggccat aggccatcag cgcatgcgtg gaacctttgt ggctcctctg    1260
ccgatccata ctgcggaact cctagccgct tgttttgctc gcagccggtc tggagcaaag    1320
ctcatcggaa ctgataattc tgtcgtcctc tcgcggaaat atacatcgtt tccatggctg    1380
ctaggctgta ctgccaactg gatccttcgc gggacgtcct ttgtttacgt cccgtcggcg    1440
ctgaatcccg cggacgaccc ctcgcggggc cgcttgggag tctctcgtcc ccttctccgt    1500
ctgccgttcc agccgaccac ggggcgcacc tctctttacg cggtctcccc gtctgtgcct    1560
tctcatctgc cggtccgtgt gcacttcgct tcacctctgc acgttgcatg gagaccaccg    1620
tgaacgccca tcagatcctg cccaaggtct tacataagag gactcttgga ctctcagcaa    1680
tgtcaatgac cgaccttgag gcctacttca aagactgtgt gtttaaggac tgggaggagc    1740
ttggggagga gattaggtta aaggtgtttg tattaggagg ctgtaggcat aaattggtct    1800
gcgcaccagc accatgcaac ttttcacctc tgcctaatc atctcttgta catgtcccac    1860
ttttcaagcc tccaagctgt gccttgggtg gctttgggc atggacattg acccttataa    1920
agaatttgga gctactgtgg agttactctc gttttgcct tctgacttct ttccttccgt    1980
cagagatctc ctagacaccg cctcagctct gtatcgaaga ccttagagt ctcctgagca    2040
ttgctctcct caccatactg cactcaggca agccattctc tgctgggtgg aattgatgac    2100
tctagccacc tgggtgggta ataatttgga agatccagca tccagggatc tagtagtcaa    2160
ttatgttaat actaacatgg gtttaaagat caggcaacta ttgtggtttc atatatcttg    2220
```

```
tcttactttt ggaagacaga ctgtgctaga atatttggtc tctttcggag tgtggattcg    2280
cactcctcca gcttatagac caccaaatgc ccctatctta tcaacacttc cggagactac    2340
tgttgttaga cgacgggacc gaggcaggtc ccctagaaga agaactccct cgcctcgcag    2400
acgcagatct caatcgccgc gtcgcagaag atctcaatct cgggaatctc aatgttagta    2460
ttccttggac tcataaggtg ggaaatttta ctgggcttta ttcctctaca gtacctatct    2520
ttaatcctga atggcaaact ccttcctttc ctaagattca tttacaagag gacattatta    2580
ataggtgtca acaatttgtg ggccctctca ctgtaaatga aaagagaaga ctgaaattaa    2640
ttatgcctgc cagattctat cctacccaca ctaaatattt gcccttagac aaaggaatta    2700
aaccttatta tccagatcag gtagttaatc attacttcca aaccagacat tatttacata    2760
ctctttggaa ggctgggatt ctatataaga gggaaaccac acgtagcgca tcattttgcg    2820
ggtcaccata ttcttgggaa caagagctac atcatgggag gttggtcatc aaaacctcgc    2880
aaaggcatgg ggacgaacct ttctgttccc aaccctctgg gattctttcc cgatcatcag    2940
ttggaccctg cattcggagc caattcaaac aatccagatt gggacttcaa ccccatcaag    3000
gaccactggc cagcaggcaa ccaggtagga gtgggagcat cgggccaag gctcacccct    3060 ccacacggcg gtattttggg gtggagccct caggctcagg gcatattggc cacagtgtca    3120
acaattcctc ctcctgcctc caccaatcgg cagtcaggaa ggcagcctac tcccatctct    3180
ccacctctaa gagacagtca tcctgaggcc atgcagtgga a                        3221

<210> SEQ ID NO 42
<211> LENGTH: 3215
<212> TYPE: DNA
<213> ORGANISM: Hepatitis B virus

<400> SEQUENCE: 42
aactccacca ctttccacca aactcttcaa gatcccagag tcagggccct gtaccttcct      60
gctggtggct ccagttcaga aatagtgagc cctgctcaga atactgtctc tgccatatcg     120
tcaatcttat cgaagactgg ggaccctgta ccgaacatgg agaacatcgc atcaggactc     180
ctaggacccc tgctcgtgtt acaggcgggg ttttcttgt tgacaaaaat cctcacaata     240
ccacagagtc tagactcgtg gtggacttct ctcaattttc taggggaac acccgtgtgt     300 cttggccaaa attcgcagtc ccaaatctcc agtcactcac caacctgttg tcctccaatt     360
tgtcctgggt atcgctggat gtgtctgcgg cgttttatca tattcctctg catcctgctg     420
ctatgcctca tcttcttgtt ggttcttctg gactatcaag gtatgttgcc cgtttgtcct     480
ctaattccag gatcatcaac aaccagcacc ggaccatgca aaacctgcac aactcctgct     540
caaggaacct ctatgtttcc ctcatgttgc tgtacaaaac ctacgacgg aaactgcacc     600 tgtattccca tcccatcatc ttgggctttc gcaaaattcc tatgggagtg ggcctcagtc     660
cgtttctctt ggctcagttt actagtgcca tttgttcagt ggttcgtagg ctttccccc     720 actgtctggc tttcagttat atcgatgatg tggttttggg ggccaagtct gtacaacatc     780
ttgagtccct ttataccgct gttaccaatt ttcttttgtc tttgggtata catttaaacc     840
ctcacaaaac aaaaagatgg ggatattccc ttaacttcat gggatatgta attgggagtt     900
ggggcacatt gccacaggaa catattgtac aaaaaatcaa aatgtgtttt aagaaacttc     960
ctgtaaacag gcctattgat tggaaagtat gtcaacgaat gtgggtcttt tggggtttg    1020 ccgccccttt tacgcaatgt ggatatcctg ctttaatgcc tttatatgca tgtatacaag    1080
```

```
caaaacaggc ttttactttc tcgccaactt acaaggcctt tctaagtaaa cagtatatga    1140
acctttaccc cgttgctcgg caacggcctg gtctgtgcca agtgtttgct gacgcaaccc    1200
ccactggttg gggcttggcc attggccatc agcgcatgcg tgggaccttt gtgtctcctc    1260
tgccgatcca tactgcggaa ctcctagccg cttgttttgc tcgcagcagg tctggggcaa    1320
aactcatcgg gactgacaat tctgtcgtgc tctcccgcaa gtatacatca tttccatggc    1380
tgctaggctg tgctgccaac tggatcctgc gcgggacgtc ctttgtttac gtcccgtcgg    1440
cgctgaatcc cgcggacgac ccctcccggg gccgcttggg gctctaccgc ccgcttctcc    1500
gcctgttgta ccgaccgacc acggggcgca cctctctta cgcggactcc ccgtctgtgc    1560
cttctcatct gccggaccgt gtgcacttcg cttcacctct gcacgtcgca tggagaccac    1620
cgtgaacgcc cacaggaacc tgcccaaggt cttgcataag aggactcttg gactttcagc    1680
aatgtcaacg accgaccttg aggcatactt caaagactgt gtgtttactg agtgggagga    1740
gttgggggag gagattaggt taaaggtctt tgtactagga ggctgtaggc ataaattggt    1800
gtgttcacca gcaccatgca actttttcac ctctgcctaa tcatctcatg ttcatgtcct    1860
actgttcaag cctccaagct gtgccttggg tggctttggg gcatggacat tgacccgtat    1920
aaagaatttg gagcttctgc ggagttactc tctttttac cttctgactt ctttccttct    1980
attcgagatc ttctcgacac cgcctctgct ctgtatcggg aggccttaga gtctccggaa    2040
cattgttcac ctcaccatac ggcactcagg caagctattc tgtgttgggg tgagttgatg    2100
aatctagcca cctgggtggg aagtaatttg gaagatccag catccaggga attagtagtc    2160
ggctatgtca acgttaatat gggcctaaaa cttagacaac tattgtggtt tcacatttcc    2220
tgtcttactt ttgggagaga aactgttctt gaatatttgg tgtcttttgg agtgtggatt    2280
cgcactcctt ctgcatatag accaccaaat gcccctatcc tatcaacact tccggaaact    2340
actgttgtta gacgaagagg caggtcccct agaagaagaa ctccctcgcc tcgcagacga    2400
aggtctcaat cgccgcgtcg cagaagatct caatctcggg aatctcaatg ttagtattcc    2460
ttggacacat aaggtgggaa actttacggg gctttattct tctacggtac cttgttttaa    2520
tcctaaatgg caaactcctt cttttcctga cattcatttg caggaggaca ttgttgatag    2580
atgtaagcaa tttgtggggc cccttacagt aaatgaaaac aggagactaa aattaattat    2640
gcctgctagg ttttatccca atgttactaa atatttgccc ttagataaag ggatcaaacc    2700
gtattatcca gagtatgtag ttaatcatta cttccagacg cgacattatt tacacactct    2760
ttggaaagcg gggatcttat ataaaagaga gtccactcgt agcgcctcat tttgcgggtc    2820
accatattct tgggaacaag atctacagca tgggaggttg gtcttccaaa cctcgaaaag    2880
gcatggggac aaatctttct gtccccaatc cctgggatt cttccccgat catcagttgg    2940
accctgcatt caaagccaac tcagaaaatc cagattggga cctcaacccg cacaaggaca    3000
actggccgga cgccaacaag gtgggagtgg gagcattcgg gccagggttc accctctccc    3060 atgggggct gttggggtgg agccctcagg ctcaggcct actcacaact gtgccagcag    3120
ctcctcctcc tgcctccacc aatcggcagt caggaaggca gcctactccc ttatctccac    3180
ctctaaggga cactcatcct caggccatga agtgg                              3215
```

<210> SEQ ID NO 43
<211> LENGTH: 3215
<212> TYPE: DNA
<213> ORGANISM: Hepatitis B virus

<400> SEQUENCE: 43

```
aattccacaa cattccacca agctctgcta gacccccagag tgaggggcct atactttcct      60
gctggtggct ccagttccgg aacagtaaac cctgttccga ctactgcctc acccatatcg     120
tcaatcttct cgaggactgg ggaccctgca ccgaacatgg agagcacaac atcaggattc     180
ctaggacccc tgctcgtgtt acaggcgggg ttttcttgt tgacaagaat cctcacaata     240
ccacagagtc tagactcgtg gtggacttct ctcaattttc taggggagc acccacgtgt     300 cctggccaaa attcgcagtc cccaacctcc aatcactcac caacctcttg tcctccaatt     360
tgtcctggct atcgctggat gtgtctgcgg cgttttatca tattcctctt catcctgctg     420
ctatgcctca tcttcttgtt ggttcttctg gactaccaag gtatgttgcc cgtttgtcct     480
ctacttccag gaacatcaac taccagcacg ggaccatgca agacctgcac gagtcctgct     540
caaggaacct ctatgtttcc ctcttgttgc tgtacaaaac cttcggacgg aaactgcact     600
tgtattccca tcccatcatc ctgggctttc gcaagattcc tatgggagtg ggcctcagtc     660
cgtttctcct ggctcagttt actagtgcca tttgttcagt ggttcgtagg ctttccccc     720 actgtttggc tttcagttat atggatgatg tggtattggg ggccatgtct gtacaacatc     780 ttgagtcct ttacctct attaccaatt ttcttttgtc tttgggtata catttgaacc     840
ctaataaaac caaacgttgg ggctactccc ttaacttcat gggatatgta attggaagtt     900
ggggtacttt accgcaagaa catattgtac aaaaacttaa gcaatgtttt cgaaaactgc     960
ctgtaaatag acctattgat tggaaagtat gtcagagaat tgtgggtctt ttgggctttg    1020 ctgcccctttt tacacaatgt ggctatcctg ctttaatgcc tttatatgca tgtatacaat    1080
ctaagcaggc tttcactttc tcgccaactt acaaggcctt tctgtgtaaa caatatctga    1140
acctttaccc cgttgcccgg caacggtcag gtctctgcca agtgtttgct gacgcaaccc    1200
ccactggatg gggcttggct attggccatc gccgcatgcg tggaaccttt gtggctcctc    1260
tgccgatcca tactgcggaa ctcctagcag cttgttttgc tcgcagccgg tctggagcaa    1320
aacttatcgg caccgacaac tctgttgtcc tctctcggaa gtacacctcc ttttccatggc    1380 tgctagggtg tgctgccaac tggatcctgc gcgggacgtc cttttgtttac gtcccgtcgg    1440 cgctgaatcc cgcggacgac ccgtctcggg gccgtttggg actctaccgt cccttcttc    1500 atctgccgtt ccggccgacc acggggcgca cctctctttta cgcggtctcc ccgtctgtgc    1560
cttctcatct gccggaccgt gtgcacttcg cttcacctct gcacgtcgca tggagaccac    1620
cgtgaacgcc caccaggtct tgcccaaggt cttacataag aggactcttg gactctcagc    1680
aatgtcaacg accgaccttg aggcatactt caaagactgt ttgtttaagg actgggagga    1740
gttgggggag gagattaggt taaaggtctt tgtactagga ggctgtaggc ataaattggt    1800
ctgttcacca gcaccatgca acttttttcac ctctgcctaa tcatctcatg ttcatgtcct    1860
actgttcaag cctccaagct gtgccttggg tggctttggg gcatggacat tgacccgtat    1920
aaagaatttg gagcttctgt ggagttactc tcttttttgc cttctgactt ctttccttct    1980
attcgagatc tcctcgacac cgcctctgct ctgtatcggg aggccttaga gtctccggaa    2040
cattgttcgc ctcaccatac agcactcagg caagctattc tttgttgggg tgagttgatg    2100
aatctggcca cctgggtggg aagtaatttg gaagacccag catccaggga attagtagcc    2160
agctatgtca atgttaatat gggcctaaaa atcagacaac tactgtggtt tcacatttcc    2220
tgtcttactt ttggaagaga aactgttctt gagtatttgg tatctttgg agtgtggatt    2280 cgcactcctc ctgcttacag accaccaaat gcccctatct tatcaacact tccggaaact    2340
```

```
actgttgtta gacgacgagg caggtcccct agaagacgaa ctccctcgcc tcgcagacga   2400
aggtctcaat cgccgcgtcg cagaagatct caatctcggg aatctcaatg ttagtatccc   2460
ttggactcat aaggtgggaa actttactgg gctttattct tctactgtac ctgtctttaa   2520
tccagagtgg caaactccct cctttcctca cattcattta caggaggaca ttattaatag   2580
atgtcaacaa tatgtgggcc ctcttacagt taatgaaaaa agaagattaa aattaattat   2640
gcctgctagg ttctatccta accttaccaa atatttgccc ttggacaaag cattaaacc    2700 atattatcct gaacatgcag ttaatcatta cttcaaaact aggcattatt tacatactct   2760
gtggaaggct ggcattctat ataagagaga aactacacgc agcgcctcat tttgtgggtc   2820
accatattct tgggaacaag agctacagca tgggaggttg gtcttccaaa cctcgacaag   2880
gcatggggac aaatctttct gttcccaatc ctctgggatt ctttcccgat caccagttgg   2940
accctgcgtt cggagccaac tcaaacaatc cagattggga cttcaacccc aacaaggatc   3000
actggccaga gcaaatcag gtaggagcgg gagcattcgg gccagggttc accccaccac    3060
acggcggtct tttggggtgg agccctcagg ctcagggcat actgacaaca gtgccagtag   3120
cacctcctcc tgcctccacc aatcggcagt caggaagaca gcctactccc atctctccac   3180
ctctaagaga cagtcatcct caggccatgc agtgg                              3215
```

<210> SEQ ID NO 44
<211> LENGTH: 3182
<212> TYPE: DNA
<213> ORGANISM: Hepatitis B virus

<400> SEQUENCE: 44

```
aactccacaa ccttccacca aactctgcaa gatcccagag tgagaggcct gtatttccct   60
gctggtggct ccagttcagg aacagtaaac cctgttccga ctactgtctc tcccatatcg   120
tcaatcttct cgaggattgg ggaccctgcg ctgaacatgg agaacatcac atcaggattc   180
ctaggacccc tgctcgtgtt acaggcgggg ttttcttgt tgacaagaat cctcacaata   240
ccgcagagtc tagactcgtg gtggacttct ctcaattttc taggggggaac taccgtgtgt   300 cttggccaaa attcgcagtc cccaacctcc aatcactcac caacctcctg tcctccaact   360
tgtcctggtt atcgctggat gtgtctgcgg cgttttatca tcttcctctt catcctgctg   420
ctatgcctca tcttcttgtt ggttcttctg gactatcaag gtatgttgcc cgtttgtcct   480
ctaattccag gatcttcaac taccagcacg ggaccatgca gaacctgcac gactcctgct   540
caaggaacct ctatgtatcc ctcctgttgc tgtaccaaac cttcggacgg aaattgcacc   600
tgtattccca tcccatcatc ctgggctttc ggaaaattcc tatgggagtg ggcctcagcc   660
cgtttctcct ggctcagttt actagtgcca tttgttcagt ggttcgtcgg gctttccccc   720
actgtttggc tttcagttat atggatgatg tggtattggg ggccaagtct gtacagcatc   780
ttgagtccct ttttaccgct gttaccaatt ttctttttgtc tttgggtata catttaaacc   840
ctgacaaaac aaaaagatgg ggttactctt tacatttcat gggctatgtc attggaagtt   900
atgggtcatt gccacaagat cacatcatac aaaaaatcaa agaatgtttt cgaaaacttc   960
ctgttaacag acctattgat tggaaagtct gtcaacgtat gtgggtcttt tgggttttg    1020 ctgccccttt tacacaatgt ggttatcctg ctttaaagcc tttgtatgca tgtattcaat   1080
ctaagcaggc tttcactttc tcgccaactt acaaggcctt tctgtgtaaa caatacctga   1140
acctttaccc cgttgcccgg caacggccag gtctgtgcca gtgtttgct gacgcaaccc    1200 ccactggctg gggcttggtc atgggccatc agcgcatgcg tggaaccttt ctggctcctc   1260
```

```
tgccgatcca tactgcggaa ctcctagccg cttgttttgc tcgcagcagg tctggagcaa    1320
acattctcgg gacggataac tctgttgttc tctcccgcaa atatacatcg tttccatggc    1380
tgctaggctg tgctgccaac tggatcctgc gcgggacgtc ctttgtttac gtcccgtcgg    1440
cgctgaatcc cgcggacgac ccttctcggg gtcgcttggg actctctcgt ccccttctcc    1500
gtctgccgtt tcgaccgacc acggggcgca cctctcttta cgcggactcc ccgtctgtgc    1560
cttctcatct gccggaccgt gtgcacttcg cttcacctct gcccgtcgca tggagaccac    1620
cgtgaacgcc caccgagtct tgcccaaggt cttacataag aggactcttg gactctctgt    1680
aatgtcaacg accgaccttg aggcatactt caaagactgt ttgttcaaag actgggagga    1740
gttgggggag gagattagat taaaggtctt tgtactagga ggctgtaggc ataaattggt    1800
ctgcgcacca gcaccatgca acttttttcac ctctgcctaa tcatctcttg ttcatgtcct    1860
actgttcaag cctccaagct gtgccttggg tggctttagg catggacat cgatccttat    1920 aaagaatttg gagctactgt ggagttactc tcgttttttgc cttctgactt ctttccttca    1980
gtacgagatc ttctagatac cgcctcagct ctgtatcggg aagccttaga gtctcctgag    2040
cattgttcac ctcaccatac tgcactcagg caagcagttc tgtgctgggg ggaactaatg    2100
actctagcta cctgggtggg tggtaatttg gaagatccaa catccaggga cctagtagtc    2160
agttatgtca acactaatat gggcctaaag ttccggcaac tattgtggtt tcacatttct    2220
tgtctcactt ttggaagaga aacagtttta gagtatttgg tgtctttcgg agtgtggatt    2280
cgcactcctc cagcttatag accaccaaat gcccctatct tatcaacact tccggagact    2340
actgttgtta gacgacgagg caggtcccct agaagaagaa ctccctcgcc tcgcagacga    2400
aggtctcaat cgccgcgtcg cagaagatct caatctcggg aatctcaatg ttagtattcc    2460
ttggactcat aaggtgggaa actttacggg gctttattct tctactgtac ctgtctttaa    2520
ccctcattgg aaaacacccct cttttcctaa tatacattta caccaagaca ttatcaaaaa    2580
atgtgaacaa tttgtaggcc cactcacagt caatgaaaaa agaagactgc aattgattat    2640
gcctgctagg ttttatccaa atgttaccaa atatttgcca ttggataagg gtatcaaacc    2700
ttattaccca gaacatctag ttaatcatta cttccaaacc agacattatt tacacactct    2760
atggaaggcg ggtatattat ataagagaga acaacacat agcgcctcat tttgtgggtc    2820
accatattct tgggaacaaa agctacagca tggggcagaa tctttccacc agcaatcctc    2880
tgggattctt tcccgaccac cagttggatc cagccttcag agcaaacacc gcaaatccag    2940
attgggactt caatcccaac aaggacacct ggccagacgc caacaaggta ggagctggag    3000
cattcgggct gggattcacc ccaccgcacg gaggcctttt ggggtggagc cctcaggctc    3060
agggcatact acaaaccttg ccagcaaatc cgcctcctgc ctctacccat cgccagtcag    3120
gaaggcagcc taccccgctg tctccacctt tgagaaacac tcatcctcag gccatgcagt    3180
gg                                                                   3182

<210> SEQ ID NO 45
<211> LENGTH: 3212
<212> TYPE: DNA
<213> ORGANISM: Hepatitis B virus

<400> SEQUENCE: 45
ttccacagca ttccaccaag ctctgcagga tcccaaagta agaggcctgt attttcctgc      60
tggtggctcc agttccggaa cagtgagccc tgttccgact actgcctcac tcatctcgtc     120
```

```
aatcttctcg aggattgggg accctgcacc gaacatggaa ggcatcacat caggattcct    180
gggacccctg ctcgtgttac aggcggggtt tttcttgttg acaaaaatcc tcacaatacc    240
gcagagtcta gactcgtggt ggacttctct caattttcta gggggagctc ccgtgtgtct    300
tggccaaaat tcgcagtccc caacctccaa tcactcacca acctcttgtc ctccgatttg    360
tcctggctat cgctggatgt gtctgcggcg ttttatcatc ttcctcttca tcctgctgct    420
atgcctcatc ttcttgttgg ttcttctgga ctatcaaggt atgttgcccg tttgtcctct    480
aattccagga tcatcaacca ccagtacggg accctgccga acctgcacga ctcttgctca    540
aggaacctct atgtttccct catgttgctg ttcaaaacct tcggacggaa attgcacttg    600
tattcccatc ccatcatcat gggctttcgg aaaattccta tgggagtggg cctcagcccg    660
tttctcctgg ctcagtttac tagtgccatt tgttcagtgg ttcgccgggc tttcccccac    720
tgtctggctt tcagttatat ggatgatgtg gtattggggg ccaagtctgt acaacatctt    780
gagtcccttt atacctctgt taccaatttt cttttgtctt tgggtataca tttaaatccc    840
aacaaaacaa aacgatgggg atattctctt aatttcatgg gatatgtaat tgggagttgg    900
gggtcattac cacaggaaca catccgaatg aaaatcaaag actgttttag aaaactccct    960
gttaaccggc ctattgattg gaaagtatgt caaagaattg tgggtctttt gggctttgct   1020
gccccttttta cacaatgtgg atatcctgct ttaatgcctc tgtatgcgtg tgttcaatcg   1080
aagcaggctt tcactttctc gccaacttac aaggcctttc tgtgtaaaca atacctgaac   1140
ctttaccccg ttgcccggca acggccaggt ctgtgccaag tgtttgctga tgcaaccccc   1200
actggctggg gcttggccat aggccatcag cgcatgcgtg gaacctttgt ggctcctctg   1260
ccgatccata ctgcggaact cctagccgct tgttttgctc gcagcaggtc tggagcgaaa   1320
cttatcggga cggataattc tgtcgttctc tcccggaaat atacatcatt tccatggctg   1380
ctaggctgtg ctgccaactg gatcctgcga gggacgtcct ttgtctacgt cccgtcagcg   1440
ctgaatcctg cggacgaccc gtctcggggt cgcttgggga tctatcgtcc ccttctccgt   1500
ctgccgttcc ggccgaccac ggggcgcacc tctctttacg cggtctcccc gtctgtgcct   1560
tctcatctgc cggaccgtgt gcacttcgct tcacctctgc acgtcgcatg gagaccaccg   1620
tgaacgccca tcaaatcttg cccaaggtct tacataagcg gactcttgga cttttctgcaa  1680
tgtcaacgac cgaccttgag gcatacttca aagactgttt gtttaaagac tgggaggagt   1740
tgggggagga gattagatta aaggtctttg tactaggagg ctgtaggcat aaattggtct   1800
gcgcaccagc accatgcaac ttttttcacct ctgcctaatc atctcttgtt catgtcctac   1860
tgttcaagcc tccaagctgt gccttgggtg gctttgggge atggacattg acccttataa   1920
agaatttgga gctactgtgg agttactctc gttttttgccg tctgacttct ttccgtcagt   1980
tagagatctt ctagataccg cctcagctct gtatcgggat gccttagaat ctcctgagca   2040
ttgttcacct caccatactg cactcaggca agccattctt tgctgggggg aactaatgac   2100
tctagctacc tgggtgggtg taaatttgga agatccagca tccagggacc tagtagtcag   2160
ttatgtcaat actaatatgg gcctaaagtt caggcaatta ttgtggtttc acatttcttg   2220
tctcactttt ggaagagaaa ccgtcataga gtatttggtg tcttttggag tgtggattcg   2280
cactcctcca gcttatagac caccaaatgc ccctatctta tcaacacttc cggagaatac   2340
tgttgttaga cgaagaggca ggtcccctag aagaagaact ccctcgcctc gcagacgaag   2400
atctcaatcg ccgcgtcgca gaagatctca atctccagct tcccaatgtt agtattcctt   2460
ggactcacaa ggtgggaaat tttacgggcc tttactcttc tactataccct gtctttaatc   2520
```

```
ctaactggaa aactccatct tttcctgata ttcatttgca ccaagacatt attaacaaat    2580
gtgaacaatt tgtaggtcct ctaacagtaa atgaaaaacg aagattaaac ttagtcatgc    2640
ctgctagatt ttttcccatc tctacgaaat atttgcccct agagaagggt ataaaacctt    2700
attatccaga taatgtagtt aatcattact tccaaaccag acactattta catacccctat   2760 ggaaggcggg catcttatat aaacgggaaa ctacacgtag cgcctcattt tgtgggtcac    2820
cttattcttg ggaacaagag ctacatcatg gggctttctt ggacggtccc tctcgaatgg    2880
gggaagaatc attccaccac caatcctctg gattttttc ccgaccacca gttggatcca     2940
gcattcagag caaacaccag aaatccagat gggaccaca atcccgacaa agaccactgg     3000
acagaagcca acaaggtagg agtgggagca ttcgggccgg ggttcactcc cccacacgga    3060 ggcctttttgg ggtggagccc tcaggctcaa ggcatgctaa aaacattgcc agcagatccg   3120
cctcctgcct ccaccaatcg gcagtcagga aggcagccta ccccaatcac tccacctttg    3180
agagacactc atcctcaggc catgcagtgg aa                                  3212

<210> SEQ ID NO 46
<211> LENGTH: 3215
<212> TYPE: DNA
<213> ORGANISM: Hepatitis B virus

<400> SEQUENCE: 46
ctccactcag ttccaccagg ctctgttaga tccgagagta agggctctgt attttcctgc      60
tggtggctcc agttcagaga cacagaaccc tgctccgact attgcctctc tcacatcatc    120
aatcttcttg aagactgggg gccctgctac gaacatggac aacatcacat caggactcct    180
aggacccctg ctcgtgttac aggcggtgtg tttcttgttg acaaaaatcc tcacaatacc    240
acagagtcta gactcgtggt ggacttctct caattttcta gggggaacac ccgggtgtcc    300
tggccaaaat tcgcagtccc caacctccaa tcacttacca acctcctgtc tccaacttg     360 tcctggctat cgctggatgt gtctgcggcg ttttatcatc ttcctcttca tcctgctgct    420
atgcctcatc ttcttgttgg ttcttctgga ctatcaaggt atgttgcccg tttgtcctct    480
acttccagga tccacgacca ccagcacggg accatgcaaa acctgcacaa ctcttgctca    540
aggaacctct atgtttccct cttgctgctg ttccaaaccc tcggacggaa actgcacttg    600
tattcccatc ccatcatcct gggctttagg aaaataccta gggagtgggg cctcagcccg    660
tttctcctgg ctcagtttac tagtgcaatt tgttcagtgg tgcgtagggc tttccccac    720 tgtctggctt ttagttatat ggatgatctg gtattgggggg ccaaatctgt gcagcatctt   780
gagtcccttt ataccgctgt taccaatttt ctgttatctg tgggtatcca tttaaatacc    840
tcgaaaacaa aaagatgggg ttatacccta aatttcatgg gttatgttat ggcagttgg    900 ggatcattac cacaagatca cattgtacaa aaaatcaaag attgttttcg taaacttcct    960
gtaaatcgcc ctattgattg aaagtttgt caacgcattg tgggtctttt gggctttgcc    1020
gcccccttta tcaatgtgg ttatcctgct ctcatgcctc tgtatgcctg tataactgct    1080
aaacaggctt ttgtcttttc gccaacttac aaggcctttc tatgtcaaca atacatgaac   1140
ctttaccccg ttgctcggca acggccaggc tgtgccaag tgtttgctga cgcaacccccc   1200 actggttggg gcttggccat tggccatcag cgcatgcgtg gaacctttgt ggctcctctg    1260
ccgatccata ctgcggaact ccttgcagct tgtttcgctc gcagccggtc tggagcgaaa    1320
ctcatcggca cagacaactc tgttgtcctc tctaggaagt acacctcctt cccatggctg    1380
```

```
ctcggttgtg ctgccaactg gatcctacgc gggacgtcct ttgtttacgt cccgtcggcg    1440
ctgaatccag cggacgatcc ctctcggggt cgcttgggc  tgtatcgccc ccttctccgt    1500
ctgccgttcc agccgacgac gggtcgcacc tctctttacg cggcctcccc gtctgttcct    1560
tctcgtctgc cggaccgtgt gcacttcgct tcacctctgc acgtcgcatg agaccaccg     1620 tgaacgcccc tcgaagcttg ccaacagtct tacataagcg gactcttgga ctttcaggaa    1680
ggtcaatcac ctggatcgaa gaatacatca aagactgtgt atttaaggac tgggaggagc    1740
tgggggagga gattaggtta aaggtctttg tattaggagg ctgtaggcat aaattggtct    1800
gttcaccagc accatgcaac ttttcaccct ctgcctaatc atcttttgtt catgtcctac    1860
tgttcaagcc tccaagctgt gccttgggtg gctttggggc atggacattg accttataa    1920 agaatttgga gcttctgtgg aattactctc ttttttgcct tctgacttct tcccgtcagt    1980
tcgggaccta ctcgacaccg cttcagccct ctaccgggat gctttagaat caccagaaca    2040
ttgcacacct aaccataccg ctctcaggca agctatattg tgctggggtg agttaatgac    2100
tttggcttcc tgggtgggca ataacttgga agatcctgct gctagggacc tagtggttaa    2160
ctatgtcaat actaacatgg gcctaaaaat tagacaattg ctgtggtttc acatttcctg    2220
ccttactttt ggaagagaaa cagttcttga gtatttggtg tcttttggag tgtggattcg    2280
cactcctcct gcttatagac caccaaatgc ccctatctta tccacacttc cggaaactac    2340
tgttgttaga cgacgaggca ggtcccctcg aagaagaact ccctcgcctc gcagacgaag    2400
gtctcaatcg ccgcgtcgca gaagatctca atctccagct tcccaatgtt agtattcctt    2460
ggactcataa ggtgggaaat tttacgggac tctattcctc tactgttcct acttttaatc    2520
ctgactggtt aactccttct tttcctgaca ttcatttaca tcaagatttg atacacaaat    2580
gtgaacaatt gtaggccct  tcacaaaaaa atgaattgag aagattaaaa ttagttatgc    2640
catccagatt ttttcctaag gttaccaaat attttcctat ggaaaaggga attaaacct    2700 attatcctga taacgtggtt aatcattatt ttaagaccag acactatttg catactttat    2760
ggaargcrgg cattctatat aagagagaat ccacacgtag cgcctcattt tgtgggtcac    2820
catattcttg ggaacaagag ctacagcatg ggagcacctc tatcaacgac tcgaaggggc    2880
atgggacaga atctctctgt acccaatcct ctgggattct ttccagacca tcagctggat    2940
cctctattca gggcaaattc cagcagtccc gactgggact tcaacaaaaa caaggacaat    3000
tggccaatgg caaacaaggt aggagtggga ggatacggtc ctgggttcac accccacac    3060 ggtggcctgt tggggtggag tccacaggca cagggtgtgc ttacaacatt gccagcagat    3120
ccgcctcctg cttccaccaa tcggcggtcc gggagaaaac caaccccagt ctctccacct    3180
ctaagagaca ctcatccaca ggccatgcag tggaa                              3215
```

<210> SEQ ID NO 47
<211> LENGTH: 3248
<212> TYPE: DNA
<213> ORGANISM: Hepatitis B virus

<400> SEQUENCE: 47

```
ctctacagca ttccaccaag ctctacaaaa tcccaaagtc aggggcctgt attttcctgc     60
tggtggctcc agttcaggga tagtgaaccc tgttccgact attgcctctc acatctcgtc    120
aatcttctcc aggattgggg accctgcacc gaacatggag aacatcacat caggattcct    180
aggacccctg ctcgtgttac aggcgggggtt tttcttgttg acaagaatcc tcacaatacc    240
gcagagtcta gactcgtggt ggacttctct caattttcta ggggagtgc  ccgtgtgtcc    300
```

-continued

```
tggcctaaat tcgcagtccc caacctccaa tcactcacca atctcctgtc ctccaacttg      360
tcctggctat cgctggatgt gtctgcggcg ttttatcata ttcctcttca tcctgctgct      420
atgcctcatc ttcttgttgg ttcttctgga ctatcaaggt atgttgcccg tttgtcctct      480
gattccagga tcctcgacca ccagcacggg accctgcaaa acctgcacga ctcctgctca      540
aggcaactct atgtatccct catgttgctg tacaaaacct tcggacggaa attgcacctg      600
tattcccatc ccatcatctt gggctttcgc aaaatcccta tgggagtggg cctcagtccg      660
tttctcttgg ctcagtttac tagtgccatt tgttcagtgg ttcgtagggc tttcccccac      720
tgtctggctt tcagctatat ggatgatgtg gtattggggg ccaaatctgt acaacatctt      780
gagtcccttt ataccgctgt taccaatttt cttttgtctt tgggtataca tctaaaccct      840
aacaaaacaa aaagatgggg ttattcctta aattttatgg gatatgtaat tggaagttgg      900
ggtactttgc cacaagaaca catcacacag aaaattaagc aatgttttcg gaaactccct      960
gttaacaggc caattgattg gaaagtctgt caacgaataa ctggtctgtt gggtttcgct     1020 gctccttta cccaatgtgg ttaccctgcc ttaatgcctt tatatgcatg tatacaagct     1080
aagcaggctt ttactttctc gccaacttat aaggcctttc tctgtaaaca atacatgaac     1140
ctttaccccg ttgctaggca acggcccggt ctgtgccaag tgtttgctga cgcaaccccc     1200
actggttggg gcttggccat cggccatcag cgcatgcgtg aacctttgt ggctcctctg     1260 ccgatccata ctgcggaact cctagctgct tgttttgctc gcagccggtc tggagcaaaa     1320
ctcattggga ctgacaattc tgtcgtcctt tctcggaaat atacatcctt tccatggctg     1380
ctaggctgtg ctgccaactg gatccttcgc gggacgtcct ttgtttacgt cccgtcagcg     1440
ctgaatccag cggacgaccc ctcccggggc cgtttgggc tctgtcgccc ccttctccgt     1500
ctgccgttcc tgccgaccac ggggcgcacc tctctttacg cggtctcccc gtctgttcct     1560
tctcatctgc cggaccgtgt gcacttcgct tcacctctgc acgttacatg gaaaccgcca     1620
tgaacacctc tcatcatcta ccaaggcagt tatataagag gactcttgga ctgtttgtta     1680
tgtcaacaac cggatggag aaatacttca aggactgtgt ttttgctgag tgggaagaat     1740
taggcaatga gtccaggtta atgacctttg tattaggagg ctgtaggcat aaattggtct     1800
gcgcaccagc accatgtaac ttttcacct ctgcctaatc atctcttgtt catgtcctac     1860
tgttcaagcc tccaagctgt gccttgggtg gctttagggc atggatagaa caactttgcc     1920
atatggcctt tttggcttag acattgaccc ttataaagaa tttggagcta ctgtggagtt     1980
gctctcgttt ttgccttctg actttttccc gtctgttcgt gatcttctcg acaccgcttc     2040
agctttgtac cgggaatcct tagagtcctc tgatcattgt tcgcctcacc atacagcact     2100
caggcaagca attctgtgct ggggtgagtt gatgactcta gctacctggg tgggtaataa     2160
tttggaagat ccagcatcca gagatttggt ggtcaattat gttaatacta atatgggttt     2220
aaaaatcagg caactattgt ggtttcacat ttcctgtctt acttttggga gagaaaccgt     2280
tcttgagtat ttggtgtctt ttggagtgtg gattcgcact cctcctgctt atagaccacc     2340
aaatgcccct atcctatcaa cacttccgga gactactgtt gttagacgaa gaggcaggtc     2400
ccctcgaaga agaactccct cgcctcgcag acgaagatcc caatcgccgc gtcgcagaag     2460
atctgcatct ccagcttccc aatgttagta ttccttggac tcacaaggtg ggaaacttta     2520
cggggctgta ttcttctact atacctgtct ttaatcctga ttggcaaact ccttcttttc     2580
caaatatcca tttgcatcaa gacattataa ctaaatgtga acaatttgtg ggccctctca     2640
```

| | |
|---|---|
| cagtaaatga gaaacgaaga ttaaaactag ttatgcctgc cagatttttc ccaaactcta | 2700 |
| ctaaatattt accattagac aaaggtatca aaccgtatta tccagaaaat gtagttaatc | 2760 |
| attacttcca gaccagacat tatttacata cccttttggaa ggcgggtatt ctatataaga | 2820 |
| gagaaacatc ccgtagcgct tcattttgtg ggtcaccata tacttgggaa caagatctac | 2880 |
| agcatggggc tttcttggac ggtccctctc gagtggggaa agaacctttc caccagcaat | 2940 |
| cctctaggat tccttcccga tcaccagttg gacccagcat tcagagcaaa taccaacaat | 3000 |
| ccagattggg acttcaatcc caaaaggac ccttggccag aggccaacaa ggtaggagtt | 3060 |
| ggagcctatg gacccggtt caccccctcca cacggaggcc ttttggggtg gagccttcag | 3120 |
| tctcagggca cactaacaac tttgccagca gatccgcctc ctgcctccac caatcgtcag | 3180 |
| tcagggaggc agcctactcc catctctcca ccactaagag acagtcatcc tcaggccatg | 3240 |
| cagtggaa | 3248 |

<210> SEQ ID NO 48
<211> LENGTH: 3215
<212> TYPE: DNA
<213> ORGANISM: Hepatitis B virus

<400> SEQUENCE: 48

| | |
|---|---|
| ctcaacacag ttccaccaag cactgttgga tccgagagta aggggggctgt attttcctgc | 60 |
| tggtggctcc agttcagaaa cacagaaccc tgctccgact attgcctctc tcacatcatc | 120 |
| aatcttctcg aagactgggg accctgctat gaacatggag aacatcacat caggactcct | 180 |
| aggacccctt ctcgtgttac aggcggtgtg tttcttgttg acaaaaatcc tcacaatacc | 240 |
| aaagagtcta gactcgtggt ggacttctct caattttcta ggggtaccac ccgggtgtcc | 300 |
| tggccaaaat tcgcagtccc caatctccaa tcacttacca acctcctgtc ctccaacttg | 360 |
| tcctggctat cgttggatgt gtctgcggcg ttttatcatc ttcctcttca tcctgctgct | 420 |
| atgcctcatc ttcttgttgg ttcttctgga ctatcaaggt atgttgcccg tgtgtcctct | 480 |
| acttccagga twacaacca ccagcacggg accctgcaaa acctgcacca ctcttgctca | 540 |
| aggaacctct atgtttccct cctgctgctg taccaaacct tcggacggaa attgcacctg | 600 |
| tattcccatc ccatcatctt gggctttcgg aaaataccta tgggagtggg cctcagcccg | 660 |
| tttctcttgg ctcagtttac tagtgcaatt tgttcagtgg tgcgtagggc tttccccccac | 720 |
| tgtctggctt ttagttatat ggatgatctg gtattggggg ccaaatctgt gcagcatctt | 780 |
| gagtcccttt ataccgctgt taccaatttt ttgttatctg tgggcatcca tttgaacaca | 840 |
| gctaaaacaa aatggtgggg ttattccctt cactttatgg gttatataat gggagttgg | 900 |
| gggaccttgc tcaggaaca tattgtgcat aaaatcaaag attgctttcg caaacttccc | 960 |
| gtgaatagac ccattgattg aaggtttgt caacgcattg tgggtctttt gggctttgca | 1020 |
| gccccttta tcaatgtggg ttatcctgct ctcatgccct gtatgcctg tattrccgct | 1080 |
| aagcaggctt ttgtttttctc gccaacttac aaggcctttc tctgtaaaca atacatgaac | 1140 |
| cttttacccccg ttgctcggca acggccaggc cttgccaag tgtttgctga cgcaaccccc | 1200 |
| actggctggg gcttggcgat tggccatcag cgcatgcgcg gaaccttttgt ggctcctctg | 1260 |
| cccatccata ctgcggaact cctagccgct tgtttcgctc gcagcaggtc tggagcggac | 1320 |
| attatcggca ctgacaactc cgttgtcctt tctcggaagt acacctcctt cccatggctg | 1380 |
| ctaggctgtg ctgccaactg gatcctgcgc gggacgtcct ttgtctacgt cccgtcggcg | 1440 |
| ctgaatcctg cggacgaccc ctctcgtggt cgcttggggc tctgccgccc tcttctccgc | 1500 |

-continued

```
ctgccgttcc ggccgacgac gggtcgcacc tctctttacg cggactcccc gcctgtgcct    1560
tctcatctgc cggcccgtgt gcacttcgct tcacctctgc acgtcgcatg gagaccaccg    1620
tgaacgcccc ttggaacttg ccaacaacct tacataagag gactcttgga ctttcgcccc    1680
ggtcaacgac ctggattgag gaatacatca agactgtgt atttaaggac tgggaggagt    1740
cgggggagga gttgaggtta aaggtctttg tattaggagg ctgtaggcat aaattggtct    1800
gttcaccagc accatgcaac ttttcaccct ctgcctaatc atcttttgtt catgtcccac    1860
tgttcaagcc tccaagctgt gccttgggtg gctttgggc atggacattg acccttataa    1920
agaatttgga gcttctgtgg agttactctc atttttgcct tctgacttct tcccgtctgt    1980
ccgggaccta ctcgacaccg cttcagccct ctaccgagat gccttagaat caccagaaca    2040
ttgcaccccc aaccacactg ctctcaggca agctattttg tgctggggtg agttgatgac    2100
cttggcttcc tgggtgggca ataatttaga ggatcctgca gcaagagatc tagtagttaa    2160
ttatgtcaat actaacatgg gcctaaaaat tagacaatta ttatggtttc acatttcttg    2220
ccttacattt ggaagagaaa ctgtgcttga gtatttggtg tcttttggag tgtggattcg    2280
cactccacct gcttatagac caccaaatgc ccctatccta tcaacacttc cggagactac    2340
tgttgttaga caacgaggca gggcccctag aagaagaact ccctcgcctc gcagacgaag    2400
atctcaatct ccgcgtcgca gaagatctca atctccagct tcccaatgtt agtattcctt    2460
ggactcataa ggtgggaaac tttaccggtc tttactcctc tactataccct gttttcaatc    2520 ctgactggtt aactccttct tttcctgaca ttcacttgca tcaagatctg atacaaaaat    2580
gtgaacaatt tgtaggccca ctcactacaa atgaaggag acgattgaaa ctaattatgc    2640
cagctaggtt ttatcccaaa gttactaaat acttcccttt ggataaaggt attaagcctt    2700
actatccaga gaatgtggtt aatcattact ttaaaactag acattattta catactttgt    2760
ggaaggcagg aattctatat aagagagaat ccacacatag cgcctcattt tgtgggtcac    2820
catattcctg ggaacaagag ctacagcatg ggagcacctc tctcaacggc gagaaggggc    2880
atgggacaga atctttctgt gcccaatcct ctgggattct ttccagacca ccagttggat    2940
ccactattca gagcaaattc agcagtccc gattgggact tcaacacaaa caaggacaat    3000 tgccaatgg caaacaaggt aggagtggga ggcttcggtc cagggttcac accccccacac    3060 ggtggccttc tggggtggag ccctcaggca cagggcattc taacaacctc gccaccagat    3120
ccacctcctg cttccaccaa tcggaggtca ggaagaaagc caaccccagt ctctccacct    3180
ctaagggaca cacatccaca ggccatgcag tggaa    3215
```

<210> SEQ ID NO 49
<211> LENGTH: 47
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: N-term Myr
<220> FEATURE:
<223> OTHER INFORMATION: C-term NH2

-continued

<400> SEQUENCE: 49

```
Gly Leu Asn Gln Ser Thr Phe Asn Pro Leu Gly Phe Phe Pro Ser His
1               5                   10                  15

Gln Leu Asp Pro Leu Phe Lys Ala Asn Ala Gly Ser Ala Asp Trp Asp
            20                  25                  30

Lys Asn Pro Asn Lys Asp Pro Trp Pro Gln Ala His Asp Thr Ala
        35                  40                  45
```

COMPOSITIONS AND METHODS FOR TREATING METABOLIC DISEASES

CROSS-REFERENCE TO RELATED APPLICATIONS

This application is the U.S. national phase entry under 35 U.S.C. § 371 of PCT International Application No. PCT/CN2017/086558, filed May 31, 2017, which claims the benefit of priority of Chinese Application No. 201610370442.4, filed May 30, 2016. The contents of this application is incorporated herein by reference.

SEQUENCE LISTING

The instant application contains a Sequence Listing which has been submitted electronically in ASCII format and is hereby incorporated by reference in its entirety. Said ASCII copy is named Sequence Listing.txt and is 55 kilobytes in size.

This application contains a Sequence Listing which has been submitted electronically in ASCII format and is hereby incorporated by reference in its entirety. Said ASCII copy, created on Apr. 14, 2016, is named 13230.0001_SL.txt and is 56,034 bytes in size.

This disclosure relates to compositions and methods for treating a metabolic disease such as diabetes and hyperlipidemia. In certain embodiments, the disclosure relates to the treatment of a metabolic disease with a polypeptide derived from hepatitis B virus.

Metabolic diseases are caused by an imbalance of metabolites including carbohydrates, fats, lipids, and minerals that are crucial for well-being of a living organism. For example, type II diabetes and hyperlipidemia represent two most common metabolic diseases. The imbalance of metabolites may occur as a result of various factors including aging, behavior, genetics, and environmental influences, and often multiple factors in combination contribute the manifestation of the disease. Patients suffering from metabolic diseases may display a wide range of symptoms including, for example, hyperglycemia, hyperinsulinemia, hyperlipidemia, insulin resistance, and dysregulation of other metabolites such as amino acids and minerals. It is often difficult to identify the underlying cause of metabolic diseases, making them difficult to treat effectively. Furthermore, patients suffering from metabolic diseases may have a risk of developing serious complications associated with the diseases, such as hypertension, cardiovascular diseases, kidney damages, and nerve damages.

Due to the heterogeneity of these diseases, patients suffering from metabolic diseases may require a number of different medications, targeting multiple metabolic pathways in an attempt to address multiple symptoms simultaneously. For instance, one study showed that the type II diabetic patients surveyed in the study were taking an average of 8.4 different drug compounds per day (see, e.g., Bauer et al, Diabetic Medicine, 31:1078-85 (2014)). One of the reasons that the patients suffering from metabolic diseases have to take various different medicines is because those medicines are often specialized to address a particular symptom or pathway of the metabolic disease and thus are not capable of targeting other related symptoms. Unfortunately, taking multiple medicines can affect the life quality of the patients and ultimately worsen the course of disease progression. Indeed, as statistics show, type II diabetic patients experience difficulty adhering to their medication regimens partially because of the complexity of these regimens (see, e.g., Garcia-Pérez et al, Diabetes Therapy, 4:175-94 (2013)).

Furthermore, metabolic diseases often involves a complicated network of signaling pathways, and therefore targeting one particular pathway by one agent does not always lead to a therapeutically relevant effect in patients. For instance, cyclosporine A (CsA), an immunosuppressant drug widely used in organ transplantation to prevent rejection, has been shown to inhibit bile acid uptake and HBV entry into cultured hepatocytes mediated sodium taurocholate cotransporting polypeptide (NTCP), which is a $Na^+$-dependent bile acid transporter that transports bile acids from blood stream to hepatocytes (Watashi et al, Hpatology, 59:1726-37 (2014)). However, treatment with CsA can produce deleterious effects on glucose metabolism and impair insulin response (Dresner et al, Surgery, 106(2):163-69 (1989)). In addition, CsA can induce hyperlipidemia in patients by increasing the total cholesterol level, primarily due to an increase in the low-density lipoprotein (LDL) cholesterol level (Ballantyne et al., JAMA, 262(1):53-56 (1989)). Various other compounds have been shown to bind to NTCP, but they do not produce a uniform effect on NTCP as some of those compounds function as an inhibitor while others function as an enhancer (Kim et al, J. Pharmacol. Exp. Ther., 291(3):1204-09 (1999)). While most of those drugs have not been validated for their therapeutic outcomes in treating metabolic diseases to date, some enhancers of NTCP produce opposite effects on glucose or lipid metabolism (see, e.g., Beaudoin et al., Appl. Physiol. Nutr. Metab. 38(2):140-47 (2013); Thelle et al., N. Engl. J. Med. 308(24):1454-57 (1983); Phillips et al., Br. Med. J. 292:1319-21 (1986); Boden et al., Circulation, 85(6):2039-44 (1992)). It is also unclear whether regulating NTCP in vivo would result in any therapeutically relevant effect, because subjects with NTCP deficiency did not exhibit any clear clinical phenotype (see Vaz et al, Hepatology, 61(1):260-267 (2015)). Thus, there is an urgent need to develop a new medication for metabolic diseases, potentially capable of addressing multiple symptoms simultaneously with a potent therapeutic efficacy.

HBV viral envelope contains three surface antigen proteins: large (L), medium (M), and small (S). These proteins are coded by a single open reading frame on the S gene, starting from three different translation initiating sites, i.e., L (Pre-S+Pre-S2+S), M (Pre-S2+S), and S (S). The HBV is divided into four major serotypes (adr, adw, ayr, ayw) based on antigenic epitopes present on its envelope proteins, and into eight genotypes (A-H) according to overall nucleotide sequence variation of the genome. During viral infection, the Pre-S1 region on the L protein of HBV was shown to bind to NTCP (Yan et al, eLife, 1:e00049 (2012)).

This disclosure provides compositions and methods for treating a metabolic disease with a polypeptide derived from HBV. In some embodiments, the polypeptides described herein include polypeptides derived from the pre-S region of any one of HBV genotypes A, B, C, D, E, F, G, and H. The disclosure further provides HBV-derived polypeptides that are capable of altering metabolism such as glucose and lipid metabolism in a subject, including humans as well as pharmaceutically relevant animal models.

In some aspects, the disclosure provides a pharmaceutical composition comprising a polypeptide described herein, wherein when administered to a subject in need thereof, the pharmaceutical composition provides serum concentrations of the polypeptide that allow for bidirectional regulation of NTCP-mediated bile acid uptake in the subject.

In some aspects, the disclosure provides methods of treating a metabolic disease in a subject in need thereof, comprising administering to the subject a therapeutically effective amount of the polypeptide described herein or a pharmaceutical composition comprising the polypeptide such that the serum concentrations of the administered polypeptide allow for bidirectional regulation of NTCP-mediated bile acid uptake in the subject, wherein the polypeptide comprises an amino acid sequence derived from Hepatitis B virus (HBV).

In some aspects, the disclosure relates to methods of lowering a serum lipid level in a subject in need thereof by administering to the subject a therapeutically effective amount of the polypeptide described herein or of a pharmaceutical composition comprising the polypeptide such that the serum concentrations of the administered polypeptide allow for bidirectional regulation of NTCP-mediated bile acid uptake in the subject. In some embodiments, the serum lipid may include, e.g., total cholesterol ("TC"), triglyceride ("TG"), and LDL-C.

In certain aspects, the disclosure also relates to methods of lowering a blood glucose level in a subject in need thereof, comprising administering to the subject a therapeutically effective amount of the polypeptide described herein or a pharmaceutical composition comprising such polypeptide.

In some embodiments, when the serum concentration of the administered polypeptide in the subject is at or below 93 nmol/L, the polypeptide enhances NTCP-mediated bile acid uptake in the subject. In some embodiments, when the serum concentration of the administered polypeptide in the subject is above 93 nmol/L, the polypeptide inhibits NTCP-mediated bile acid uptake in the subject. In some embodiments, the serum concentration of the polypeptide in the subject reaches a peak concentration (i.e., $C_{max}$) at about 20 minutes after the administration. Thus, in some embodiments, $T_{max}$ of the polypeptide described herein is about 20 minutes. In some embodiments, the peak concentration is more than 93 nmol/L.

In some embodiments, a subject administered with the polypeptide described herein suffers from or is at risk of developing a metabolic disease. In some embodiments, the metabolic disease involves dysregulation of lipid metabolism. In some embodiments, the metabolic disease is a cholesterol-related disorder. In some embodiments, the metabolic disease is hyperlipidemia (e.g., hypertriglyceridemia, hypercholesterolemia, or a combination thereof). In some embodiments, the metabolic disease involves dysregulation of glucose metabolism. In some embodiments, the metabolic disease is hyperglycemia. In some embodiments, the metabolic disease is diabetes or obesity. In some embodiments, the subject suffers from or is at risk of developing cardiovascular diseases (e.g., atherosclerotic diseases), heart diseases, or kidney impairment.

In some embodiments, the polypeptide described herein is capable of reducing or stabilizing the level or activity of one or more chemical or biological molecules associated with metabolism in the subject. The chemical or biological molecule associated with metabolism is chosen from glucose, cholesterol, triglyceride, free fatty acids, amino acids, hormones, LDL-C, HDL-C, HbA1c, blood urea nitrogen, and minerals. In some embodiments, the polypeptide described herein is also capable of reducing or stabilizing the level or value of one or more physiological parameters that measure metabolic changes. The physiological parameter is chosen from glycemia, blood pressure, body weight, fat mass, body mass index (BMI), inflammation, atherosclerosis index, heart index, kidney index, total fat index, and homeostatic model assessment (HOMA) index.

In some embodiments, the polypeptide described herein comprises an amino acid sequence derived from the pre-S region of HBV genotype A, B, C, D, E, F, G, or H. In certain embodiments, the polypeptide described herein comprises the sequence of amino acids 13-59 of the pre-S1 region of HBV genotype C. In additional embodiments, the polypeptide described herein comprises an amino acid sequence derived from the pre-S1 region of any other HBV genotype that corresponds to amino acids 13-59 of the pre-S1 region of HBV genotype C. In some embodiments, the polypeptide comprises an amino acid sequence selected from SEQ ID NOs: 21-40.

In some embodiments, one or more amino acid residues of the polypeptide described herein are deleted, substituted, or inserted while maintaining the ability to bind to NTCP and bidirectionally regulate NTCP-mediated transport of bile acid into hepatocytes. In certain embodiments, the polypeptide described herein comprises a native flanking amino acid sequence from the pre-S1 region of HBV genotype A, B, C, D, E, F, G, or H. In other embodiments, the polypeptide described herein has at least about 30%, 40%, 50%, 60%, 70%, 80%, 85%, 90%, 95%, 96%, 97%, 98%, or 99% identity to any one of the amino acid sequences selected from SEQ ID NOs: 21-40. In some embodiments, the polypeptide comprises the glycine corresponding to amino acid 13 of the pre-S1 region of HBV genotype C and/or the asparagine corresponding to amino acid 20 of the pre-S1 region of HBV genotype C.

In some embodiments, the polypeptide described herein comprises an N-terminal modification with a hydrophobic group and/or a C-terminal modification that is capable of stabilizing the polypeptide. The hydrophobic group may be chosen from, e.g., myristic acid, palmitic acid, stearic acid, oleic acid, linoleic acid, cholesterol, and arachidonic acid. The C-terminal modification may be chosen from, e.g., amidation (amination), isopentanediolization, and any C-terminal modification that is capable of stabilizing the polypeptide. In certain embodiments, the polypeptide described herein comprises an N-terminal modification with myristic acid and/or a C-terminal modification with amination. In some embodiments, the polypeptide described herein comprises an amino acid sequence chosen from SEQ ID NOs: 21-40. In some embodiments, the polypeptide described herein comprises the amino acid sequence of SEQ ID NO: 23.

In one aspect, the polypeptide described herein is capable of reducing one or more symptoms associated with the metabolic disease. In some embodiments, the polypeptide described herein or the pharmaceutical composition comprising such polypeptide is administered to the subject before, concurrently with, or after the administration of a therapeutically effective amount of at least one a second agent. The second agent may be chosen from, e.g., an antihyperlipidemic agent, an antihyperglycemic agent, an antidiabetic agent, an antiobesity agent, and a bile acid analogue. For example, the second agent may be chosen from, e.g., insulin, metformin, sitagliptin, colesevelam, glipizide, simvastatin, atorvastatin, ezetimibe, fenofibrate, nicotinic acid, orlistat, lorcaserin, phentermine, topiramate, obeticholic acid, and ursodeoxycholic acid.

In some embodiments, the polypeptide described herein or the pharmaceutical composition comprising such polypeptide is administered to the subject by at least one mode including, e.g., parenteral, intrapulmonary, intranasal, intralesional, intramuscular, intravenous, intraarterial, intraperitoneal, and subcutaneous administration. In some embodiments, the polypeptide described herein or the pharmaceutical composition comprising such polypeptide is administered to the subject subcutaneously.

DETAILED DESCRIPTION

Figure 1:
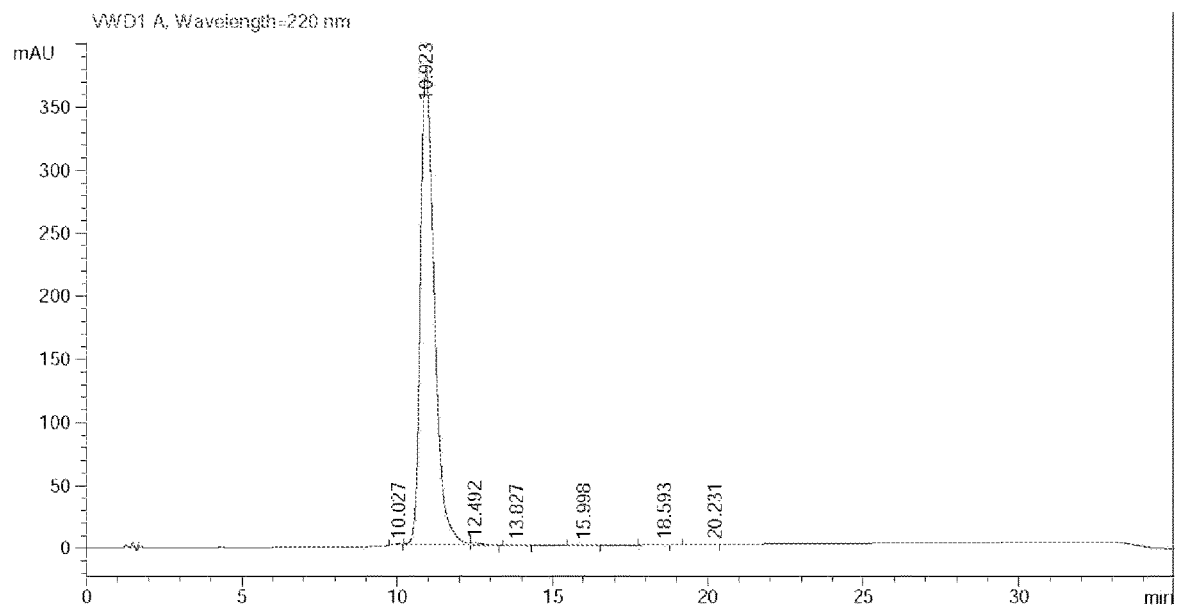
FIG. 1A shows an exemplary graph depicting the purity of Cmyr-47 as measured by high pressure liquid chromatography (HPLC).
FIG. 1B shows an exemplary graph depicting the molecular weight of Cmyr-47 as confirmed by Mass Spectrometry.
Figure 1:
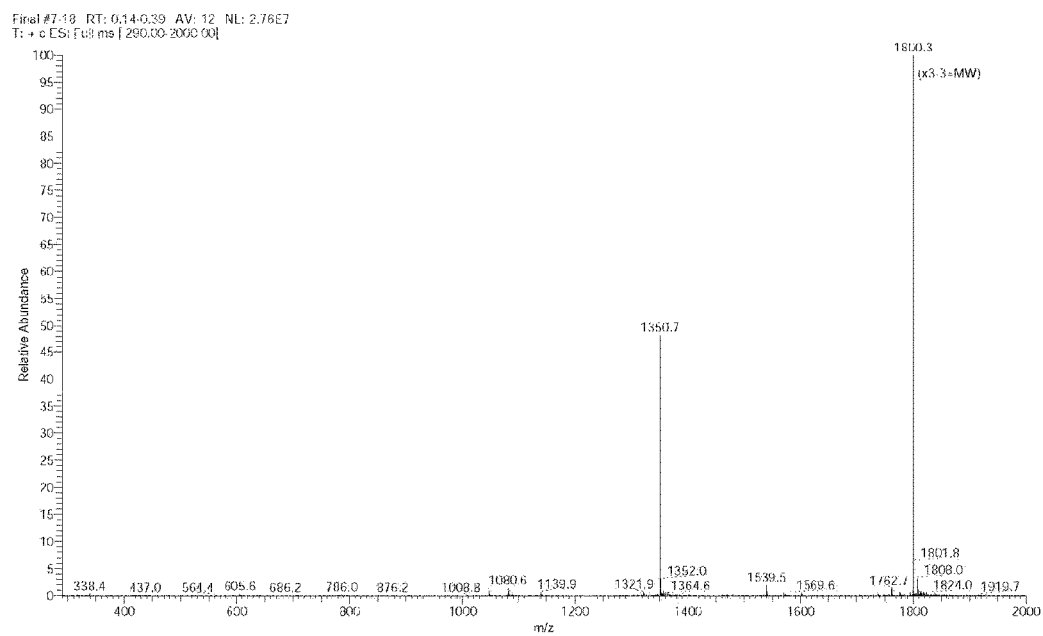

Unless defined otherwise, all technical and scientific terms used herein have the same meaning as commonly understood by those of ordinary skill in the art to which the disclosure belongs. For the purposes of the present disclosure, the following terms are defined below.

The articles "a" and "an" refer to one or to more than one (i.e., to at least one) of the grammatical object of the article. For example, "an element" means one element or more than one element.

The term "or" means, and is used interchangeably with, the term "and/or," unless context clearly indicates otherwise.

To the extent that the term "contain," "include," "have," or grammatical variants of such term are used in either the disclosure or the claims, such term is inclusive in a manner similar to the term "comprising" as "comprising" is interpreted when employed as a transitional word in a claim. The term "including" or its grammatical variants mean, and are used interchangeably with, the phrase "including but not limited to."

The term "about" means a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight or length. When the term "about" is used in conjunction with a numerical range, it modifies that range by extending the boundaries above and below the numerical values set forth. In general, the term "about" is intended to modify a numerical value above and below the stated value by a variance of ≤10%.

I. Polypeptides

Certain aspects of the present disclosure provide polypeptides derived from HBV for treating a metabolic disease including, e.g., diabetes and hyperlipidemia. The polypeptides may be derived from the pre-S1 region of HBV and may be capable of binding to NTCP in vitro, such as, e.g., in a solution or a cell-free system (e.g., a cell lysate or in a reconstituted system), or in a cell, such as, e.g., ex vivo in a cell in culture (e.g., a cell expressing NTCP, or a hepatocyte), or in vivo in a cell within a subject. The subject may be a mammal. In some embodiments, the subject may be a human.

The terms "polypeptide," "peptide," and "protein" are used interchangeably and encompass full-length proteins and fragments, as well as variants of the full-length proteins and the fragments. Such fragments and variants of the polypeptide described herein retain at least the biological activities of the polypeptide to bind to NTCP and bidirectionally regulate NTCP-mediated transport of bile acid into hepatocytes. The "polypeptide," "peptide," and "protein" can include natural and/or non-natural amino acid residues. Those terms also include post-translationally modified proteins, including, e.g., glycosylated, sialylated, acetylated, and/or phosphorylated proteins. The terms also include chemically modified proteins at one or more amino acid residues, such as, e.g., at the N-terminus and/or at the C-terminus. For instance, the N-terminus of the polypeptide disclosed herein can be modified by a hydrophobic group such as, e.g., myristic acid, palmitic acid, stearic acid, oleic acid, linoleic acid, cholesterol, and arachidonic acid. In some embodiments, the C-terminus of the polypeptide disclosed herein can be modified to stabilize the polypeptide. The C-terminus modification may be chosen from amidation (amination), isopentanediolization, and any other C-terminal modification capable of stabilizing the polypeptide.

As used herein, the term "polypeptide derived from HBV" or "HBV-derived polypeptide" refers to the origin or source of the polypeptide as being from HBV, and may include native, recombinant, synthesized, or purified polypeptides. The term "polypeptide derived from HBV" or "HBV-derived polypeptide" refers to a full-length native HBV polypeptide or fragments thereof, as well as variants of the full-length native polypeptide or its fragments. In some embodiments, the fragment may consist of at least 3-5 amino acids, at least 5-10 amino acids, at least 10-20 amino acids, at least 20-30 amino acids, at least 30-50 amino acids, or the entire amino acids of the native sequence, or may be otherwise identifiable to one of ordinary skill in the art as having its origin in the native sequence. In some embodiments, the polypeptide described herein may be derived from the pre-S1 region of the L protein of any HBV subtype. In some embodiment, the polypeptide described herein may comprise the entire pre-S1 region of the L protein of any HBV subtype. In certain embodiments, the polypeptide described herein may be derived from the pre-S1 region of the L protein of any one of HBV genotypes A, B, C, D, E, F, G, and H. The genomic sequences of these HBV genotypes can be found in GenBank Accession Nos. KC875260 (SEQ ID NO: 41), AY220704 (SEQ ID NO: 42), AF461363 (SEQ ID NO: 43), AY796030 (SEQ ID NO: 44), AB205129 (SEQ ID NO: 45), DQ823095 (SEQ ID NO: 46), HE981176 (SEQ ID NO: 47), and AB179747 (SEQ ID NO: 48), respectively. In certain embodiments, the polypeptide described herein may be derived from the pre-S1 region of the L protein of HBV genotype C. The polypeptide derived from HBV described herein retains one or more biological activities described herein of the corresponding native HBV polypeptide, including at least the biological activities of the polypeptide to bind to NTCP and bidirectionally regulate NTCP-mediated transport of bile acid into hepatocytes.

"Variant" as used herein in connection with the polypeptide described herein, a polypeptide derived from HBV, or an HBV-derived polypeptide means a polypeptide that differs from a given polypeptide (i.e., the polypeptide described herein, the polypeptide derived from HBV, or the HBV-derived polypeptide) in amino acid sequence, but retains one or more biological activities described herein of the given polypeptide. The variant polypeptide described herein retains at least at least the biological activities of the polypeptide to bind to NTCP and bidirectionally regulate NTCP-mediated transport of bile acid into hepatocytes. The variant polypeptide described herein may have one or more amino acid additions (e.g., insertion), deletions, or substitutions from the given polypeptide. In some embodiments, the variant polypeptide described herein may have 1-30, 1-20, 1-10, 1-8, 1-5, or 1-3 amino acid additions (e.g., insertion), deletions, or substitutions from the given polypeptide, including all integers in between these ranges. For example, the polypeptide sequence may contain conservative substitution of amino acids. A conservative substitution of an amino acid, i.e., replacing an amino acid with a different amino acid of similar properties (e.g., hydrophilicity and degree and distribution of charged regions), typically involves a minor change and therefore does not significantly alter the biological activity of the polypeptide. These minor changes can be identified, in part, by considering the hydropathic index of amino acids based on a consideration of the hydrophobicity and charge of the amino acid. Amino acids of similar hydropathic indexes and hydrophilicity values can be substituted and still retain protein function. Both the hydrophobicity index and the hydrophilicity value of amino acids are influenced by the particular side chain of that amino acid. Consistent with that observation, amino acid substitutions that are compatible with biological function depend on the relative similarity of the amino acids, and particularly the side chains of those amino acids, as revealed by the hydrophobicity, hydrophilicity, charge, size, and other properties.

The term "variant" also includes a polypeptide that has certain identity, such as, e.g., at least about 30%, 40%, 50%, 60%, 70%, 80%, 85%, 90%, 95%, 96%, 97%, 98%, or 99% identity to the given polypeptide. "Variant" as used herein also includes a polypeptide comprising the portion of the given polypeptide that corresponds to a native sequence of HBV proteins. "Variant" may also refer to a fusion protein or chimeric protein, comprising polypeptides derived from two or more different sources. Non-limiting examples of the fusion protein described herein may include, e.g., a fusion protein of one polypeptide derived from HBV and another polypeptide derived from a non-HBV protein, a fusion protein of two polypeptides derived from different HBV subtypes, and a fusion protein of two polypeptides derived from different regions of the L protein of any one of HBV subtypes, or from different sequences within the pre-S1 region of the L protein of any one of HBV subtypes.

The term "variant" also includes a polypeptide that comprises the same amino acid sequence of a given polypeptide (i.e., the polypeptide described herein, the polypeptide derived from HBV, or the HBV-derived polypeptide) and retains one or more biological activities of the given polypeptide, but chemically and/or post-translationally modified in a manner different from the given polypeptide. "Variant" can also be used to describe a polypeptide or a fragment thereof that has been differentially processed, such as by proteolysis, phosphorylation, or other post-translational modification, yet retains its biological activity of binding to NTCP and bidirectionally regulating NTCP-mediated transport of bile acid into hepatocytes. Use of "variant" herein is intended to encompass fragments of a variant unless otherwise contradicted by context. The term "variant" also encompasses the homologous polypeptide sequences found in the different viral species, strains, or subtypes of the hepadnavirus genus. HBV is divided into four major serotypes (adr, adw, ayr, ayw) based on antigenic epitopes present on its envelope proteins, and into eight genotypes (A-H) according to overall nucleotide sequence variation of the genome. The term "variant" therefore includes homologous polypeptides found in any of these HBV subtypes. "Variant" can also include polypeptides having native flanking amino acid sequences from any of these HBV subtypes added to the N and/or C terminus.

The terms "conservative amino acid substitutions" and "conservative substitutions" are used interchangeably herein to refer to intended amino acid swaps within a group of amino acids wherein an amino acid is exchanged with a different amino acid of similar size, structure, charge, and/or polarity. Families of amino acid residues having similar side chains are known in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, in some embodiments, an amino acid residue in a polypeptide can be replaced with another amino acid residue from the same side chain family. In other embodiments, a string of amino acids can be replaced with a structurally similar string that differs in order and/or composition of side chain family members. In yet other embodiments, mutations can be introduced randomly along all or part of the polypeptide. Examples of conservative amino acid substitutions include, e.g., exchange of one of the aliphatic or hydrophobic amino acids Ala, Val, Leu, and Ile for one of the other amino acids in that group of four; exchange between the hydroxyl-containing residues Ser and Thr; exchange between the acidic residues Asp and Glu; exchange between the amide residues Asn and Gln; exchange between the basic residues Lys, Arg, and His; exchange between the aromatic residues Phe, Tyr, and Trp; and exchange between the small-sized amino acids Ala, Ser, Thr, Met, and Gly. Conservative substitutions, such as substituting a conserved amino acid with a similar, structurally related amino acid would not be reasonably expected to impose a substantial influence on the biological activity of the polypeptide.

The term "sequence identity" (e.g., a "sequence 50% identical to") refers to the extent that a sequence is identical on an amino acid-by-amino acid basis over a window of comparison. In some embodiments, the polypeptide described herein may comprise an amino acid sequence at least about 30%, 40%, 50%, 60%, 70%, 80%, 85%, 90%, 95%, 96%, 97%, 98%, or 99% identical to the sequence of a given polypeptide and still retain one or more biological activities of the given polypeptide. A "percentage identity" (or "% identity") may be calculated by comparing two optimally aligned sequences over the window of comparison, determining the number of positions at which the identical amino acids occur in both sequences to yield the number of matched positions, dividing the number of matched positions by the total number of positions in the window of comparison, and multiplying the result by 100 to yield the percentage of sequence identity. Optimal alignment of sequences for aligning a comparison window may be conducted by computerized implementations of algorithms available in the art, such as, e.g., the BLAST® family of programs, or by visual inspection and the best alignment (i.e., resulting in the highest percentage homology over the comparison window) generated by any of the various methods selected. For sequence comparison, one sequence acts as a reference sequence, to which test sequences are compared. When using a sequence comparison algorithm, test and reference sequences are input into a computer, subsequence coordinates may be designed, if necessary, and sequence algorithm program parameters are designated. The sequence comparison algorithm then calculates the present sequence identity for the test sequences relative to the reference sequence, based on the designated program parameters. The designation of sequence algorithm program parameters is well within the knowledge in the art. For example, the window of comparison may be designated as over the entire length of either or both comparison sequences, such as, e.g., over the entire length of the reference sequence, and gaps of up to 5% of the total number of amino acids in the reference sequence may be allowed.

As used herein, the "biological activity" of the polypeptides described herein encompasses the ability of the polypeptides to bind to NTCP and bidirectionally regulate NTCP-mediated bile acid uptake in hepatocytes. As used herein, "bidirectional regulation" of a molecule or pathway means that the HBV-derived polypeptides described herein enhances the activity of the molecule or pathway (i.e., functions as an enhancer) at or below a certain concentration, and inhibits the activity of the molecule or pathway (i.e., functions as an inhibitor) above the concentration. For instance, the polypeptide described herein may bind to NTCP and promote NTCP-mediated bile acid uptake in hepatocytes (i.e., functions as an "enhancer" of NTCP) at or below a certain concentration. The same polypeptide may also bind to NTCP but inhibit NTCP-mediated bile acid uptake (i.e., functions as an "inhibitor" of NTCP) above that concentration. In some embodiments, the polypeptide described herein may function as an enhancer of NTCP at or below 93 nmol/L and as an inhibitor of NTCP above 93 nmol/L. For example, the Cmyr-47 polypeptide described herein may function as an enhancer of NTCP at or below 500 ng/ml and as an inhibitor of NTCP above 500 ng/ml.

In some embodiments, the polypeptide described herein may bidirectionally regulate NTCP-mediated uptake of bile acids into hepatocytes in vitro. The polypeptide described herein may promote in vitro NTCP-mediated bile acid uptake at or below a certain concentration, while the polypeptide may inhibit in vitro NTCP-mediated bile acid uptake above that concentration. In some embodiment, the polypeptide described herein may promote in vitro NTCP-mediated bile acid uptake at or below 93 nmol/L, while the polypeptide may inhibit in vitro NTCP-mediated bile acid uptake above 93 nmol/L. For example, the Cmyr-47 polypeptide described herein may promote in vitro NTCP-mediated bile acid uptake at or below 500 ng/ml and inhibit in vitro NTCP-mediated bile acid uptake above 500 ng/ml.

In some embodiments, the polypeptide described herein may promote NTCP-mediated bile acid uptake in a subject treated with the polypeptide at or below a certain serum concentration of the administered polypeptide. The polypeptide may inhibit NTCP-mediated bile acid uptake in a subject treated with the polypeptide above that serum concentration of the administered polypeptide. In some embodiments, when the serum concentration of the polypeptide described herein is at or below 93 nmol/L in a subject treated with the polypeptide, the polypeptide is capable of enhancing NTCP-mediated uptake of bile acids in the subject. In some embodiments, when the serum concentration of the polypeptide described herein is above 93 nmol/L in a subject treated with the polypeptide, the polypeptide is capable of inhibiting NTCP-mediated uptake of bile acids in the subject. For example, the Cmyr-47 polypeptide described herein may be capable of enhancing NTCP-mediated uptake of bile acids in the subject at or below a serum concentration of 500 ng/ml, and inhibiting NTCP-mediated uptake of bile acids in the subject above a serum concentration of 500 ng/ml.

The biological activity of the polypeptide described herein may also include the ability to treat a metabolic disease or to ameliorate one or more symptoms associated with the metabolic disease. The biological activity may further include the ability of the polypeptide described herein to prevent the development of a metabolic disease. In some embodiments, the biological activity of the polypeptide described herein may include the ability of the polypeptide to modulate the level or activity of one or more chemical or biological molecules associated with metabolism, and/or to modulate the level or value of one or more physiological parameters that measure metabolic changes. In some embodiments, the "biological activity" of the polypeptide described herein includes the ability of the polypeptide to reduce or stabilize the level or activity of one or more such chemical or biological molecules or physiological parameters. In some embodiments, metabolism refers to bile acid metabolism, glucose metabolism, lipid metabolism, and/or amino acid metabolism. The chemical or biological molecules associated with metabolism may include, e.g., glucose, triglyceride, cholesterol, free fatty acids, bile acids, amino acids, hormones, such as, e.g., insulin, LDL-C, HDL-C, HbA1c, blood urea nitrogen, and minerals. The physiological parameters that measure metabolic changes may include, e.g., glycemia, blood pressure, body weight, fat mass, body mass index (BMI), inflammation, atherosclerosis index (AI), heart index, kidney index, total fat index, and homeostatic model assessment (HOMA) index.

In certain embodiments, the "biological activity" of the polypeptide described herein includes the ability of the polypeptide to increase the level of serum bile acid in a subject. In certain embodiments, the "biological activity" of the polypeptide described herein includes the ability of the polypeptide to enhance cholesterol elimination through bile acid synthesis in hepatocytes.

In some embodiments, the biological activity of the polypeptide described herein may include the ability to lower the serum level of one or more chemical or biological molecules associated with lipid metabolism in a subject administered with the polypeptide. In some embodiments, the biological activity of the polypeptides described herein may include the ability to lower the serum level of serum lipids, such as, e.g., triglyceride, total cholesterol, or LDL-C in a subject administered with the polypeptide.

In some embodiments, the biological activity of the polypeptide described herein may include the ability to lower the serum level of one or more chemical or biological molecules associated with glucose metabolism in a subject administered with the polypeptide. In some embodiments, the biological activity of the polypeptides described herein may include the ability to lower the serum level of glucose or HbA1c in a subject administered with the polypeptide. In some embodiments, the polypeptides described herein may be capable of stabilizing the serum level of insulin in a subject.

In certain embodiments, the "biological activity" of the polypeptide described herein includes the ability of the polypeptide to treat a metabolic disorder in a subject. In some embodiments, the metabolic disorder involves dysregulation of lipid metabolism. The metabolic disease may include a cholesterol-related disorder, such as, e.g., hyperlipidemia (including hypertriglyceridemia, hypercholesterolemia, or both). In some embodiments, the metabolic disorder involves dysregulation of glucose metabolism. The metabolic disease may include, e.g., diabetes and obesity.

In certain embodiments, the "biological activity" of the polypeptide described herein includes the ability of the polypeptide to ameliorate or prevent one or more symptoms or complications of such disorders. In certain embodiments, the "biological activity" of the polypeptide described herein includes the ability of the polypeptide to mitigate the negative impact of such disorders on the health of a patient or reduce the risk of developing such disorders. In certain embodiments, the "biological activity" of the polypeptide described herein also includes the ability of the polypeptide to reduce the severity of or the risk of developing other associated diseases, such as, e.g., atherosclerosis and/or cardiovascular diseases, heart diseases, kidney impairment, or obesity.

Without being bound by theory, it is believed that these biological activities of the polypeptide described herein may result from bidirectional regulation of NTCP-mediated bile acid uptake in the subject by the polypeptide at the serum concentrations following administration of the polypeptide to the subject. In some embodiments, when the concentration of the polypeptide described herein in the blood stream of a subject administered with such polypeptide is at or below a certain concentration, bile acid uptake in the subject is enhanced. In some embodiments, when the concentration of the polypeptide described herein in the blood stream of the subject is above a certain concentration, bile acid uptake in the subject is inhibited. In some embodiments, when the concentration of the polypeptide described herein in the blood stream of a subject administered with such polypeptide is at or below 93 nmol/L, bile acid uptake in the subject is enhanced. In some embodiments, when the concentration of the polypeptide described herein in the blood stream of the subject is above 93 nmol/L, bile acid uptake in the subject is inhibited. For example, when the concentration of the Cmyr-47 polypeptide described herein in the blood stream of a subject administered with such polypeptide is at or below 500 ng/ml, bile acid uptake in the subject is enhanced. When the concentration of the Cmyr-47 polypeptide described herein in the blood stream of the subject is above 500 ng/ml, bile acid uptake in the subject is inhibited.

Various in vivo, in vitro, and ex vivo assays to confirm the biological activity of the polypeptide described herein are contemplated. The biological activity of the polypeptide described herein may be confirmed in vivo, by collecting a sample from a subject treated with the polypeptide described herein. The sample may be a biopsy sample collected from a specific tissue such as, e.g., liver, muscle, fat, and pancreas, or a snap-frozen tissue collected from an animal post-mortem. In some embodiments, the sample may be a serum sample collected from blood drawn from a subject. Various methods for collecting a serum sample from a subject are known in the art, and include, e.g., tail-bleeding, retro-orbital puncture, and cardiopuncture. In some embodiments, the biological activity of the polypeptide described herein may be confirmed in vitro, by contacting the polypeptide described herein with a cell that is either a transformed cell line or a cell isolated from an animal. In some embodiments, the cell may be a primary hepatocyte isolated from an animal.

Various methods can be used to confirm the ability of the polypeptide described herein to bidirectionally regulate NTCP in a quantitative manner. For instance, cells expressing NTCP (e.g., mammalian cells overexpressing NTCP or hepatocytes) may be treated in vitro with bile acids and increasing amounts of the polypeptide described herein. Bile acids added to the cells may be radiolabeled or chemically labeled for detection. The cells may be then harvested and the amount of bile acids taken up by the cells may be measured. The ability of the polypeptide described herein to bidirectionally regulate NTCP may be confirmed when the polypeptide enhances bile acid uptake at or below a certain concentration while inhibits bile acid uptake above that concentration.

The exemplary assays useful to confirm the biological activity of the polypeptide may also include a functional analysis with a sample collected from a subject treated with the polypeptide described herein, including, e.g., glucose production assay, glucose uptake assay, fatty acid oxidation assay, cholesterol assay, bile acids assay, urea assay, and triglyceride assay. In some embodiments, the assays may also include, e.g., a binding analysis between the polypeptide and NTCP, an activity assay of NTCP for transporting bile acids, and an expression, localization, or activity analysis of molecular factors involved in metabolism, such as, e.g., bile acid metabolism, glucose metabolism, lipid metabolism, and amino acid metabolism. The foregoing techniques and procedures to confirm the biological activity of the polypeptides described herein may be performed by following methods known in the art and procedures provided in this specification.

In some embodiments, the polypeptide described herein may comprise an amino acid sequence of the pre-S1 region of any HBV subtype. In some embodiments, the polypeptide described herein comprises the sequence of amino acids 13-59 of the pre-S1 region of HBV genotype C: GTNLSVPNPLGFFPDHQLDPAFGANS-NNPDWDFNPNKDHWPEANQVG (SEQ ID NO: 23). In additional embodiments, the polypeptide described herein may comprise the corresponding pre-S sequence from another HBV genotype, such as, e.g., any one of genotypes A, B, D, E, F, G, and H. For example, in some embodiments, the polypeptide described herein may comprise:

```
pre-S1 amino acids 13-59 of HBV genotype A:
                                  (SEQ ID NO: 34)
GTNLSVPNPLGFFPDHQLDPAFGANSNNPDWDFNPVKDDWPAANQVG, pre-S1 amino acids 13-59 of HBV genotype B:
                                  (SEQ ID NO: 35)
GTNLSVPNPLGFFPDHQLDPAFKANSENPDWDLNPNKDNWPDANKVG, pre-S1 amino acids 2-48 of the HBV genotype D:
                                  (SEQ ID NO: 36)
GQNLSTSNPLGFFPDHQLDPAFRANTANPDWDFNPNKDTWPDANKVG, pre-S1 amino acids 12-58 of the HBV genotype E:
                                  (SEQ ID NO: 37)
GKNISTTNPLGFFPDHQLDPAFRANTRNPDWDHNPNKDHWTEANKVG, pre-S1 amino acids 13-59 of the HBV genotype F:
                                  (SEQ ID NO: 38)
GQNLSVPNPLGFFPDHQLDPLFRANSSSPDWDFNTNKDSWPMANKVG, pre-S1 amino acids 12-58 of the HBV genotype G:
                                  (SEQ ID NO: 39)
GKNLSASNPLGFLPDHQLDPAFRANTNNPDWDFNPKKDPWPEANKVG,
or pre-S1 amino acids 13-59 of the HBV genotype H:
                                  (SEQ ID NO: 40)
GQNLSVPNPLGFFPDHQLDPLFRANSSSPDWDFNTNKDNWPMANKVG.
```

In some embodiments, the polypeptide described herein may comprise a portion of the pre-S1 region of HBV, said portion comprising at least an amino acid sequence chosen from SEQ ID NOs: 23 and 34-40. In some embodiments, the polypeptide described herein may comprise the entire pre-S1 region of HBV.

In some embodiments, the polypeptide described herein may be 10-100 amino acids in length. For example, the polypeptide may be 15-100, 15-80, 20-100, 20-80, 20-60, 25-60, 30-60, 35-60, or 40-60 amino acids in length, including all integers in between these ranges. In some embodiments, the polypeptide described herein may be at least 20, such as, e.g., at least 25, 30, 35, 40, amino acids in length. In some embodiments, the polypeptide described herein may be 20, 25, 30, 35, 40, 47, 55, 60 amino acids in length. In some embodiments, the polypeptide described herein may be 47 amino acids in length. The variants of the polypeptides described herein that differ in length retain one or more biological activities associated with the corresponding polypeptides, including at least the biological activity of binding to NTCP and bidirectionally regulating NTCP-mediated transport of bile acid into hepatocytes.

In some embodiments, the polypeptide described herein may comprise an N-terminal modification with a hydrophobic group. For example, the hydrophobic group may be chosen from myristic acid, palmitic acid, stearic acid, oleic acid, linoleic acid, cholesterol, and arachidonic acid. In some embodiments, the hydrophobic group may be chosen from myristic acid, palmitic acid, stearic acid, and cholesterol. In some embodiments, the hydrophobic group may be myristic acid. In certain embodiments, the polypeptide described herein may comprise an amino acid sequence chosen from SEQ ID NOs: 23 and 34-40, wherein the N terminus may be modified with a hydrophobic group chosen from myristic acid, palmitic acid, stearic acid, and cholesterol. In certain embodiments, the polypeptide described herein may comprise an amino acid sequence chosen from SEQ ID NOs: 23 and 34-40, wherein the N terminus may be myristoylated. In some embodiments, the polypeptide described herein may comprise the amino acid sequence of SEQ ID NO: 23, wherein the N terminus may be myristoylated. In some embodiments, the polypeptide described herein may comprise a C-terminal modification to stabilize the polypeptide. For example, the C-terminal modification may be chosen from amidation (amination), isopentanediolization, and any other C-terminal modification capable of stabilizing the polypeptide described herein. In some embodiments, the C-terminal modification may be amidation (amination). For example, the polypeptide described herein may comprise the amino acid sequence of NO: 23, wherein the N terminus may be myristoylated, and/or the C terminus may be amidated (aminated). In some embodiments, the polypeptide described herein may comprise the amino acid sequence of NO: 3 (Cmyr-47). In some embodiments, the polypeptide described herein may comprise an amino acid sequence chosen from SEQ ID NOs: 34-40, wherein the N terminus may be myristoylated, and/or the C terminus may be modified by amidated (aminated). In some embodiments, the polypeptide described herein may comprise an amino acid sequence chosen from SEQ ID NOs: 14-20. The variants of the polypeptide described herein that are modified at the N-terminus and/or the C-terminus retain one or more biological activities of the corresponding polypeptides that are not modified in the same manner, including at least the biological activity of binding to NTCP and bidirectionally regulating NTCP-mediated transport of bile acid into hepatocytes.

Variants of the polypeptides described herein are also contemplated in the present disclosure, including variants with one or more amino acid deletions, substitutions, or insertions that retain one or more biological activities of the polypeptides, including at least the biological activity of binding to NTCP and bidirectionally regulating NTCP-mediated transport of bile acid into hepatocytes. The polypeptides described herein preferably retain the glycine corresponding to amino acid 13 of the pre-S1 region of HBV genotype C (i.e., the N-terminal glycine of SEQ ID NO: 23).

In some embodiments, the polypeptides described herein retain the asparagine corresponding to amino acid 20 of the pre-S1 region of HBV genotype C. In some embodiments, the polypeptide described herein may have one or more naturally-occurring mutations in the pre-S1 region of HBV. In some embodiments, the polypeptide described herein may have 1-30, such as, e.g., 1-20, 1-10, 1-8, 1-5, or 1-3, amino acid deletions, substitutions, or insertions relative to a sequence from the pre-S1 region of HBV, including all integers in between these ranges. In some embodiments, the polypeptide described herein may have 1-30, such as, e.g., 1-20, 1-10, 1-8, 1-5, or 1-3, amino acid deletions, substitutions, or insertions relative to an amino acid sequence chosen from SEQ ID NOs: 23 and 34-40, including all integers in between these ranges. In some embodiments, the polypeptide described herein may have 1-30, such as, e.g., 1-20, 1-10, 1-8, 1-5, or 1-3, amino acid deletions, substitutions, or insertions relative to the amino acid sequence of SEQ ID NO: 23, including all integers in between these ranges. In some embodiments, the polypeptide described herein may have 1-3 amino acid deletions, substitutions, or insertions from the amino acid sequence of SEQ ID NO: 23. In certain embodiments, the polypeptide described herein may have 1-30, such as, e.g., 1-20, 1-10, 1-8, 1-5, or 1-3, amino acid deletions or insertions at the C terminus of an amino acid sequence chosen from SEQ ID NOs: 23 and 34-40, including all integers in between these ranges. For example, the polypeptide described herein may comprise an amino acid sequence chosen from SEQ ID NOs: 21, 22, and 24-28. In some embodiments, the polypeptide described herein may comprise the amino acid sequence of any one of the polypeptides listed in Table 1. In some embodiments, the polypeptide described herein may be chosen from any one of the post-translationally modified polypeptides listed in Table 1.

TABLE 1

List of Exemplary Polypeptides

| SEQ ID No. | SEQ name | N-terminal Modification | Amino acid sequence 12345678901234567890123456789 0 | C-terminal Modification | SEQ origin |
|---|---|---|---|---|---|
| 1 | Cmyr-60 | Myr | GTNLSVPNPLGFFPDHQLDPAFGANSNNPD WDFNPNKDHWPFANQVGAGAFGPGFTPPHG | NH2 | Genotype C Pre-S1(13-72) |
| 2 | Cmyr-55 | Myr | GTNLSVPNPLGFFPDHQLDPAFGANSNNPD WDFNPNKDHWPEANQVGAGAFGPGF | NH2 | Genotype C Pre-S1(13-67) |
| 3 | Cmyr-47 | Myr | GTNLSVPNPLGFFPDHQLDPAFGANSNNPD WDFNPNKDHWPEANQVG | NH2 | Genotype C Pre-S1(13-59) |
| 4 | Cmyr-40 | Myr | GTNLSVPNPLGFFPDHQLDPAFGANSNNPD WDFNPNKDHW | NH2 | Genotype C Pre-S1(13-52) |
| 5 | Cmyr-35 | Myr | GTNLSVPNPLGFFPDHQLDPAFGANSNNPD WDFNP | NH2 | Genotype C Pre-S1(13-47) |
| 6 | Cmyr-30 | Myr | GTNLSVPNPLGFFPDHQLDPAFGANSNNPD | NH2 | Genotype C Pre-S1(13-42) |
| 7 | Cmyr-25 | Myr | GTNSVPNPLGFFPDHQLDPAFGAN | NH2 | Genotype C Pre-S1(13-37) |
| 8 | Cmyr-20 | Myr | GTNSVPNPLGETPDHQLDP | NH2 | Genotype C Pre-S1(13-32) |
| 9 | Cmyr-47+ (-10) | Myr | GGWSSKPRQGMGTNLSVPNPLGFFPDHQLD PAFGANSNNPDWDFNPNKDHWPEANQVG | NH2 | Genotype C Pre-S1(2-59) |

TABLE 1-continued

List of Exemplary Polypeptides

| SEQ ID No. | SEQ name | N-terminal Modification | Amino acid sequence 123456789012345678901234567890 | C-terminal Modification | SEQ origin |
|---|---|---|---|---|---|
| 10 | Cmyr-47+ (-9) | Myr | GLSWTVPLEGTNLSVPNPLGFFPDHQLDP AFGANSNNPDWDFNPNKDHWPEANQVG | NH2 | Genotype E or G Pre-S1(2-11) + Genotype C Pre-S1(13-59) |
| 11 | Cplam-47 | Plam | GTNLSVPNPLGFFPDHQLDPAFGANSNNPD WDFNPNKDHWPEANQVG | NH2 | Genotype C Pre-S1(13-59) |
| 12 | Cstea-47 | Stearoyl | GTNLSVPNPLGFFPDHQLDPAFGANSNNPD WDFNPNKDHWPEANQVG | NH2 | Genotype C Pre-S1(13-59) |
| 13 | Cchol-47 | Chol | GTNLSVPNPLGFFPDHQLDPAFGANSNNPD WDFNPNKDHWPEANQVG | NH2 | Genotype C Pre-S1(13-59) |
| 14 | Amyr-47 | Myr | GTNLSVPNPLGFFPDHQLDPAFGANSNNPD WDFNPVKDDWPAANQVG | NH2 | Genotype A Pre-S1(13-59) |
| 15 | Bmyr-47 | Myr | GTNLSVPNPLGFFPDHQLDPAFKANSENPD WDLNPNKDNWPDANKVG | NH2 | Genotype B Pre-S1(13-59) |
| 16 | Dmyr-47 | Myr | GQNLSTSNPLGFFPDHQLDPAFRANTANPD WDFNPNKDTWPDANKVG | NH2 | Genotype D Pre-S1(2-48) |
| 17 | Emyr-47 | Myr | GKNISTTNPLGFFPDHQLDPAFRANTRNPD WDHNPNKDHWTEANKVG | NH2 | Genotype E Pre-S1(12-58) |
| 18 | Fmyr-47 | Myr | GQNLSVPNPLGFFPDHQLDPLFPANSSSPD WDFNTNKDSWPKANKVG | NH2 | Genotype F Pre-S1(13-59) |
| 19 | Gmyr-47 | Myr | GKNLSASNPLGFLPDHQLDPAFRANTNNPD WDFNPKKDPWPEANKVG | NH2 | Genotype G Pre-S1(12-58) |
| 20 | Hmyr-47 | Myr | GQNLSVPNPLGFFPDHQLDPLFRANSSSPD WDFNTNKDNWPMANKVG | NH2 | Genotype H Pre-S1(13-59) |

In various embodiments, the polypeptide described herein may have at least about 30%, 40%, 50%, 60%, 70%, 80%, 85%, 90%, 95%, 96%, 97%, 98%, or 99% identity to any of the polypeptides described herein. For example, the polypeptide may comprise an amino acid sequence at least about 30%, 40%, 50%, 60%, 70%, 80%, 85%, 90%, 95%, 96%, 97%, 98%, or 99% identical to any one of SEQ ID NOs: 21-40. In some embodiments, the polypeptide may comprise an amino acid sequence at least about 30%, 40%, 50%, 60%, 70%, 80%, 85%, 90%, 95%, 96%, 97%, 98%, or 99% identical to any one of SEQ ID NOs: 23 and 34-40. In some embodiments, the polypeptide may comprise an amino acid sequence at least about 30%, 40%, 50%, 60%, 70%, 80%, 85%, 90%, 95%, 96%, 97%, 98%, or 99% identical to SEQ ID NO: 23. The variants having certain sequence identity to the polypeptides described herein retain one or more biological activities of the corresponding polypeptides, including at least the biological activity of binding to NTCP and bidirectionally regulating NTCP-mediated transport of bile acid into hepatocytes.

Aspects of the present disclosure also include variants of the polypeptides described herein having a native flanking amino acid sequence from the HBV L protein, such as, e.g., from the pre-S1 region of the L protein, added to the N and/or C terminus. The native flanking amino acid sequence refers to the native sequence flanking the N or C terminus of the polypeptide described herein in the pre-S1 region of the corresponding HBV genotype or any other HBV genotypes. In some embodiments, the polypeptide described herein may comprise an amino acid sequence chosen from SEQ ID NOs: 23 and 34-40, and a native flanking amino acid sequence at the N and/or C terminus derived from the pre-S1 region of any one of HBV genotypes A-H. In some embodiments, the native flanking amino acid sequence may be derived from the consensus sequence of an HBV strain with the GenBank Accession No. KC875260 (genotype A; SEQ ID NO: 41), AY220704 (genotype B; SEQ ID NO: 42), AF461363 (genotype C; SEQ ID NO: 43), AY796030 (genotype D; SEQ ID NO: 44), AB205129 (genotype E; SEQ ID NO: 45), DQ823095 (genotype F; SEQ ID NO: 46), HE981176 (genotype G; SEQ ID NO: 47), or AB179747 (genotype H; SEQ ID NO: 48). For example, the polypeptide described herein may comprise the amino acid sequence of SEQ ID NO: 23, and a native flanking amino acid sequence at the N and/or C terminus derived from the pre-S1 region of HBV genotype C. Alternatively, the polypeptide described herein may comprise the amino acid sequence of SEQ ID NO: 23, and a native flanking amino acid sequence at the N and/or C terminus derived from the pre-S region of any one of HBV genotypes A, B, D, E, F, G, and H. In some embodiments, the N and/or C terminus of the polypeptide described herein may independently comprise a native flanking amino acid sequence having a length of 1-10, such as, e.g., 1-8, 1-5, or 1-3 amino acids, including all integers in between these ranges. For example, the polypeptide described herein may comprise the amino acid sequence of SEQ ID NO: 23 and a native flanking amino acid sequence of 10 amino acids at the N terminus from the pre-S1 region of HBV genotype C. In other words, the polypeptide may comprise amino acids 2-59 of the pre-S1 region of HBV genotype C (SEQ ID NO: 29). As another example, the polypeptide described herein may comprise the amino acid sequence of SEQ ID NO: 23 and a native flanking amino acid sequence of 9 amino acids at the N terminus from the pre-S1 region of HBV genotype E or G. In other words, the polypeptide may comprise amino acids 13-59 of the pre-S1 region of HBV genotype C and amino acids 2-11 of the pre-S1 region of HBV genotype E or G (SEQ ID NO: 30). It will be appreciated that, any polypeptides described herein can have native flanking amino acid sequences of any length extended from the N and/or C terminus, and the resulting polypeptides retain one or more biological activities of the original polypeptides, including at least the biological activity of binding to NTCP and bidirectionally regulating NTCP-mediated transport of bile acid into hepatocytes.

In some embodiments, the polypeptides described herein are capable of bidirectionally regulating NTCP-mediated transport of bile acids into hepatocytes. When hepatocytes are in contact with the polypeptide described herein at or below a certain concentration, NTCP-mediated transport of bile acid into the hepatocytes may be enhanced as compared with hepatocytes that are not in contact with such polypeptide. When hepatocytes are in contact with the polypeptide described herein above the certain concentration, NTCP-mediated transport of bile acid into the hepatocytes may be inhibited as compared with hepatocytes that are not in contact with such polypeptide. In some embodiments, when hepatocytes are in contact with at or below 93 nmol/L of the polypeptide described herein, NTCP-mediated transport of bile acid into the hepatocytes may be enhanced as compared with hepatocytes that are not in contact with such polypeptide. In some embodiments, when hepatocytes are in contact with above 93 nmol/L of the polypeptide described herein, NTCP-mediated transport of bile acid into the hepatocytes may be inhibited as compared with hepatocytes that are not in contact with such polypeptide. For example, when hepatocytes are in contact with at or below 500 ng/ml of the Cmyr-47 polypeptide described herein, NTCP-mediated transport of bile acid into the hepatocytes may be enhanced as compared with hepatocytes that are not in contact with such polypeptide. In some embodiments, when hepatocytes are in contact with above 500 ng/ml of the Cmyr-47 polypeptide described herein, NTCP-mediated transport of bile acid into the hepatocytes may be inhibited as compared with hepatocytes that are not in contact with such polypeptide.

In some embodiments, the polypeptides described herein may be capable of modulating, such as, e.g., reducing or stabilizing, the level or activity of one or more chemical or biological molecules associated with metabolism in a subject. In some embodiments, metabolism may include, e.g., bile acid metabolism, glucose metabolism, lipid metabolism, or amino acid metabolism. In some embodiments, the chemical or biological molecule is chosen from glucose, triglyceride, cholesterol, free fatty acids, bile acids, amino acids, hormones, LDL-C, HDL-C, HbA1c, blood urea nitrogen, and minerals. In some embodiments, the polypeptides described herein may be capable of modulating, such as, e.g., reducing or stabilizing, the level or value of one or more physiological parameters that measure metabolic changes such as, e.g., glycemia, blood pressure, body weight, fat mass, body mass index (BMI), inflammation, atherosclerosis index (AI), heart index, kidney index, total fat index, and homeostatic model assessment (HOMA) index. In some embodiments, the polypeptides described herein may be capable of increasing the serum level of bile acids in a subject. In some embodiments, the polypeptides described herein may be capable of reducing the level of serum lipids in a subject. In some embodiments, the polypeptides described herein may be capable of reducing the serum level of total cholesterol in a subject. In further embodiments, the polypeptides described herein may be capable of reducing the serum level of LDL-cholesterol in a subject. In some embodiments, the polypeptides described herein may be capable of reducing the serum level of triglyceride in a subject. In some embodiments, the polypeptides described herein may be capable of reducing the serum level of glucose in a subject. In some embodiments, the polypeptides described herein may be capable of reducing the serum level of HbA1c in a subject. In some embodiments, the polypeptides described herein may be capable of stabilizing the serum level of insulin in a subject. In some embodiments, the subject may be a mammal. In some embodiments, the subject may be a human. In some embodiments, the subject may suffer from a metabolic disease or may be at risk of developing such disease.

As used herein, "modulate" or "alter," all used interchangeably, includes "reducing," "decreasing," "lowering," "down-regulating," or "inhibiting" one or more quantifiable parameters optionally by a defined and/or statistically significant amount. The term "modulate" also includes "enhancing," "increasing," "elevating," "up-regulating," or "promoting" one or more quantifiable parameters optionally by a defined and/or statistically significant amount.

The terms "reduce," "decrease," "lower," "down-regulate," and "inhibit," all used interchangeably herein, mean that the level or activity of one or more chemical or biological molecules associated with metabolism such as, e.g., glucose, triglyceride, cholesterol, free fatty acids, bile acids, amino acids, or hormones, including, e.g., insulin, LDL-C, HDL-C, HbA1c, blood urea nitrogen, and minerals, is reduced below the level or activity observed in the absence of the polypeptides described herein or lower than a control polypeptide. In some embodiments, "reduce" may mean that the level or value of one or more physiological parameters that measure metabolic changes, such as, e.g., glycemia, blood pressure, body weight, fat mass, body mass index (BMI), inflammation, atherosclerosis index (AI), heart index, kidney index, total fat index, and homeostatic model assessment (HOMA) index, are reduced below the level or activity observed in the absence of the polypeptides described herein or lower than a control polypeptide. In certain embodiments, reduction with a polypeptide described herein is below the level or activity observed in the presence of an inactive or attenuated molecule. In some embodiments, the polypeptides described herein are capable of reducing the level of glucose, insulin, cholesterol, or triglyceride in the serum and/or in another tissue or organ, such as, e.g., liver, heart, muscle, visceral fat, subcutaneous fat, intestine, and brain.

As used herein, the value of body mass index (BMI) of a subject can be calculated with the following formula: BMI= (Mass of the subject expressed in kg)/[(height of the subject expressed in m)$^2$]. The level of inflammation can be measured by following various clinical tests available in the art. For instance, the level of C-reactive protein (CRP) in blood can be measured to quantitatively measure the level of inflammation in a subject. An erythrocyte sedimentation rate (ESR) test is another example of tests that measure the level of inflammation in a subject. The ESR test measures the rate of erythrocytes sediment in a set period. Upon obtaining the levels (such as, e.g., in mmol/L) of total cholesterol (TC) and HDL-C in a subject, the value of atherosclerosis index (AI) can be calculated by following the formula of AI=(TC-HDL-C)/HDL-C. As used herein, homeostatic model assessment (HOMA) index may refer HOMA-IR (quantifying the level of insulin resistance) index and/or HOMA-β index (quantifying the level of β-cell function). The value of HOMA-IR can be calculated by following the formula of: HOMA-IR=[(blood glucose expressed in mmol/L)×(serum insulin expressed in mU/L)]/22.5. The value of HOMA-β can be calculated by following the formula of: HOMA-β=[(20× serum insulin expressed in mU/L)(blood glucose expressed in mmol/L−3.5)]%. The value of heart index refers to the ratio between the weight of heart and the total body weight and can be calculated by following the formula of: heart index (g/kg)=weight of heart in g/body weight in kg. The value of kidney index refers to the ratio between the weight of kidney and the total body weight and can be calculated by following the formula of: kidney index (g/kg)=weight of kidney in g/body weight in kg. The value of total fat index refers to the ratio between the weight of fat (e.g., abdominal and/or scapular fat) and the total body weight. As used herein, the fat index can be calculated by following the formula of: total fat index (g/kg)=total weight of abdominal fat and scapular fat in g/body weight in kg.

Likewise, the terms "enhance," "increase," "elevate," "up-regulate," and "promote" all used interchangeably, mean that the level or activity of one or more chemical or biological molecules associated with metabolism, such as, e.g., glucose, triglyceride, cholesterol, free fatty acids, bile acids, amino acids, hormones, including, e.g., insulin, LDL-C, HDL-C, HbA1c, blood urea nitrogen, and minerals, is increased above the level or activity observed in the absence of the polypeptides described herein or higher than a control polypeptide. In some embodiments, "enhance" may mean that the level of value of one or more physiological parameters that measure metabolic changes, such as, e.g., glycemia, blood pressure, body weight, fat mass, body mass index (BMI), inflammation, atherosclerosis index (AI), heart index, kidney index, total fat index, and homeostatic model assessment (HOMA) index, are increased above the level or activity observed in the absence of the polypeptides described herein or higher than a control polypeptide. In certain embodiments, increase with a polypeptide described herein is above the level or activity observed in the presence of an inactive or attenuated molecule. In some embodiments, the polypeptides described herein are capable of increasing the level of bile acid in the serum and/or in another tissue or organ, such as, e.g., liver, heart, muscle, visceral fat, subcutaneous fat, intestine, and brain.

The terms "stabilize," "maintain," "sustain," and "preserve," are used interchangeably in connection with one or more chemical or biological molecules associated with metabolism, and mean that the level or activity of the one or more chemical or biological molecules associated with metabolism, such as, e.g., glucose, triglyceride, cholesterol, free fatty acids, bile acids, amino acids, hormones, including, e.g., insulin, LDL-C, HDL-C, HbA1c, blood urea nitrogen, and minerals, shows a minimal difference from the level or activity observed in a healthy subject or a subject who is not suffering from a metabolic disease, or from the level or activity observed in the presence of a positive control polypeptide. In some embodiments, "stabilize" may mean that the level or value of one or more physiological parameters that measure metabolic changes, such as, e.g., glycemia, blood pressure, body weight, fat mass, body mass index (BMI), inflammation, atherosclerosis index (AI), heart index, kidney index, total fat index, and homeostatic model assessment (HOMA) index, shows a minimal difference from the level or value observed in a healthy subject or a subject who is not suffering from a metabolic disease, or from the level or value observed in the presence of a positive control polypeptide. In some embodiments, the polypeptides described herein are capable of stabilizing the level of insulin in the serum and/or insulin production from pancreas.

The polypeptides described herein can be made by chemical synthesis or by employing recombinant technology.

When recombinant procedures are selected, a synthetic gene may be constructed de novo or a natural gene may be mutated by, for example, cassette mutagenesis. The polypeptides described herein may be produced using recombinant DNA techniques. These techniques contemplate, in simplified form, taking the gene, either natural or synthetic, encoding the peptide; inserting it into an appropriate vector; inserting the vector into an appropriate host cell; culturing the host cell to cause expression of the gene; and recovering or isolating the peptide produced thereby. In some embodiments, the recovered peptide is then purified to a suitable degree.

For example, the DNA sequence encoding a polypeptide described herein is cloned and manipulated so that it may be expressed in a convenient host. DNA encoding parent polypeptides can be obtained from an HBV genomic library, from cDNA derived from mRNA from cells expressing the polypeptide, or by synthetically constructing the DNA sequence. The parent DNA is then inserted into an appropriate plasmid or vector which is used to transform a host cell. In general, plasmid vectors containing replication and control sequences which are derived from species compatible with the host cell are used in connection with those hosts. The vector ordinarily carries a replication site, as well as sequences which encode proteins or peptides that are capable of providing phenotypic selection in transformed cells. The vector may be those commonly used in the art, or constructed using standard techniques by combining functional fragments of the vectors commonly used in the art.

The host cell may be prokaryotic or eukaryotic. For example, prokaryotic host cells may include *E. coli, Bacillus subtilis*, and other enterobacteriaceae such as, e.g., *Salmonella typhimurium* or *Serratia marcesans*, and various *Pseudomonas* species. In addition to prokaryotes, eukaryotic organisms, such as yeast cultures, or cells derived from multicellular organisms, such as insect or mammalian cell cultures, may be used. Examples of such eukaryotic host cell lines include VERO and HeLa cells, Chinese Hamster Ovary (CHO) cell lines, W138, 293, BHK, COS-7, and MDCK cell lines.

In some embodiments, the polypeptides described herein may be prepared using solid-phase synthesis, or other equivalent chemical syntheses known in the art. In some embodiments, solid-phase synthesis is initiated from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethylchloroformate, phenyl chloroformate, sec-butyl chloroformate, isobutyl chloroformate, pivaloyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole. Another coupling method involves use of a suitable coupling agent such as N,N'-dicyclohexylcarbodiimide or N,N'-diisopropylcarbodiimide.

In some embodiments, the α-amino group of each amino acid employed in the peptide synthesis may be protected during the coupling reaction to prevent side reactions involving their active α-amino function. For example, certain amino acids that contain reactive side-chain functional groups (e.g., sulThydryl, amino, carboxyl, and hydroxyl) may be protected with suitable protecting groups to prevent a chemical reaction from occurring at that site during both the initial and subsequent coupling steps. The selection of a suitable side-chain protecting group is within the skill of the art. The protecting group will be readily removable upon completion of the desired amino acid peptide under reaction conditions that will not alter the structure of the peptide chain.

After removal of the α-amino protecting group, the remaining α-amino and side-chain protected amino acids are coupled stepwise within the desired order. As an alternative to adding each amino acid separately in the synthesis, some may be coupled to one another prior to addition to the solid-phase synthesizer. The selection of an appropriate coupling reagent is within the skill of the art.

Each protected amino acid or amino acid sequence is introduced into the solid-phase reactor in excess, and the coupling is suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. The coupling reactions can be performed automatically using well known methods, for example, a BIOSEARCH 9500™ peptide synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloro-methylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix. It will also be recognized that the polypeptides may be modified (such as, e.g., modified at the N-terminus with a hydrophobic group, including, e.g., myristic acid, palmitic acid, stearic acid, oleic acid, linoleic acid, cholesterol, arachidonic acid; modified at the C-terminus by amidation (amination), isopentanediolization, or other stabilizing C-terminal modification) either before or after the polypeptide is cleaved from the support.

Purification of the polypeptides of the invention may be achieved using conventional procedures such as preparative HPLC (including reversed phase HPLC) or other known chromatographic techniques such as gel permeation, ion exchange, partition chromatography, affinity chromatography (including monoclonal antibody columns) or countercurrent distribution.

II. Pharmaceutical Compositions

The present disclosure also provides compositions, including pharmaceutical compositions, comprising a polypeptide described herein. In certain embodiments, the composition may comprise any one or more polypeptides described herein. In some embodiments, the composition may further comprise a suitable pharmaceutically acceptable carrier. In some embodiments, when administered to a subject in need thereof, the pharmaceutical composition provides serum concentrations of the polypeptide described herein that allow for bidirectional regulation of NTCP-mediated bile acid uptake in the subject.

A "pharmaceutically acceptable carrier" refers to an inactive ingredient, such as, e.g., solid, semisolid, or liquid filler, diluent, encapsulating material, formulation auxiliary, excipient, or carrier, for use with a therapeutic agent that together comprise a "pharmaceutical composition" for administration to a subject. A pharmaceutically acceptable carrier is non-toxic to recipients at the dosages and concentrations employed, and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Pharmaceutical compositions of the polypeptides described herein may be prepared by mixing such polypeptide having the desired degree of purity with one or more optional pharmaceutically acceptable carriers. Pharmaceutically acceptable carriers may include, e.g.: buffers (such as, e.g., phosphate, citrate, and other organic acids); antioxidants (such as, e.g., ascorbic acid and methionine); preservatives (such as, e.g., octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol); low molecular weight (such as, e.g., less than about 10 residues) polypeptides; proteins (such as, e.g., serum albumin, gelatin, or immunoglobulins); hydrophilic polymers (such as, e.g., polyvinylpyrrolidone); amino acids (such as, e.g., glycine, glutamine, asparagine, histidine, arginine, or lysine); monosaccharides, disaccharides, and other carbohydrates including glucose, mannose, or dextrins; chelating agents (such as, e.g., EDTA); sugars (such as, e.g., sucrose, mannitol, trehalose or sorbitol); salt-forming counter-ions (such as, e.g., sodium); metal complexes (such as, e.g., Zn— protein complexes); and/or non-ionic surfactants (such as, e.g., polyethylene glycol (PEG)).

Exemplary pharmaceutical carriers may also include binding agents (such as, e.g., pregelatinized maize starch, polyvinylpyrrolidone or hydroxypropyl methylcellulose, etc.); fillers (such as, e.g., lactose and other sugars, microcrystalline cellulose, pectin, gelatin, calcium sulfate, ethyl cellulose, polyacrylates or calcium hydrogen phosphate, etc.); lubricants (such as, e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (such as, e.g., starch, sodium starch glycolate, etc.); and wetting agents (such as, e.g., sodium lauryl sulphate, etc.).

Exemplary pharmaceutically acceptable carriers may further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). In some embodiments, a sHASEGP may be combined in the pharmaceutical composition with one or more additional glycosammoglycanases, such as, e.g., chondroitinases.

The pharmaceutical compositions may also comprise more than one active ingredient suitable for the particular indication being treated, for example, those with complementary activities that do not adversely affect each other. Such active ingredients may be suitably present in combination in amounts that are effective for the purpose intended.

In some embodiments, the active ingredients may be entrapped in microcapsules prepared, for example, by coacervation techniques or by interfacial polymerization, such as, e.g., hydroxymethylcellulose or gelatin-microcapsules and poly-(methylmethacylate) microcapsules, respectively, in colloidal drug delivery systems (such as e.g., liposomes, albumin microspheres, microemulsions, nanoparticles and nanocapsules), or in macroemulsions.

In some embodiments, the pharmaceutical composition may comprise sustained-release preparations. Suitable examples of sustained-release preparations include, e.g., semipermeable matrices of solid hydrophobic polymers containing the polypeptides described herein, which matrices may be in the form of shaped articles, such as, e.g., films or microcapsules.

In some embodiments, the pharmaceutical compositions may be used for in vivo administration and may be sterile. Sterility may be readily accomplished, e.g., by filtration through sterile filtration membranes.

The pharmaceutical compositions may be formulated into any of many possible dosage forms, such as, e.g., tablets, capsules, gel capsules, powders, or granules. The pharmaceutical compositions may also be formulated as solutions, suspensions, emulsions, or mixed media. In some embodiments, the pharmaceutical compositions may be formulated as lyophilized formulations or aqueous solutions.

In some embodiments, the pharmaceutical compositions may be formulated as a solution. For example, the polypeptides described herein may be administered in an unbuffered solution, such as, e.g., in saline or in water. In some embodiments, the polypeptides may also be administered in a suitable buffer solution. For example, the buffer solution may comprise acetate, citrate, prolamine, carbonate, or phosphate, or any combination thereof. In some embodiments, the buffer solution may be phosphate buffered saline (PBS). The pH and osmolality of the buffer solution containing the polypeptides can be adjusted to be suitable for administering to a subject.

In some embodiments, the pharmaceutical compositions may be formulated as suspensions in aqueous, non-aqueous, or mixed media. Aqueous suspensions may further contain substances which increase the viscosity of the suspension including, for example, sodium carboxymethylcellulose, sorbitol and/or dextran. The suspension may also contain stabilizers.

In some embodiments, the pharmaceutical compositions may be formulated as emulsions. Exemplary emulsions include heterogeneous systems of one liquid dispersed in another in the form of droplets usually exceeding 0.1 µm in diameter. Emulsions may contain additional components in addition to the dispersed phases, and the active drug which may be present in a solution in the aqueous phase, the oily phase, or itself as a separate phase. Microemulsions are also included as an embodiment of the present disclosure. In some embodiments, the pharmaceutical compositions may also be formulated as liposomal formulations.

III. Methods of Use

Embodiments of the present disclosure include therapeutic uses of the polypeptides described herein. In one aspect, use of the polypeptides described herein as a medicament is provided. In another aspect, use of the polypeptides described herein in treating a metabolic disease is provided. In some embodiments, the metabolic disease involves dysregulation of lipid metabolism. In certain embodiments, the metabolic disease may be a cholesterol-related disorder. In some embodiments, the cholesterol-related disorder may be hyperlipidemia. In some embodiments, the hyperlipidemia may be hypertriglyceridemia, hypercholesterolemia, or a combination thereof. In some embodiments, use of the polypeptides described herein in treating conditions associated with elevated serum level of any one of total triglycerides, total cholesterol, and LDL-C is provided.

In some embodiments, the metabolic disease involves dysregulation of glucose metabolism. In some embodiments, the metabolic disease is diabetes. In some embodiments, the metabolic disease is type II diabetes. In some embodiments, the metabolic disease is obesity. In some embodiments, use of the polypeptides described herein in treating conditions associated with elevated serum level of glucose or HbA1c is also provided.

In another aspect, a method of treating a metabolic disease in a subject is provided, comprising administering to the subject a therapeutically effective amount of the polypeptides described herein or of a pharmaceutical composition of such polypeptide. In certain embodiments, the subject may suffer from a metabolic disease or may be at risk of developing such disease. In some embodiments, the subject may be a mammal. In some embodiments, the subject may be a human. In certain embodiments, the methods and uses described herein may further comprise administering to the subject a therapeutically effective amount of at least one additional therapeutic agent.

In some embodiments, the metabolic disease involves dysregulation of lipid metabolism. In some embodiments, the metabolic disease may be a cholesterol-related disorder. In some embodiments, the cholesterol-related disorder may be hyperlipidemia. In some embodiments, the hyperlipidemia may be hypertriglyceridemia, hypercholesterolemia, or a combination thereof.

In other aspects, a method of lowering the level of serum lipids, such as, e.g., the total cholesterol, total triglyceride, or LDL cholesterol level, in a subject in need thereof is provided, comprising administering to the subject a therapeutically effective amount of the polypeptide described herein or of a pharmaceutical composition of such polypeptide. In some embodiments, the subject is suffering or at risk of developing a metabolic disease involving dysregulation of lipid metabolism. In some embodiments, the subject is suffering or at risk of developing a cholesterol-related disorder. In some embodiments, the subject is suffering or at risk of developing hyperlipidemia. In some embodiments, the subject is suffering or at risk of developing hypertriglyceridemia, hypercholesterolemia, or a combination thereof.

In some embodiments, the metabolic disease involves dysregulation of glucose metabolism. In some embodiments, the metabolic disease is diabetes. In some embodiments, the metabolic disease is type II diabetes. In some embodiments, the metabolic disease is obesity.

In lowering aspects, a method of lowering the blood glucose or HbA1c level in a subject in need thereof is provided, comprising administering to the subject a therapeutically effective amount of the polypeptide described herein or of a pharmaceutical composition of such polypeptide. In some aspects, a method of stabilizing the serum level of insulin in a subject in need thereof is provided, comprising administering to the subject a therapeutically effective amount of the polypeptide described herein or of a pharmaceutical composition of such polypeptide. In some embodiments, the subject is suffering from or at risk of developing a metabolic disease involving dysregulation of glucose metabolism. In some embodiments, the subject is suffering or at risk of developing diabetes. In some embodiments, the subject is suffering from or at a risk of developing type II diabetes. In some embodiments, the subject is suffering from or at a risk of developing obesity.

Without being bound by theory, it is believed that the polypeptide described herein may be capable of treating the metabolic diseases or modulating the serum level of metabolism-associated molecules in the subject by bidirectionally regulating NTCP-mediated bile acid uptake in the subject following administration of the polypeptide to the subject. In some embodiments, when the concentration of the polypeptide described herein in the blood stream of a subject administered with such polypeptide is at or below a certain concentration, bile acid uptake in the subject is enhanced. In some embodiments, when the concentration of the polypeptide described herein in the blood stream of the subject is above a certain concentration, bile acid uptake in the subject is inhibited. In some embodiments, when the concentration of the polypeptide described herein in the blood stream of a subject administered with such polypeptide is at or below 93 nmol/L, bile acid uptake in the subject is enhanced. In some embodiments, when the concentration of the polypeptide described herein in the blood stream of the subject is above 93 nmol/L, bile acid uptake in the subject is inhibited. For example, when the concentration of the Cmyr-47 polypeptide described herein in the blood stream of a subject administered with such polypeptide is at or below 500 ng/ml, bile acid uptake in the subject is enhanced. When the concentration of the Cmyr-47 polypeptide described herein in the blood stream of the subject is above 500 ng/ml, bile acid uptake in the subject is inhibited. In some embodiments, the serum concentration of the polypeptide described herein may be measured at least about 10, 20, 40, 60, 90, 120, 180, 240, or 360 minutes following the administration. In some embodiments, the serum concentration of the polypeptide described herein is above 93 nmol/L by certain time following the administration. In some embodiments, the serum concentration of the polypeptide described herein is at or below 93 nmol/L after that time following the administration. For example, the serum concentration of the Cmyr-47 polypeptide described herein is above 500 ng/ml by a certain time following the administration. In some embodiments, the serum concentration of the Cmyr-47 polypeptide described herein is at or below 500 ng/ml after that time following the administration. In some embodiments, such threshold serum concentration of the polypeptide occurs at about 20 minutes following the administration.

As used herein, a "metabolic disease" or "metabolic disorder" includes any disease that may be caused by dysregulation of metabolic pathways, such as, e.g., pathways involved in bile acid metabolism, glucose metabolism, lipid metabolism, and amino acid metabolism. In some embodiments, the metabolic disease refers to a disease that involves dysregulation of lipid metabolism. In certain embodiments, the metabolic disease refers to a disease that comprises dysregulation in producing, clearing, and/or utilizing lipid metabolites including, e.g., bile acids, cholesterol, triglycerides, and fatty acids. The metabolic disease described herein therefore may refer to a cholesterol-related disorder. The metabolic disease described herein therefore may refer to hyperlipidemia, such as, e.g., hypertriglyceridemia, hypercholesterolemia, or a combination thereof. In some embodiments, the metabolic disease refers to a disease that involves dysregulation of glucose metabolism. In certain embodiments, the metabolic disease refers to a disease that comprises dysregulation in producing, clearing, and/or utilizing glucose metabolites, e.g., glucose, pyruvate, and glucose-6-phosphate. The metabolic disease described herein therefore may refer to diabetes and obesity.

The metabolic disease described herein may be chosen from hyperglycemia; hypoglycemia; hyperinsulinemia; obesity, hyperlipidemia; hypertriglyceridemia; hypercholesterolemia; heart disease; metabolic syndrome; atherosclerotic disease; coronary heart disease; coronary artery disease; peripheral arterial disease; angina pectoris; cerebrovascular disease; acute coronary syndrome; myocardial infarction; stroke; cardiovascular disease; Alzheimer's disease; dyslipidemias; familial combined hyperlipidemia; familial hypertriglyceridemia; familial hypercholesterolemia; heterozygous hypercholesterolemia; homozygous hypercholesterolemia; familial defective apolipoprotein B-100; polygenic hypercholesterolemia; remnant removal disease; hepatic lipase deficiency; dyslipidemia caused by dietary indiscretion, hypothyroidism, drugs including estrogen and progestin therapy, beta-blockers, and thiazide diuretics; nephrotic syndrome; chronic renal failure; Cushing's syndrome; primary biliary cirrhosis; glycogen storage disease; hepatoma; cholestasis; acromegaly; insulinoma; isolated growth hormone deficiency; kidney impairment; obesity; and alcohol-induced hypertriglyceridemia.

The term "metabolic disease" includes, e.g., type I diabetes, type II diabetes, hyperglycemia, hypoglycemia, hyperinsulinemia, obesity, hyperlipidemia, hypertriglyceridemia, hypercholesterolemia, heart disease, metabolic syndrome, coronary heart disease, stroke, cardiovascular diseases, Alzheimer's disease, and generally dyslipidemias, which can be manifested, for example, by an elevated total serum cholesterol, LDL, triglycerides, VLDL, and/or HDL. Some non-limiting examples of primary and secondary dyslipidemias that can be treated using the polypeptides described herein, either alone or in combination with one or more other agents include metabolic syndrome, diabetes, hyperlipidemia, familial combined hyperlipidemia, familial hypertriglyceridemia, familial hypercholesterolemia, including heterozygous hypercholesterolemia, homozygous hypercholesterolemia, familial defective apolipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia.

In some embodiments, the polypeptide described herein is useful in preventing or treating one or more metabolic diseases. In certain embodiments, the polypeptides described herein can also be useful in preventing or treating one or more symptoms or complications associated with a metabolic disease. For instance, the polypeptide can be used to prevent or treat cardiovascular diseases, including atherosclerotic diseases, such as, e.g., coronary heart disease, coronary artery disease, peripheral arterial disease, stroke (ischaemic and hemorrhagic), angina pectoris, or cerebrovascular disease and acute coronary syndrome, myocardial infarction. In certain embodiments, the polypeptides described herein can also be useful in preventing or treating heart diseases, kidney impairment, or obesity associated with a metabolic disorder.

The term "diabetes" refers to a disease or condition generally characterized by metabolic defects in production and/or utilization of glucose that result in the failure to maintain appropriate blood sugar levels in the body. The results of these defects include elevated blood glucose, referred to as "hyperglycemia." Two major forms of diabetes are Type I diabetes and Type II diabetes. Type I diabetes generally results from an absolute deficiency of insulin (e.g., the production from pancreatic p cells is extremely low or completely ablated), therefore failing to regulate glucose utilization. Type II diabetes often occurs in the face of normal or even elevated levels of insulin, and can result from the inability of tissues to respond appropriately to insulin. Most Type II diabetic patients are insulin resistant and have a relative deficiency of insulin in that insulin secretion cannot compensate for the resistance of peripheral tissues to respond to insulin.

The term "hyperlipidemia" refers to a condition characterized by an abnormal increase in serum lipids. The lipids fractions in the circulating blood include, e.g., total cholesterol, certain lipoproteins, and triglycerides. Serum lipoproteins serve as carriers for lipids in the circulation and are classified by their density, including: chylomicrons, very low density lipoproteins ("LDL"), intermediate density lipoproteins ("IDL"), low density lipoproteins ("LDL"), and high density lipoproteins ("HDL"). The term "hyperlipidemia" encompasses primary and secondary hyperlipidemia. Primary hyperlipidemia is generally caused by genetic defects, while secondary hyperlipidemia is generally caused by other factors, such as various disease states, drugs, and dietary factors. For example, secondary hyperlipidemia may be caused by diabetes. Alternatively, hyperlipidemia can result from a combination of primary and secondary causes. Hyperlipidemia may encompass hypertriglyceridemia, hypercholesterolemia, or a combination thereof. The term "hypertriglyceridemia," as used herein, refers to a condition in which serum total triglyceride levels are elevated above a desired level. The term "hypercholesterolemia," as used herein, refers to a condition in which serum cholesterol levels are elevated above a desired level. In certain embodiments, the serum total cholesterol, HDL cholesterol ("HDL-C"), or LDL cholesterol ("LDL-C") levels are elevated above the desired level in hypercholesterolemia. Hyperlipidemia also imposes a risk in and may encompass development of cardiovascular and atherosclerosis diseases. The term "cardiovascular disease" encompasses a disease of the blood vessels of the circulation system caused by abnormally high concentrations of lipids in the vessels. The term "atherosclerosis" refers to a disease of the arteries in which fatty plaques develop on the inner walls, with eventual obstruction of blood flow.

"Patient" and "subject" may be used interchangeably to refer to an animal, such as a mammal or a human, being treated or assessed for a disease, disorder, or condition, at risk of developing a disease, disorder, or condition, or having or suffering from a disease, disorder, or condition. In some embodiments, such disease, disorder, or condition may include a metabolic disease. In some embodiments, the metabolic disease may involve dysregulation of lipid metabolism. In some embodiments, the metabolic disease may be a cholesterol-related disorder, such as hyperlipidemia (e.g., hypercholesterolemia, hypertriglyceridemia, or a combination thereof). In some embodiments, the metabolic disease may involve dysregulation of glucose metabolism. In some embodiments, the metabolic disease may be diabetes, including type I and type II diabetes.

The term a "therapeutically effective amount" or "effective amount" of a polypeptide described herein or a composition comprising such polypeptide refers to an amount effective in the prevention or treatment of a disorder for the treatment of which the polypeptide or composition is effective. The term may include an amount of the polypeptide described herein that is effective in increasing the serum level of bile acid in a subject suffering from or at a risk of developing a metabolic disease. The term may include an amount of the polypeptide described herein that is effective in lowering the blood glucose or HbA1c level or stabilizing the serum level of insulin in a subject suffering from or at a risk of developing a metabolic disease, such as, e.g., diabetes and obesity. The term may also include an amount of the polypeptide described herein that is effective in lowering the level of serum lipids, such as, e.g., the total cholesterol, total triglycerides, LDL cholesterol level, in a subject suffering from or at a risk of developing a metabolic disease, such as, e.g., hyperlipidemia, including hypercholesterolemia, hypertriglyceridemia, or both. The term also includes an amount of a polypeptide described herein that, when administered to a subject for treating a metabolic disease, such as, e.g., diabetes and hyperlipidemia (e.g., hypercholesterolemia, hypertriglyceridemia, or both), is sufficient to effect treatment of the disease, e.g., by diminishing, ameliorating, or maintaining the existing disease or one or more symptoms of the disease, or by inhibiting the progression of the disease. The "therapeutically effective amount" or "effective amount" may vary depending on the polypeptide, the route of administration, the disease and its severity, and the health, age, weight, family history, genetic makeup, stage of pathological processes, the types of preceding or concomitant treatments, if any, and other individual characteristics of the subject to be treated.

The "therapeutically effective amount" of the polypeptide described herein may allow the administered polypeptide to reach a concentration in the blood stream of the subject at which the polypeptide is capable of inhibiting NTCP-mediated bile acid uptake in the subject. In some embodiments, a therapeutically effective amount of the polypeptide described herein may allow the administered polypeptide to reach at least about 93 nmol/L in the blood stream of a subject administered with that amount. For example, a therapeutically effective amount of the Cmyr-47 polypeptide described herein may allow the administered polypeptide to reach at least about 500 ng/ml in the blood stream of a subject administered with that amount.

In certain embodiments, a therapeutically effective amount of the polypeptide described herein refers to an amount such that the serum concentrations of the administered polypeptide allow for bidirectional regulation of NTCP-mediated bile acid uptake in the subject. For instance, when a subject is administered with a therapeutically effective amount of the polypeptide described herein, the initial serum concentration of the polypeptide in the subject may be above a certain concentration where the polypeptide inhibits NTCP-mediated bile acids uptake. The serum concentration of the polypeptide in the subject may gradually reduce and fall to or below a value where the polypeptide begins enhancing NTCP-mediated bile acids uptake. The serum concentration of the administered polypeptide may be assessed at least about 10, 20, 40, 60, 90, 120, 180, 240, or 360 minutes after the administration. In some embodiments, the therapeutically effective amount of the polypeptide described herein allows the polypeptide to reach a serum concentration above 93 nmol/L by certain time following the administration. In some embodiments, the therapeutically effective amount of the polypeptide described herein allows the polypeptide to reach a serum concentration at or below 93 nmol/L after that certain time following the administration. For example, the therapeutically effective amount of the Cmyr-47 polypeptide described herein allows the polypeptide to reach a serum concentration above 500 ng/ml by certain time following the administration. In some embodiments, the therapeutically effective amount of the Cmyr-47 polypeptide described herein allows the polypeptide to reach a serum concentration at or below 500 ng/ml after that certain time following the administration. In some embodiments, the therapeutically effective amount of the polypeptide described herein produces such threshold serum concentration of the polypeptide at about 20 minutes following the administration.

In various embodiments, the term "treatment" includes treatment of a subject (e.g. a mammal, such as a human) or a cell to alter the current course of the subject or cell. Treatment includes, e.g., administration of a polypeptide described herein or a pharmaceutical composition comprising such polypeptide, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition or the associated symptoms. In various embodiments, the term "treatment" may include relieving, slowing, or reversing the pathological processes or symptoms in a subject suffering from a metabolic disease, such as, e.g., diabetes and hyperlipidemia (e.g., hypercholesterolemia, hypertriglyceridemia, or both). In some embodiments, the term "treatment" may include improving at least one symptom or measurable parameter of a metabolic disease. It will be apparent to one of skill in the art which biological and/or physiological parameters can be used to access the pathological process of the metabolic disease. Such pathological processes or symptoms may include, e.g., excessive or increased levels compared with healthy subjects of one or more chemical or biological molecules associated with metabolism, such as, e.g., glucose, triglyceride, cholesterol, free fatty acids, bile acids, amino acids, hormones, including, e.g., insulin, LDL-C, HDL-C, HbA1c, blood urea nitrogen, and minerals; or of one or more physiological parameters that measure metabolic changes, such as, e.g., glycemia, blood pressure, body weight, fat mass, body mass index (BMI), inflammation, atherosclerosis index (AI), heart index, kidney index, total fat index, and homeostatic model assessment (HOMA) index.

The terms "administering," or "administer" include delivery of the polypeptide described herein to a subject either by local or systemic administration. Administration may be topical (including ophthalmic and to mucous membranes including vaginal and rectal delivery), pulmonary (e.g., by inhalation or insufflation of powders or aerosols, including by nebulizer, intratracheal, intranasal), epidermal, transdermal, oral, or parenteral. Parenteral administration includes intravenous, subcutaneous, intraperitoneal, or intramuscular injection or infusion; or intracranial, e.g., intrathecal or intraventricular, administration.

In certain embodiments, the present disclosure provides use of the polypeptides described herein in modulating, such as, e.g., reducing or stabilizing, the level or activity of one or more chemical or biological molecules associated with metabolism, such as, e.g., glucose, triglyceride, cholesterol, free fatty acids, bile acids, amino acids, hormones, LDL-C, HDL-C, HbA1c, blood urea nitrogen, and minerals in a subject. In some embodiments, the present disclosure provides use of the polypeptides described herein in modulating, such as, e.g., reducing or stabilizing, the level or value of one or more physiological parameters that measure metabolic changes such as, e.g., glycemia, blood pressure, body weight, fat mass, body mass index (BMI), inflammation, atherosclerosis index (AI), heart index, kidney index, total fat index, and homeostatic model assessment (HOMA) index.

In some embodiments, the present disclosure provides use of the polypeptides described herein in reducing the level of serum lipids in a subject. In some embodiments, the present disclosure provides use of the polypeptides described herein in reducing the serum level of total cholesterol in a subject. In further embodiments, the present disclosure provides use of the polypeptides described herein in reducing the serum level of LDL-cholesterol in a subject. In some embodiments, the present disclosure provides use of the polypeptides described herein in reducing the serum level of triglyceride in a subject. In some embodiments, the present disclosure provides use of the polypeptides described herein in reducing the serum level of glucose in a subject. In some embodiments, the present disclosure provides use of the polypeptides described herein in stabilizing the serum level of insulin in a subject. In some embodiments, the subject may be a mammal. In some embodiments, the subject may be a human.

In some embodiments, the present disclosure provides use of the polypeptides described herein in reducing the risk of developing a metabolic disease. In certain embodiments, the present disclosure also provides use of the polypeptides described herein in reducing the risk of developing one or more symptoms or complications associated with a metabolic disease. In some embodiments, the metabolic disease involves dysregulation of lipid metabolism. In some embodiments, the metabolic disease is a cholesterol-related disorder. In some embodiments, the metabolic disease is hyperlipidemia. The hyperlipidemia may include hypertriglyceridemia, hypercholesterolemia, or both. In some embodiments, the metabolic disease involves dysregulation of glucose metabolism. In some embodiments, the metabolic disease is diabetes. The diabetes may include type I and type II diabetes. In some embodiments, the metabolic disease is obesity. The symptoms or complications associated with the metabolic disease may include, e.g., cardiovascular diseases such as atherosclerosis diseases, heart diseases, kidney impairment, or obesity, in a subject having such metabolic disease (such as, e.g., diabetes, hyperlipidemia, including hypertriglyceridemia, hypercholesterolemia, or both).

The present disclosure also provides methods to carry out the above uses of the polypeptides described herein in a subject. Such methods may comprise administering to the subject a therapeutically effective amount of a polypeptide described herein or of a pharmaceutical composition comprising such polypeptide. In some embodiments, the subject may be a mammal. In some embodiments, the subject may be a human. In some embodiments, the subject may suffer from a metabolic disease or may be at risk of developing such disease.

In a further aspect, the present disclosure provides for the use of the polypeptides described herein in the manufacture or preparation of a medicament. In some embodiments, the medicament may be for treatment of a metabolic disease. The metabolic disease may involve dysregulation of lipid metabolism. In some embodiments, the medicament may be for treatment of a cholesterol-related disorder. In some embodiments, the cholesterol-related disorder may be hyperlipidemia. The hyperlipidemia may be hypertriglyceridemia, hypercholesterolemia, or a combination thereof. In yet another embodiment, the medicament is for use in a method of lowering the level of serum lipids, such as, e.g., the total cholesterol, total triglyceride, or LDL cholesterol level, in a subject, comprising administering to the subject a therapeutically effective amount of the medicament.

In some embodiments, the metabolic disease may involve dysregulation of glucose metabolism. In some embodiments, the medicament may be for treatment of diabetes e.g., type I or type II diabetes. In some embodiments, the medicament may be for treatment of obesity. In another embodiment, the medicament is for use in a method of lowering the blood glucose or HbA1c level in a subject, comprising administering to the subject a therapeutically effective amount of the medicament.

In certain embodiments, the disorder treated may be any disease or condition which can be improved, ameliorated, inhibited, or prevented by bidirectionally regulating NTCP activity. In certain embodiments, disorders or disease that can benefit from the regulation of bile acid intake by hepatocytes can also be treated by the polypeptides described herein. In certain embodiments, subjects treatable by the polypeptides and methods and uses described herein may include subjects indicated for LDL apheresis, subjects with diabetes, subjects with primary hyperlipidemia (including hypercholesterolemia, hypertriglyceridemia, or a combination thereof) who are intolerant or uncontrolled by other therapeutic agent, and subjects at risk for developing hyperlipidemia who may be preventably treated. Other indications include dyslipidemia associated with secondary causes such as Type 2 diabetes mellitus, cholestatic liver diseases (primary biliary cirrhosis), nephrotic syndrome, hypothyroidism, obesity, and the prevention and treatment of cardiovascular diseases (e.g., atherosclerotic diseases), heart diseases, and kidney impairment.

In certain embodiments, the methods and uses described herein may further comprise administering to the subject an effective amount of at least one additional therapeutic agent. In certain embodiments, the additional therapeutic agent may be for preventing and/or treating one or more diseases associated with the metabolic diseases described herein, such as, e.g., one or more diseases associated with diabetes or hyperlipidemia. In certain embodiments, the additional therapeutic agent may be for preventing and/or treating cardiovascular diseases (e.g., atherosclerotic diseases). In certain embodiment, the additional therapeutic agent may be for reducing the risk of recurrent cardiovascular events. In certain embodiments, the additional therapeutic agent may be for preventing and/or treating heart diseases, kidney impairment, or obesity. The polypeptides described herein can be used either alone or in combination with other agents in a therapy. For instance, any of the polypeptides described herein may be administered before, concurrently with, or after administration of at least one additional therapeutic agent. In certain embodiments, the additional therapeutic agent may be chosen from e.g., an antihyperlipidemic agent, an antihyperglycemic agent, an antidiabetic agent, an anti-obesity agent, and a bile acid analogue.

In some embodiment, the antihyperglycemic agent may be chosen from, e.g., a biduanide (e.g., metformin, phenformin, and buformin), insulin (e.g., regular human insulin, NPH insulin, insulin aspart, insulin lispro, insulin glargine, insulin detemir, and insulin levemir), a glucagon-like peptide 1 receptor agonist (GLP-RA; e.g., albiglutide, dulaglutide, exenatide, liraglutide, lixisenatide, and extended-release glucagon), a sodium-glucose cotransporter 2 inhibitor (SGLR2I; e.g., canagliflozin, empagliflozin, dapagliflozin, empagliflozin, and ipragliflozin), a dipeptidyl peptidase 4 inhibitor (DPP4I; e.g., bromocriptine, sitagliptin, vildagliptin, saxagliptin, linagliptin, anagliptin, teneligliptin, alogliptin, trelagliptin, gemigliptin, dutogliptin, omarigliptin, berberine, and lupeol), an α-glucosidase inhibitor (AGI; e.g., miglitol, acarbose, and voglibose), a thiazolidinedione (TZD; e.g., pioglitazone, rosiglitazone, lobeglitazone, troglitazone, ciglitazone, darglitazone, englitazone, netoglitazone, rivoglitazone, and mifepristone), a meglitinide (e.g., repaglinide, nateglinide, and mitiglinide), a sulfonylurea (SU; e.g., carbutamide, acetohexamide, chlorpropamide, tolbutamide, tolazamide, glipizide (glucotrol), gliclazide, glibenclamide, glyburide (e.g. Micronase), glibornuride, gliquidone, glisoxepide, glyclopyramide, glimepiride, amaryl, and glimiprime), an amylin analogue (e.g., pramlinitide), a proprotein convertase subtilisin/kexin type 9 inhibitor (PCSK9I; e.g., evolocumab, bococizumab, alirocumab, 1D05-IgG2, RG-7652, LY3015014, RNAi therapeutic ALN-PCS02, AMG-145, and REGN727/SAR236553), a glucokinase activator (GKA; e.g., MK-0941, RO-28-1675, and AZD1656), a PPAR agonist/modulator, a glucagon receptor antagonist, a C—C chemokine receptor type 2 (CCR2) antagonist, an Interleukin-1 modulator, a G-protein coupled receptor agonist, a gastrointestinal peptide agonist other than GLP-1, an SGLT1 and dual SGLT1/SGLT2 inhibitor (excluding an SGLT2-only inhibitor), an 11beta-HSD1 inhibitor, a diacylglycerol acyltransferase (DGAT)-1 inhibitor, a cannabinoid, a hepatic camitine palmitoyltransferase 1 (CPT1) inhibitor, a fibroblast growth factor (FGF)-21 agonist, a glucocorticoid receptor antagonist, a heat shock protein (HSP) inducer, a melanocortin-4 receptor (MC4R) agonist, a tetrahydrotriazin containing oral antidiabetic, glimin, a protein tyrosine phosphatase 1B (PTPB) inhibitor, a sirtuin1 (SIRT1) activator, and a microbiome modulator.

In some embodiment, the additional therapeutic agent is an antihyperlipidemic agent and may be chosen from, e.g., a statin (e.g., HMG-CoA reductase inhibitor; e.g., smvastatin, atorvastatin, rosuvastatin, pravastatin, pitavastatin, lovastatin, atorvastatin, fluvastatin, cerivastatin, mevastatin, pantethine, elastase, and probucol), a fibric acid (e.g., bezafibrate (e.g., Bezalip), ciprofibrate (e.g., Modalim), clofibrate, gemfibrozil (e.g., Lopid), fenofibrate (e.g., TriCor), clinofibrate (e.g., Lipoclin), lifibrate, alufibrate, simfibrate, etofylline clofibrate, and gemfibrozil), a nicotinic acid (e.g., niacin, inositol hexanicotinate, nicotinamide, and acipimox), a bile acid sequestrant (e.g., cholestyramine (e.g., Questran®), colesevelam (e.g., Welchol®), colestipol (e.g., Colestid®), polidexide, dholestyramine, and divistyramine), ezetimibe (e.g., Zetia), a proprotein convertase subtilisin/kexin type 9 inhibitor (PCSK9I; e.g., evolocumab, bococizumab, alirocumab, 1D05-IgG2, RG-7652, LY3015014, RNAi therapeutic ALN-PCS02, AMG-145, and REGN727/SAR236553), a microsomal triglyceride transfer protein inhibitor (MTTPI; e.g., lomitapide and JTT-130), an apolipoprotein B inhibitor (apoBI; e.g., mipomersen (e.g., Kynamro)), a diacylglycerol acyltransferase 1 (DGAT1) inhibitor (e.g., pradigastat), an angiopoietin-like protein 3 inhibitor (e.g., REGN1500), a cholesteryl ester transfer protein (CETP) inhibitor (e.g., anacetrapib and evacetrapib), a peroxisome proliferator-activated receptor (PPAR) α/γ agonist, an acyl-CoA inhibitor, an incretin mimetics inhibitor, an angiopoietin-like protein 3 (ANGPTL3) inhibitor, an angiopoietin-like protein 4 (ANGPTL4) inhibitor, an apoC-III-targeted inhibitor, and a selective peroxisome proliferator-activated receptor modulator (SPPARM).

In some embodiment, the additional therapeutic agent is an antiobesity agent and may be chosen from, e.g., orlistat (e.g., Xenical), lorcaserin (e.g., Belviq), phentermine, topiramate, diethylpropion, phendimetrazine, benzphetamine, and a combination of phendimetrazine and benzphetamine.

In some embodiment, the additional therapeutic agent is a bile acid analogue and may be chosen from, e.g., obeticholic acid, ursodeoxycholic acid, and cholylsarcosine.

In some embodiments, the additional therapeutic agent may also be chosen from, e.g., a farnesoid X receptor (FXR) agonist, an FXR inhibitor, a transemembrane G protein-coupled receptor 5 (TGR5) agonist, and a TGR5 inhibitor.

In some embodiments, the additional therapeutic agent may be chosen from insulin, metformin, sitagliptin, colesevelam, glipizide, simvastatin, atorvastatin, ezetimibe, fenofibrate, nicotinic acid, orlistat, lorcaserin, phentermine, topiramate, obeticholic acid, and ursodeoxycholic acid.

Such combination therapies described herein may encompass combined administration (where two or more therapeutic agents are included in the same or separate formulations), and separate administration, in which case, administration of the polypeptides described herein can occur prior to, simultaneously, and/or following, administration of the additional therapeutic agent.

The polypeptides described herein (and any additional therapeutic agent) can be administered by any suitable means, including parenteral, intrapulmonary, and intranasal, and, if desired for local treatment or intralesional administration. In some embodiments, the polypeptides described herein may be parenterally administered. Parenteral administration may include intramuscular, intravenous, intraarterial, intraperitoneal, or subcutaneous administration. In some embodiments, the polypeptides described herein may be administered subcutaneously. In some embodiments, the polypeptides described herein may administered intravenously. Dosing can be by any suitable route, such as, e.g., by injections or infusions, such as intravenous or subcutaneous injections or infusions, depending in part on whether the administration is brief or chronic. Various dosing schedules including e.g. single or multiple administrations over various time-points, bolus administration, and pulse infusion are also contemplated.

The polypeptides described herein would be formulated, dosed, and administered in a fashion consistent with common medical practice. Factors for consideration in this context may include, e.g., the particular disorder being treated, the particular mammal being treated, the clinical condition of the individual patient, the cause of the disorder, the site of delivery of the agent, the method of administration, the scheduling of administration, and other factors known to medical practitioners. The polypeptides described herein need not be but can be optionally formulated with one or more agents currently used to prevent or treat the disorder in question. The effective amount of such other agents depends on the amount of the polypeptide described herein present in the formulation, the type of disorder or treatment, and other factors discussed above.

For the prevention or treatment of disease, the appropriate dosage of a polypeptide described herein (when used alone or in combination with one or more other additional therapeutic agents) may depend on the type of disease to be treated, the severity and course of the disease, whether the polypeptide is administered for preventive or therapeutic purposes, previous therapy, the patient's clinical history and response to the polypeptide, and the discretion of the attending physician. The polypeptides described herein may be suitably administered to the patient at one time or over a series of treatments. Depending on the type and severity of the disease, the polypeptide described herein may be administered to the patient, for example, by one or more separate administrations, or by continuous infusion. For repeated administrations over several days or longer, depending on the condition, the treatment may be sustained until a desired suppression of disease symptoms occurs. The polypeptide described herein may be administered intermittently, e.g. every day, every two days, every three days, every week, or every two or three weeks (e.g. such that the patient receives from more than one, such as, e.g., about two to about twenty, or e.g. about six doses of the polypeptide). An initial higher loading dose, followed by one or more lower doses, may be administered.

In certain embodiments, a flat-fixed dosing regimen may be used to administer the polypeptide described herein to a subject. However, other dosage regimens may also be useful depending on the factors discussed above. The progress of this therapy can be easily monitored by conventional techniques and assays for the disease or condition treated.

The following Examples may be used for illustrative purposes and should not be deemed to narrow the scope of the invention.

Example 1

Example 1.1. Synthesis of Polypeptides

Polypeptides as shown in Table 1 were synthesized according to the standard Fmoc protocol for polypeptide synthesis. Generally, individual amino acid residues were extended from the carboxyl terminus to the amino terminus, starting from a MBHA resin. The N terminus was then modified by myristoylation. After completion of peptide synthesis, the polypeptides were cleaved from the resin by a cleavage solution and the C terminus of the polypeptides was further modified by amination. The resin was removed by filtering with G6 sand-core funnel and the filtrate containing the polypeptides was dried under vacuum. The polypeptide product was dissolved in deionized water, and purified in ÄKTA explorer 100 type medium pressure liquid chromatograph equipped with C18 column. The main peaks were recovered stepwise. The samples collected from the target peak were analyzed by Agilent 1100 type reversed phase high pressure liquid chromatography (HPLC) equipped with C18 column for their purities and confirmed by mass spectrometry for their molecular weights. The collected solutions purified by medium pressure liquid chromatography were freeze-dried for storage. The dried samples were dissolved in PBS and then filtered through a 0.20 μM membrane. The polypeptide stocks dissolved in PBS were stored at −80° C. before use. FIG. 1A shows an exemplary graph depicting the purity of the synthesized polypeptide, Cmyr-47, as measured by HPLC. FIG. 1B shows an exemplary graph confirming the correct molecular weight of Cmyr-47 (5398.8 Da) as measured by mass spectrometry.

Example 1.2. Binding Assay of Cmyr-47 and NTCP

Figure 2:
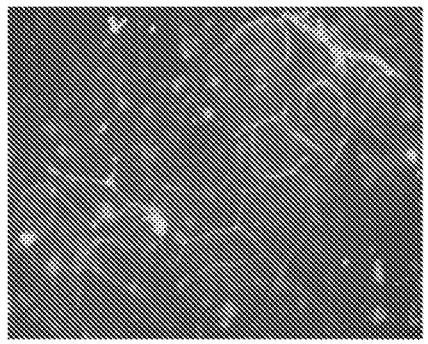
FIG. 2A shows that Cmyr-47 labeled with FIFC binds to tupaia primary hepatocytes.
FIG. 2B shows that Cmyr-47 labeled with FIFC binds to HepG2 cells, a human hepatocyte derived cell line.
Figure 2:
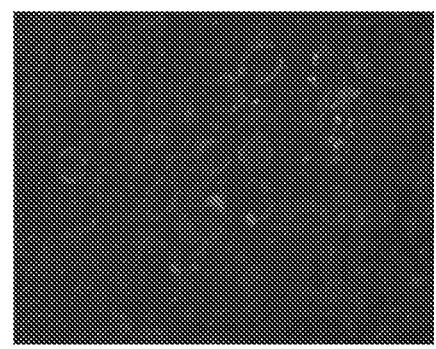
Figure 3:
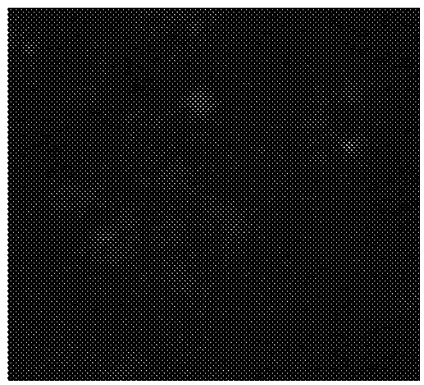
FIG. 3 illustrates that Cmyr-47 labeled with FIFC binds to NTCP expressing L02 cells ("NTCP-L02") but does not bind to control L02 cells ("BLANK-L02").
Figure 3:
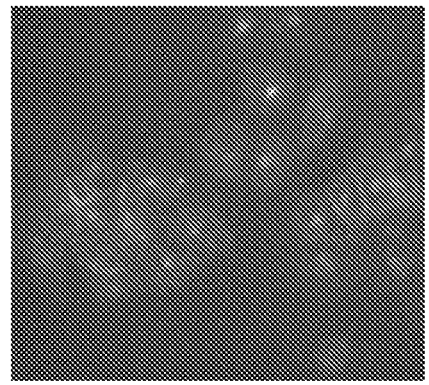
Figure 4:
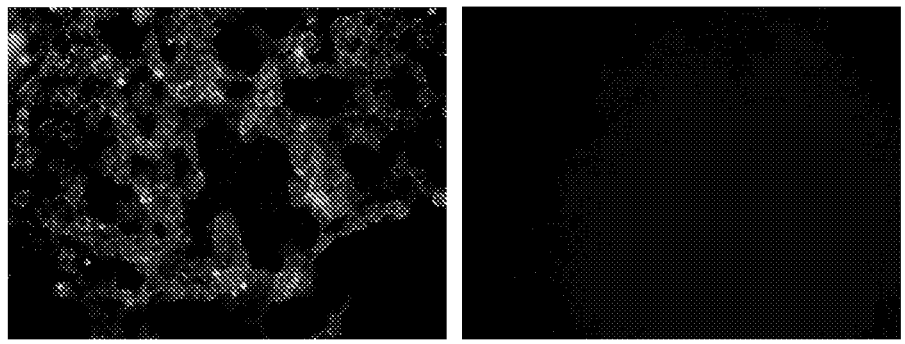
FIG. 4 shows that Cmyr-47 labeled with FIFC binds to NTCP expressing HEK293 cells ("NTCP-293") but does to bind to control HEK293 cells ("BLANK-293"). A polypeptide derived from heron HBV, labeled with FIFC, was used as a control polypeptide.
Figure 4:

To demonstrate that a polypeptide derived from HBV can bind to NTCP, various cell-lines expressing NTCP were treated with Cmyr-47. To visualize Cmyr-47, the polypeptide was labeled with FITC. Because NTCP expresses highly in the liver, primary hepatocytes from tupaia and human hepatocyte cell line HepG2 cells were prepared for the study. As shown in FIGS. 2A and 2B, FITC labeled Cmyr-47 binds to hepatocytes from two different species (FIG. 2A depicting binding of Cmyr-47 to tupaia primary hepatocytes; FIG. 2B depicting binding of Cmyr-47 to HepG2 cells). To demonstrate that Cmyr-47 specifically binds to NTCP, NTCP expressing L02 cells (NTCP-L02) were established by transfecting NTCP expressing vector. L02 cells transfected with a vector that does not express NTCP (BLANK-L02) were used as a negative control. As shown in FIG. 3, Cmyr-47 labeled with FITC binds to NTCP-L02 cells, but failed to bind to BLANK-L02 cells. To confirm the specificity of Cmyr-47, HEK293 cells, a cell-line that is not derived from the liver, were prepared for the study. NTCP expressing HEK293 cells (NTCP-293) were established by transfecting the cells with an NTCP expressing vector. HEK293 cells transfected with a control vector that does not express NTCP (BLANK-293) were used as a negative control. As shown in FIG. 4, Cmyr-47 labeled with FITC binds to NTCP-293 cells, but not BLANK-293 cells. In contrast, as expected based on a previous finding that an avian HBV does not infect mammals (Gripon et al., J. Virol. 79(3):1613-22 (2005)), a control polypeptide of 47 amino acid residues derived from heron HBV pre-S1 region (myristoylated-GLNQSTFNPLGFFPSHQLDPLFKA-NAGSADWDKNPNKDPW PQAHDTA-amidated, SEQ ID NO: 49) failed to bind to NTCP-293 cells. These results demonstrate that Cmyr-47 specifically binds to NTCP.

Example 1.3. In Vitro Bile Acids Assay of Cmyr-47

Figure 5:
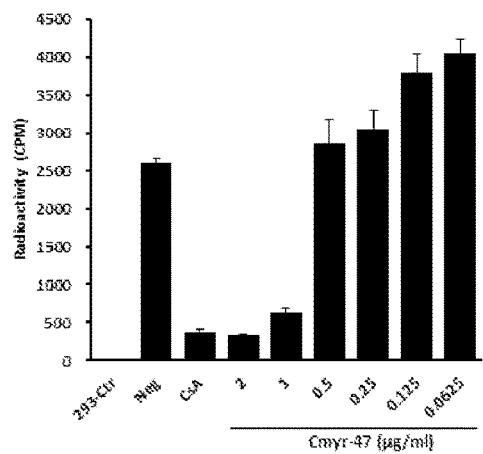
FIG. 5A shows the effect of Cmyr-47 on bile acids uptake in vitro. Cyclosporine A ("CsA") was used as a positive control.
FIG. 5B illustrates the bidirectional effect of Cmyr-47 on bile acids uptake.
FIGS. 5C and 5D show the effect of CsA on bile acids uptake in vitro and confirm the inhibitory effect of CsA.
FIGS. 5E and 5F show the effect of HBV-derived polypeptides on bile acids uptake in vitro at a low concentration molarly equivalent to 62.5 ng/ml (11.58 nmol/L) Cmyr-47 and at a high concentration molarly equivalent to 1 μg/ml (185.23 nmol/L) Cmyr-47, respectively.
Figure 5:
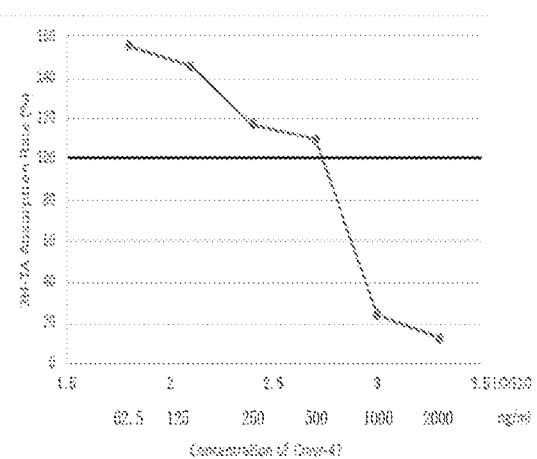
Figure 5:
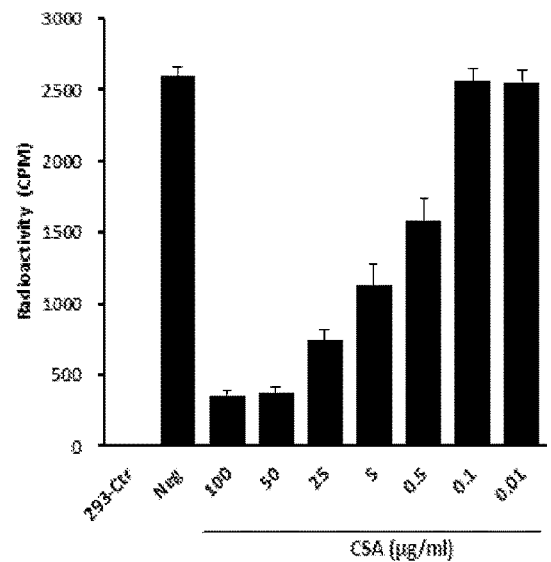
Figure 5:
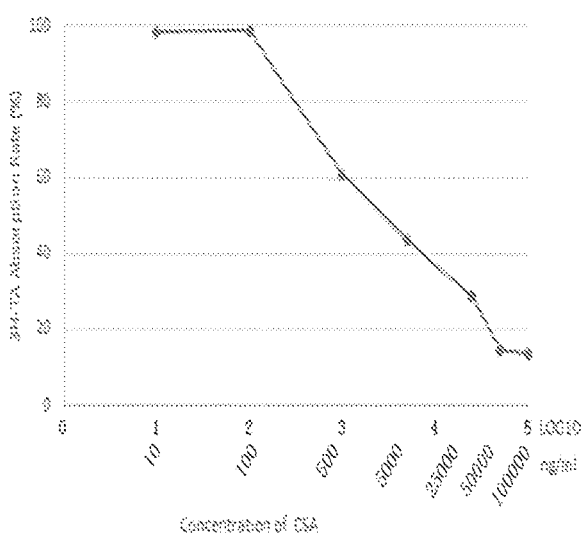
Figure 5:
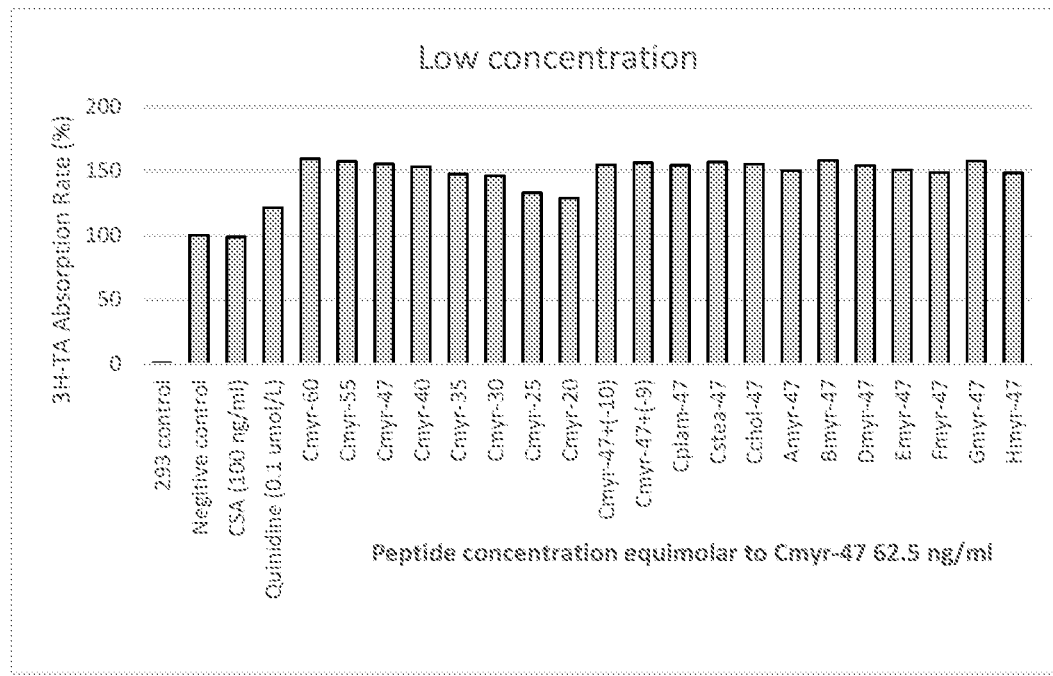
Figure 5:
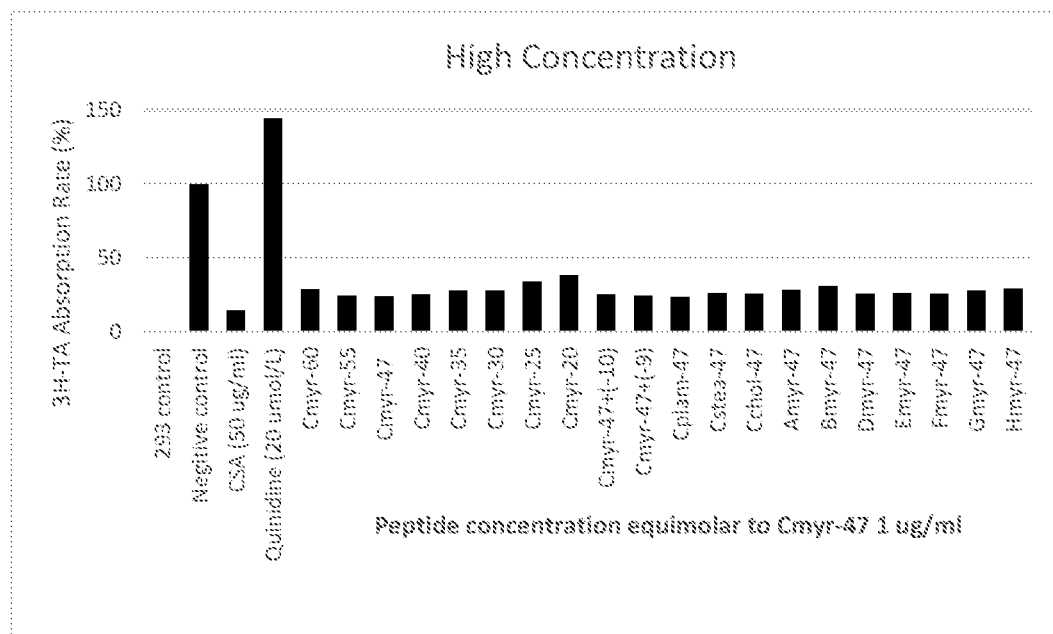

To further study the effect of the polypeptide derived from HBV on bile acids transport, NTCP-293 cells were incubated with bile acids labeled with $^3$H (3H-TA; taurocholate). By using $^3$H-TA, the amount of bile acids absorbed by the cells can be quantified by measuring the level of radioactivity of the cells. Since HEK293 cells are not capable of absorbing bile acids without NTCP expression, any bile acids taken up by NTCP-293 cells can be contributed to NTCP. TA at 10 umol/L (radioactively labeled as $^3$H-TA at 0.5 uCi/ml) and increasing amounts of Cmyr-47 were simultaneously added to cultured cells for 10 minutes. Cyclosporine A (CsA), known to inhibit bile acids transport, was used as a positive control at a concentration of 50 µM. As shown in FIG. 5A, compared with BLANK-293 cells, NTCP-293 cells were capable of absorbing a significant amount of bile acids. When NTCP-293 cells were treated with Cmyr-47, the uptake of bile acids was bidirectionally regulated at different concentrations of Cmyr-47. As shown in FIG. 5B, Cmyr-47 enhanced NTCP transport of bile acids into hepatocytes at a concentration at and below 500 ng/ml, while Cmyr-47 significantly reduced TA absorption at a concentration more than 500 ng/ml. Notably, 62.5 ng/ml of Cmyr-47 increased TA absorption by more than 50%, while 2 µg/ml of Cmyr-47 effectively inhibited the uptake of bile acids as compared with the positive control, CsA. Based on the escalating dose study shown in FIG. 5B, Cmyr-47 was determined to have an $IC_{50}$ value of 0.15 µM in blocking bile acids transport.

In contrast to bidirectional regulation of NTCP-mediated transport of bile acids by Cmyr-47, one-way inhibition of TA absorption was induced by CsA (FIGS. 5C and 5D). CsA did not enhance NTCP-mediated transportation of TA at either a low concentration of 10 ng/ml or a high concentration of 100 µg/ml. Based on the escalating dose study shown in FIG. 5D, the calculated $IC_{50}$ value of CsA for inhibiting bile acids transport was 3.05 µM.

Example 1.4. In Vitro Bile Acids Assay of Additional HBV-Derived Polypeptides

To further analyze the bidirectional effect of HBV-derived polypeptides on NTCP-mediated uptake of bile acids, two different concentrations (62.5 ng/ml as a representative low concentration and 1 µg/ml as a representative high concentration) of Cmyr-47 and other HBV-derived polypeptides were tested in the in vitro bile acids assay by following the protocol described above. Two control treatments, CsA and quinidine, were also tested for comparison. Quinidine is a class I antiarrhythmic agent and was previously shown to enhance NTCP-mediated TA uptake (see Kim et al, J. Pharmacol. Exp. Ther. 291(3): 1204-09 (1999)). CsA and quinidine were purchased from Sigma-Aldrich (Sigma-30024 and Sigma-Q3625, respectively).

As shown in FIG. 5E, CsA at 100 ng/ml had no significant effect on TA absorption, while quinidine enhanced TA absorption at 0.1 µmol/L. HBV-derived polypeptides listed in Table 1 (Cmyr-60, Cmyr-55, Cmyr-47, Cmyr-40, Cmyr-35, Cmyr-30, Cmyr-25, Cmyr-20, Cmyr-47+(-10), Cmyr-47+(-9), Cplam-47, Cstea-47, Cchol-47, Amyr-47, Bmyr-47, Dmyr-47, Emyr-47, Fmyr-47, Gmyr-47 or Hmyr-47) enhanced TA absorption at a low concentration molarly equivalent to 62.5 ng/ml (11.58 nmol/L) of Cmyr-47, confirming that HBV-derived polypeptides are capable of enhancing NTCP-mediated uptake of bile acids at a low concentration.

In contrast, when HBV-derived polypeptides (Cmyr-60, Cmyr-55, Cmyr-47, Cmyr-40, Cmyr-35, Cmyr-30, Cmyr-25, Cmyr-20, Cmyr-47+(-10), Cmyr-47+(-9), Cplam-47, Cstea-47, Cchol-47, Amyr-47, Bmyr-47, Dmyr-47, Emyr-47, Fmyr-47, Gmyr-47 or Hmyr-47) were tested at a higher concentration molarly equivalent to 1 µg/ml (185.23 nmol/L) of Cmyr-47, all the polypeptides effectively inhibited TA absorption (FIG. 5F), confirming that HBV-derived polypeptides are capable of inhibiting NTCP-mediated uptake of bile acids at a high certain concentration. For comparison, CsA at 50 µg/ml inhibited TA absorption, while quinidine at 20 µmol/L enhanced TA absorption. These results confirm that HBV-derived polypeptides are capable of bidirectionally regulating NTCP-mediated uptake of bile acids in a dose-dependent manner.

Example 2

Example 2.1. Toxicity and Bile Acids, Total Cholesterol, Triglyceride, and Glycemia Analysis of Rats Treated with Cmyr-47

To determine the toxicity of Cmyr-47 and confirm that Cmyr-47 can regulate bile acids uptake in vivo, 190 Sprague Dawley rats with equal number of males and females were subjected to a 6-month chronic toxicity test. Each rat was subcutaneously injected daily with either PBS as a control or Cmyr-47 of 1, 3, or 9 mg/kg for 180 days. The experimental scheme is shown in Table 2.

TABLE 2

Experimental Design Scheme of 180-Day Long Chronic Toxicity Test in Rats

| Group | Dosage/injection (mg · kg$^{-1}$) | Concentration (mg · ml$^{-1}$) | Clinic equivalent dosage multiplied by | Rats number (n) ♀ | Rats number (n) ♂ |
|---|---|---|---|---|---|
| I. Control | 0 | 0 | 0 | 20 | 20 |
| II. Low-dose | 1 | 0.4 | 2.3 | 20 + 5 | 20 + 5 |
| III. Middle-dose | 3 | 1.2 | 7.0 | 20 + 5 | 20 + 5 |
| IV. High-dose | 9 | 3.6 | 20.9 | 20 + 5 | 20 + 5 |

At the end of the experiment, a blood sample from each rat was collected by tail-bleeding. Serums from the blood samples were further separated out by centrifugation at 3,000 rpm for 10 min. The serum samples were then analyzed a total bile acid assay kit (Nanjing Jiancheng Bioengineering Institute) in order to determine the level of total bile acids (TBA). As shown in Tables 3 and 4, both female and male rats treated with Cmyr-47 displayed an increased level of total bile acids in the serum as compared with the control group, indicating that Cmyr-47 is capable of effectively blocking the bile acids uptake in vivo. The increase of total bile acids was dose-dependent.

TABLE 3

Serum TBA Concentrations of 180-Day Long Chronic Toxicity Test in Rats (Male, μM/L)

| Group | N | Mean | Std. Deviation | Std. Error | 95% Confidence Interval for Mean Lower Bound | 95% Confidence Interval for Mean Upper Bound | Minimum | Maximum |
|---|---|---|---|---|---|---|---|---|
| Control | 10 | 7.920 | 3.5401 | 1.5832 | 3.524 | 12.316 | 5.2 | 14.0 |
| Low-dose | 10 | 15.480 | 6.5975 | 2.9505 | 7.288 | 23.672 | 9.5 | 23.6 |
| Middle-dose | 10 | 17.240 | 8.3575 | 3.7376 | 6.863 | 27.617 | 11.1 | 30.9 |
| High-dose | 10 | 20.640 | 11.5881 | 5.1823 | 6.252 | 35.028 | 13.5 | 41.2 |

TABLE 4

Serum TBA Concentrations of 180-Day Long Chronic Toxicity Test in Rats (Female, μM/L)

| Group | N | Mean | Std. Deviation | Std. Error | 95% Confidence Interval for Mean Lower Bound | 95% Confidence Interval for Mean Upper Bound | Minimum | Maximum |
|---|---|---|---|---|---|---|---|---|
| Control | 10 | 13.180 | 3.4354 | 1.5364 | 8.914 | 17.446 | 7.8 | 16.8 |
| Low-dose | 10 | 16.460 | 5.1189 | 2.2892 | 10.104 | 22.816 | 11.1 | 22.5 |
| Middle-dose | 10 | 21.860 | 7.5477 | 3.3754 | 12.488 | 31.232 | 12.9 | 32.7 |
| High-dose | 10 | 26.800 | 15.4932 | 6.9288 | 7.563 | 46.037 | 13.8 | 51.0 |

Example 2.2. Total Cholesterol, Triglyceride, and Glycemia of Rats Treated with Cmyr-47

The levels of total cholesterol (TC), triglyceride (TG), and glycemia (GLU) of each animal tested in Example 2.1 are summarized in Tables 5 and 6. As shown in Tables 5 and 6, the low dose, middle dose, or high dose of Cmyr-47 had no significant effect on serum TC, TG or GLU, as compared with the control group (all values of P>0.05). Therefore, Cmyr-47 does not affect normal levels of serum TC, TG or GLU at physiological conditions.

TABLE 5

Serum TC, TG, GLU Concentrations of 180-Day Long Chronic Toxicity Test in Rats (Male, mmol/L, $\bar{\chi}$ ± SEM)

| Group | n | TC | TG | GLU |
| --- | --- | --- | --- | --- |
| Control | 10 | 1.62 ± 0.37 | 0.56 ± 0.20 | 7.15 ± 1.74 |
| Low-dose | 10 | 1.58 ± 0.21 | 0.61 ± 0.26 | 6.89 ± 1.24 |
| middle-dose | 10 | 1.5 ± 0.18 | 0.49 ± 0.18 | 6.76 ± 1.05 |
| High-dose | 10 | 1.58 ± 0.33 | 0.56 ± 0.26 | 6.69 ± 0.53 |

Note:
compared with normal control group,
P < 0.05,
P < 0.01;
compared with model control group,
*P < 0.05,
**P < 0.01

TABLE 6

Serum TC, TG, GLU Concentrations of 180-Day Long Chronic Toxicity Test in Rats (Female, mmol/L, $\bar{\chi}$ ± SEM)

| Group | n | TC | TG | GLU |
| --- | --- | --- | --- | --- |
| Control | 10 | 2.28 ± 0.54 | 0.78 ± 0.25 | 6.41 ± 0.38 |
| Low-dose | 10 | 1.97 ± 0.36 | 0.68 ± 0.33 | 6.34 ± 0.55 |
| middle-dose | 10 | 1.98 ± 0.49 | 0.75 ± 0.29 | 6.17 ± 0.69 |
| High-dose | 10 | 1.80 ± 0.50 | 0.56 ± 0.21 | 6.11 ± 0.42 |

Note:
compared with normal control group,
P < 0.05,
P < 0.01;
compared with model control group,
*P < 0.05,
**P < 0.01

Example 2.3. Toxicity and Bile Acids, Total Cholesterol, Triglyceride, and Glycemia Analysis of Dogs Treated with Cmyr-47

To further determine the toxicity of Cmyr-47 and confirm whether Cmyr-47 can regulate bile acids uptake in vivo, 56 Beagle dogs, with equal number of males and females, were subjected to a 9-month chronic toxicity test. Each dog was subcutaneously injected daily with either PBS as a control or Cmyr-47 of 0.25, 0.75, or 2 mg/kg per injection for 270 days. The experimental scheme is shown in Table 7.

TABLE 7

Experimental Design Scheme of 270-day Chronic Toxicity Test in Dogs

| | Group | Dosage/injection (mg · kg$^{-1}$) | Clinic equivalent dosage multiplied by | Dogs number (n) ♀ | ♂ |
| --- | --- | --- | --- | --- | --- |
| I. | Control | 0 | 0 | 7 | 7 |
| II. | Low-dose | 0.25 | 2 | 7 | 7 |
| III. | Middle-dose | 0.75 | 6 | 7 | 7 |
| IV. | High-dose | 2 | 16 | 7 | 7 |

At the end of the experiment, a blood sample from each dog was collected by vein puncture, and serum from the collected blood samples was separated as described above. The serum samples were then analyzed to determine the concentration of total bile acids levels as described above. As shown in Table 8, Cmyr-47 increased the serum level of total bile acids in dogs in a dose-dependent manner as compared with the control group. The levels of total cholesterol (TC), triglyceride (TG), and glycemia (GLU) of each animal are summarized in Table 9. As shown in Table 9, the low dose, middle dose, or high dose of Cmyr-47 had no significant effect on serum TC, TG or GLU, as compared with the control group (all values of P>0.05). Therefore, Cmyr-47 does not affect normal levels of serum TC, TG or GLU at physiological conditions.

TABLE 8

Serum TEA Concentration of 270-day Long Chronic Toxicity Test in Dogs for Day 91 Phased Detection (μM/L)

| | | Group | | | |
| --- | --- | --- | --- | --- | --- |
| Gender | Animal No. | control | Low-dose | Middle-dose | High-dose |
| Female | 1 | 2.6 | 3.2 | 2.4 | 2.1 |
| | 7 | 1.2 | 3.7 | 1.0 | 1.1 |
| | 3 | 1.0 | 7.8 | 1.0 | 20.4 |
| | 4 | 0.9 | 2.2 | 1.8 | 13.2 |
| | 5 | 1.0 | 2.3 | 4.1 | 4.2 |
| | 6 | 2.1 | 22.3 | 2.3 | 1.4 |
| | 7 | 1.6 | 3.0 | 2.9 | 7.3 |
| Male | 8 | 1.4 | 1.8 | 1.9 | 1.2 |
| | 9 | 1.7 | 1.7 | 2.1 | 1.7 |
| | 10 | 1.4 | 3.2 | 3.7 | 3.0 |
| | 11 | 0.8 | 2.9 | 1.2 | 1.3 |
| | 12 | 1.3 | 1.6 | 2.4 | 3.0 |
| | 13 | 0.8 | 1.1 | 15.3 | 5.9 |
| | 14 | 1.9 | 1.2 | 2.1 | 2.4 |
| | x ± s | 1.41 ± 0.53 | 4.14 ± 5.48 | 3.16 ± 3.61 | 4.87 ± 5.56 |
| | P value | — | 0.086 | 0.084 | 0.037 |

TABLE 9

Serum TC, TG, GLU Concentration of 270-day Long Chronic Toxicity Test in Dogs for Day 91 Phased Detection (mmol/L, $\bar{\chi}$ ± SEM)

| Group | n | TC | TG | GLU |
| --- | --- | --- | --- | --- |
| Control | 14 | 2.93 ± 0.66 | 0.39 ± 0.08 | 4.50 ± 0.68 |
| Low-dose | 14 | 3.07 ± 0.44 | 0.49 ± 0.13 | 4.26 ± 0.51 |

TABLE 9-continued

Serum TC, TG, GLU Concentration of 270-day Long Chronic Toxicity Test in Dogs for Day 91 Phased Detection (mmol/L, $\bar{\chi}$ ± SEM)

| Group | n | TC | TG | GLU |
|---|---|---|---|---|
| middle-dose | 14 | 3.20 ± 0.61 | 0.45 ± 0.10 | 4.52 ± 0.41 |
| High-dose | 14 | 3.16 ± 0.36 | 0.46 ± 0.12 | 4.69 ± 0.41 |

Note:

compared with normal control group,

P < 0.05,

P < 0.01;

compared with model control group,

*P < 0.05,

**P < 0.01

Example 2.4. Pharmacokinetic Analysis of Dogs Treated with Cmyr-47

Fifty-six Beagle dogs, with equal number of males and females, were subjected to a 1-month chronic toxicity test. Each dog was subcutaneously injected everyday with either PBS as a control or Cmyr-47 of 0.4, 1.2, or 3.6 mg/kg per injection for 30 days. The experimental scheme is shown in Table 10.

TABLE 10

Experimental Design Scheme of Pharmacokinetic Analysis in Dogs

| | Group | Dosage/injection (mg · kg$^{-1}$) | Dogs number (n) ♀ | ♂ |
|---|---|---|---|---|
| I. | Control | 0 | 3 | 3 |
| II. | Low-dose | 0.4 | 3 | 3 |
| III. | Middle-dose | 1.2 | 3 | 3 |
| IV. | High-dose | 3.6 | 3 | 3 |

During the experiment, blood samples from each dog was collected by vein puncture at 0, 10, 20, 40, 60, 90, 120, 180, 240, 360, 1440 min after the first dose and last dose. The serum from the collected blood samples was separated as described above. The serum samples were then analyzed to determine the concentration of Cmyr-47 by radioimmunoassay (RIA) using anti-PreS1 antibody 125E11 (Wei et al., Clinica. Chimica. Acta. 317:159-69 (2002)). Tables 11-13 show the serum concentrations of each animal administered with 0.4, 1.2, or 3.6 mg/kg, respectively. As shown in Table 13, dogs administered with 3.6 mg/kg of Cmyr-47 well tolerated the dosage and no serious toxicity was observed. The peak concentration (i.e. $C_{max}$) of Cmyr-47 in blood stream was reached at 20 minutes (i.e. $T_{max}$) following the administration. A $C_{max}$ refers to the peak serum concentration that a drug achieves after a dosing. A $T_{max}$ refers to the time at which the $C_{max}$ is observed. As shown in Table 13, for instance, the highest dose of Cmyr-47 was able to reach the $C_{max}$ of above 500 ng/ml at 20 minutes, indicating the $T_{max}$ of Cymr-47 is about 20 minutes in this test condition. As shown in Tables 11-13, only the highest dose, 3.6 mg/kg, was able to reach the peak concentration above 500 ng/ml.

TABLE 11

The serum Cmyr-47 concentration in Beagle dogs with sc 0.4 mg · kg − 1

| Time post dose | | Serum concentration of Cmyr-47 (ng · mL$^{-1}$) | | | | | | |
|---|---|---|---|---|---|---|---|---|
| | min | L7 | L8 | L9 | L10 | L11 | L12 | MEAN ± SD | CV % |
| FIRST DOSE | 0 | ND | ND | ND | ND | ND | ND | — | — |
| | 10 | 86.9 | 91.3 | 82.7 | 103.1 | 126.5 | 123.2 | 102.3 ± 18.8 | 18.4 |
| | 20 | 165.2 | 142.7 | 116.7 | 162.1 | 155.8 | 137.2 | 146.6 ± 18.3 | 12.5 |
| | 40 | 108.9 | 100.0 | 78.6 | 112.2 | 97.4 | 108.4 | 100.9 ± 12.3 | 12.2 |
| | 60 | 50.5 | 60.2 | 48.1 | 62.0 | 47.5 | 69.5 | 56.3 ± 8.9 | 15.9 |
| | 90 | 34.6 | 31.1 | 37.4 | 32.3 | 36.4 | 30.3 | 33.7 ± 2.9 | 8.7 |
| | 120 | 23.3 | 21.6 | 24.4 | 21.6 | 24.2 | 19.7 | 22.5 ± 1.8 | 8.1 |
| | 180 | 11.6 | 12.9 | 13.3 | 11.1 | 10.9 | 13.9 | 12.3 ± 1.2 | 10.1 |
| | 240 | 2.4 | 1.5 | 2.3 | 2.0 | 2.6 | 1.9 | 2.1 ± 0.4 | 17.7 |
| | 360 | 0.62 | 0.59 | 0.33 | 0.43 | 0.31 | 0.72 | 0.50 ± 0.17 | 33.7 |
| | 1440 | ND | ND | ND | ND | ND | ND | — | — |
| LAST DOSE | 0 | ND | ND | ND | ND | ND | ND | — | — |
| | 10 | 98.8 | 76.5 | 81.0 | 75.3 | 124.3 | 78.9 | 89.1 ± 19.2 | 21.6 |
| | 20 | 139.0 | 127.3 | 134.0 | 180.1 | 146.5 | 117.7 | 140.8 ± 21.7 | 15.4 |
| | 40 | 95.6 | 112.2 | 90.4 | 100.8 | 137.2 | 96.3 | 105.4 ± 17.2 | 16.3 |
| | 60 | 59.0 | 47.5 | 56.9 | 50.7 | 56.8 | 58.9 | 55.0 ± 4.8 | 8.6 |
| | 90 | 45.0 | 24.8 | 22.7 | 25.8 | 38.5 | 29.9 | 31.1 ± 8.8 | 28.4 |
| | 120 | 20.9 | 21.6 | 26.0 | 19.4 | 25.8 | 17.4 | 21.8 ± 3.5 | 15.8 |
| | 180 | 14.3 | 9.9 | 13.2 | 8.7 | 8.2 | 10.9 | 10.8 ± 2.5 | 22.7 |
| | 240 | 2.3 | 2.0 | 2.9 | 2.9 | 2.7 | 2.0 | 2.5 ± 0.4 | 16.8 |
| | 360 | 0.59 | 0.53 | 0.34 | 0.39 | 0.35 | 0.61 | 0.47 ± 0.12 | 26.3 |
| | 1440 | ND | ND | ND | ND | ND | ND | — | — |

Note:

ND = undetectable

TABLE 12

The serum Cmyr-47 concentration in Beagle dogs with sc 1.2 mg · kg − 1

| Time post dose | | Serum concentration of Cmyr-47 (ng · mL$^{-1}$) | | | | | | | |
|---|---|---|---|---|---|---|---|---|---|
| | min | M13 | M14 | M15 | M16 | M17 | M18 | MEAN ± SD | CV % |
| FIRST DOSE | 0 | ND | ND | ND | ND | ND | ND | — | — |
| | 10 | 289.9 | 340.3 | 249.3 | 374.1 | 272.9 | 327.2 | 308.9 ± 46.4 | 15.0 |
| | 20 | 433.6 | 450.2 | 365.0 | 540.9 | 457.4 | 422.1 | 444.9 ± 57.3 | 12.9 |
| | 40 | 333.9 | 323.0 | 259.9 | 314.5 | 287.1 | 292.8 | 302.0 ± 27.2 | 9.0 |
| | 60 | 140.9 | 166.6 | 180.7 | 127.3 | 123.3 | 198.5 | 156.2 ± 30.5 | 19.5 |
| | 90 | 90.6 | 108.9 | 113.2 | 82.4 | 78.9 | 122.6 | 99.4 ± 17.9 | 18.0 |
| | 120 | 57.2 | 67.4 | 54.3 | 70.9 | 50.2 | 61.0 | 60.2 ± 7.9 | 13.1 |
| | 180 | 41.8 | 35.2 | 31.6 | 38.6 | 33.9 | 49.0 | 38.3 ± 6.4 | 16.6 |
| | 240 | 5.6 | 2.2 | 7.0 | 7.9 | 4.5 | 6.6 | 5.6 ± 2.1 | 36.7 |
| | 360 | 2.0 | 1.6 | 1.8 | 2.2 | 1.6 | 1.9 | 1.8 ± 0.2 | 13.5 |
| | 1440 | ND | ND | ND | ND | ND | ND | — | — |
| LAST DOSE | 0 | ND | ND | ND | ND | ND | ND | — | — |
| | 10 | 300.6 | 301.8 | 235.7 | 335.3 | 305.4 | 344.9 | 304.0 ± 38.3 | 12.6 |
| | 20 | 374.1 | 418.2 | 327.2 | 492.8 | 407.6 | 392.8 | 402.1 ± 54.8 | 13.6 |
| | 40 | 300.9 | 279.6 | 235.7 | 283.7 | 266.3 | 259.9 | 271.0 ± 22.4 | 8.3 |
| | 60 | 128.1 | 149.5 | 162.1 | 112.5 | 109.0 | 170.9 | 138.7 ± 26.0 | 18.8 |
| | 90 | 79.1 | 90.9 | 90.5 | 71.6 | 68.6 | 108.3 | 84.8 ± 14.8 | 17.4 |
| | 120 | 51.0 | 59.9 | 48.3 | 63.4 | 45.0 | 54.3 | 53.6 ± 7.0 | 13.1 |
| | 180 | 37.4 | 30.5 | 27.2 | 34.8 | 29.0 | 41.8 | 33.4 ± 5.6 | 16.7 |
| | 240 | 3.3 | 4.7 | 5.7 | 6.9 | 5.1 | 4.5 | 5.0 ± 1.2 | 23.7 |
| | 360 | 1.7 | 1.4 | 1.6 | 2.0 | 1.4 | 1.7 | 1.6 ± 0.2 | 13.4 |
| | 1440 | ND | ND | ND | ND | ND | ND | — | — |

Note:
ND = undetectable

TABLE 13

The serum Cmyr-47 concentration in Beagle dogs with sc 3.6 mg · kg − 1

| Time post dose | | Serum concentration of Cmyr-47 (ng · mL$^{-1}$) | | | | | | | |
|---|---|---|---|---|---|---|---|---|---|
| | min | H19 | H20 | H21 | H22 | H23 | H24 | MEAN ± SD | CV % |
| FIRST DOSE | 0 | ND | ND | ND | ND | ND | ND | — | — |
| | 10 | 617.8 | 510.6 | 739.4 | 542.7 | 569.9 | 697.1 | 612.9 ± 89.8 | 14.7 |
| | 20 | 958.4 | 739.4 | 698.7 | 1117.3 | 1206.0 | 849.6 | 928.2 ± 204.1 | 22.0 |
| | 40 | 810.7 | 620.0 | 739.4 | 646.3 | 840.6 | 543.6 | 700.1 ± 116.0 | 16.6 |
| | 60 | 305.4 | 344.9 | 340.4 | 382.7 | 425.0 | 286.4 | 347.5 ± 50.6 | 14.6 |
| | 90 | 218.9 | 237.5 | 262.8 | 201.9 | 190.3 | 187.4 | 216.5 ± 29.5 | 13.6 |
| | 120 | 132.9 | 109.0 | 156.0 | 117.0 | 148.5 | 90.7 | 125.7 ± 124.8 | 19.7 |
| | 180 | 68.5 | 44.5 | 83.2 | 56.9 | 75.4 | 66.0 | 65.8 ± 13.7 | 20.8 |
| | 240 | 12.8 | 16.2 | 11.2 | 15.0 | 10.1 | 13.2 | 13.1 ± 2.3 | 17.4 |
| | 360 | 3.1 | 3.3 | 2.6 | 3.5 | 3.0 | 3.1 | 3.1 ± 0.3 | 9.6 |
| | 1440 | ND | ND | ND | ND | ND | ND | — | — |
| LAST DOSE | 0 | ND | ND | ND | ND | ND | ND | — | — |
| | 10 | 543.6 | 433.2 | 635.1 | 490.3 | 501.2 | 588.1 | 531.9 ± 72.6 | 13.6 |
| | 20 | 874.7 | 673.9 | 620.0 | 921.7 | 1129.9 | 746.1 | 827.7 ± 187.5 | 22.7 |
| | 40 | 730.7 | 545.5 | 674.4 | 562.1 | 746.4 | 493.1 | 625.4 ± 105.9 | 16.9 |
| | 60 | 272.3 | 293.4 | 272.8 | 343.2 | 394.0 | 252.8 | 304.7 ± 53.6 | 17.6 |
| | 90 | 195.9 | 209.4 | 236.5 | 173.7 | 197.5 | 166.2 | 196.5 ± 25.3 | 12.9 |
| | 120 | 112.5 | 92.2 | 132.9 | 104.5 | 127.9 | 97.2 | 111.2 ± 16.4 | 14.8 |
| | 180 | 53.6 | 25.9 | 72.2 | 56.0 | 70.3 | 53.6 | 55.3 ± 16.7 | 30.1 |
| | 240 | 10.9 | 13.8 | 10.0 | 13.2 | 8.6 | 11.7 | 11.4 ± 1.9 | 17.0 |
| | 360 | 2.4 | 3.6 | 2.4 | 3.2 | 3.2 | 2.8 | 2.9 ± 0.5 | 16.3 |
| | 1440 | ND | ND | ND | ND | ND | ND | — | — |

Note:
ND = undetectable

Example 3

Example 3.1. Methods and Materials in Treatment of Hyperlipidemic Golden Hamster Model with Cmyr-47

To analyze the in vivo effects of Cmyr-47 on lipid metabolism, a hyperlipidemic golden hamster model was established by feeding hamsters with a high-fat diet for 2 weeks (after adaptive feeding for 10 days). Male Golden hamsters (N=70, 90-110 g) were purchased from Beijing Vital River (SCXK (Jing) 2012-0001) with animal quality certificate number 11400700093338. Animals were housed at 23±1° C. with 50-70% humidity under a 12 hour light: dark cycle (150-200 Lx), in a noise-controlled room (<50 dB) at the Zhejiang Traditional Chinese Medicine University Animal Experimental Research Center (SYXK (Zhe) 2013-0184). The composition of the high-fat diet included 1.25% cholesterol and 20.06% fat (soybean oil 2.79%, cocoa butter 17.27%) and the diet was purchased from Research Diets Inc. (New Brunswick, N.J.) and stored at 4° C. As a normal non-hyperlipidemic control ("a normal control group"), a group of golden hamsters was fed with a regular chow diet. A full nutritional rat pellet was used as a normal chow diet after sterilization with $Co^{60}$ irradiation. Animals were provided with filtered and sterilized tap water ad libitum. All food was available ad libitum and animals were housed 4 to 5 per cage. Weight and food consumption of each hamster fed with the high-fat diet was monitored on a weekly basis. All animals were treated humanely and care was taken to minimize pain and suffering in accordance with the principle of the 3Rs (replacement, reduction, and refinement).

After 2 weeks of the high-fat diet treatment, the hyperlipidemic phenotype of hamsters was confirmed when the animals had serum total cholesterol (TC) levels higher than 10 mmol/L. A total of 40 hyperlipidemic hamsters were randomly stratified into 5 groups (N=8/group): a model control group (10 mL/kg PBS, subcutaneous administration (sc)), a positive treatment control group (fenofibrate, 50 mg/kg/day, peroral intragastrical administration (po)), a low-dose treatment group (Cmyr-47, 10 mg/kg/day, sc), a high-dose treatment group (30 mg/kg/day Cmyr-47, sc), and a CsA treatment group (CsA, 5 mg/kg/day, po). 10 hamsters fed with the normal chow diet were used as a normal control group (10 mL/kg PBS, sc).

By following the protocol described above, Cmyr-47 was synthesized as a white powder by HEP Pharmaceutical (Shanghai, China; Lot number: 14011801). For each treatment, Cmyr-47 was freshly prepared in PBS and used immediately after preparation. PBS was prepared by formulating a 20×PB solution ($Na_2HPO_4.12H_2O$ (64.4652 g) and $NaH_2PO_4.2H_2O$ (3.1202 g) in water to 500 mL). Then, 1 volume of 20×PB, 4 volumes of pure water, and 15 volumes of 0.9% normal saline were mixed together to obtain PBS for dissolving the test drug. Fenofibrate (FENO) of Fenolip tablet used as a positive control in this study was purchased from Laboratoires FOURNIER S.A. CsA (Sandimmune®) was purchased from Novartis.

PBS, Cmyr-47, FENO, and CsA were respectively administered for 4 consecutive weeks. During the experiment, all animals in the model control group, low and high dose group, and positive control group were fed with the high fat diet while the normal control group was fed with the normal chow diet. Cmyr-47 or PBS was subcutaneously injected to the hamsters twice a day (9:00-10:00 in the morning and 16:00-17:00 in the afternoon). A positive treatment control group was provided with FENO via peroral intragastrical administration. A CsA treatment group was provided with CsA via peroral intragastrical administration. Each morning, food and water consumption, feces, and animal grooming were monitored. All animals were weighed weekly.

After 2 weeks of treatment, serum TC and triglycerides (TG) levels of all animals were measured. After 4 weeks of treatment, serum TC, TG, LDL-C, and HDL-C levels of all animals were measured. Prior to measurement, all animals were fasted for 12 h with an access to water prior to blood collection. A blood (0.3 mL) sample from each animal was obtained via retro-orbital plexus and serums from the samples were further isolated by centrifugation at 3,000 rpm for 10 min. Kits for measuring lipids were purchased from Shenneng DESAY Diagnostic Technology Co. Ltd. (Shanghai, China) and all measurements were conducted by following the manufacturer's protocols. 7020 automatic biochemical analyzer was used for the measurements. An atherosclerosis index (AI) of each animal was calculated by following the formula of AI=(TC−HDL-C)/HDL-C. The AI is considered as one of the most reliable indicators of an increased risk developing atherosclerosis.

An SQP Electronic scale from Sartorius Scientific Instruments Co., Ltd. (Beijing, China) was used, as was a MLS-3750 high pressure sterilizing chamber from Sanyo Company (Japan). An RO-MB-50 Ultrapure water system was from Yongjieda Purification Technology Co. Ltd. (Hangzhou, Zhejiang, China). KQ-300DE ultrasound was purchased from Kunshan Ultrasonic Instrument Co., Ltd. (Kunshan, Jiangsu, China) and a Hitachi 7020 automatic biochemical analyzer from Hitachi Ltd. (Japan). The multifunctional ELISA machine was from Thermo Fisher Scientific Inc. (USA).

SPSS19.0 software was used to analyze data, expressed as means±standard deviation or mean±SEM. ANOVA variance analysis was used to evaluate the data from the test results. LSD test was used for pairwise comparisons. Values of the statistical analyses were rounded to 2 decimal places.

Example 3.2. Effect of Cmyr-47 and Additional Polypeptides Derived from HBV on Serum Total Cholesterol (TC)

Figure 6:
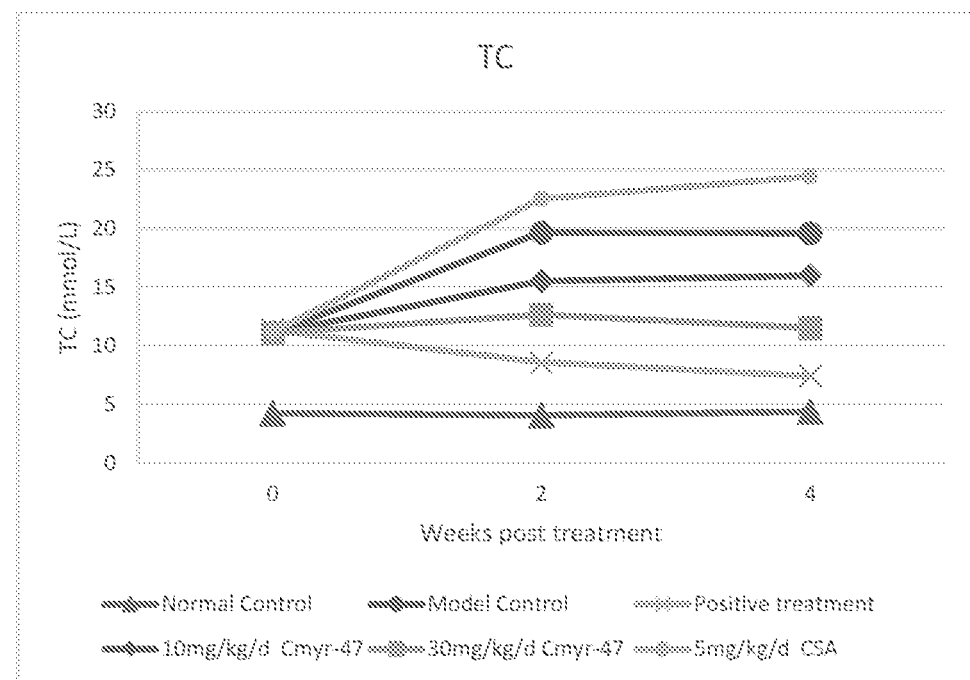
FIG. 6 shows the changes of serum total cholesterol ("TC") in hyperlipidemic golden hamsters treated with Cmyr-47 or CsA for 4 weeks. Golden hamsters fed with regular diet were treated with PBS and used as a "Normal Control" while hyperlipidemic golden hamsters treated with PBS were used as a "Model Control." Hyperlipidemic golden hamsters treated with Fenofibrate ("Positive Treatment") were used as a positive control.

As shown in Table 14 and FIG. 6, the serum TC levels in the model controls were significantly higher than those in the normal controls during the experiment, confirming that the animals fed with the high-fat diet were hyperlipidemic (all values of P<0.01). The administration of FENO significantly lowered the serum TC levels as compared with the model control group (all of P values less than 0.01). Hyperlipidemic animals treated with Cmyr-47 also displayed lower serum TC levels than the model control group, and the effect of Cmyr-47 was dose-dependent. In contrast, hyperlipidemic animals treated with CsA showed significantly elevated serum TC levels as compared with the model control group.

TABLE 14

Effect of Cmyr-47 on Serum TC (mmol/L, $\bar{\chi} \pm S$)

| | | | | TC level after weeks of dosing | |
|---|---|---|---|---|---|
| Group | Dosage/injection | n | Before dosing | 2 w | 4 w |
| Normal control | 10 mL/kg PBS | 10 | 4.25 ± 0.41 | 4.09 ± 0.34 | 4.39 ± 0.43 |
| Model control | 10 mL/kg PBS | 8 | 11.12 ± 0.47[##] | 19.67 ± 4.05[##] | 19.58 ± 4.72[##] |
| Positive control | 50 mg/kg FENO | 8 | 11.34 ± 0.50 | 6.63 ± 4.40** | 7.42 ± 1.70** |

TABLE 14-continued

Effect of Cmyr-47 on Serum TC (mmol/L, $\bar{\chi} \pm S$)

| Group | Dosage/injection | n | Before dosing | TC level after weeks of dosing | |
|---|---|---|---|---|---|
| | | | | 2 w | 4 w |
| Low-dose | 10 mg/kg Cmyr-47 | 8 | 11.10 ± 0.44 | 15.53 ± 4.51* | 16.00 ± 5.17* |
| High-dose | 30 mg/kg Cmyr-47 | 8 | 11.10 ± 0.46 | 12.67 ± 2.98** | 11.54 ± 1.67** |
| CsA treatment | 5 mg/kg CsA | 8 | 11.24 ± 0.40 | 22.53 ± 2.50 | 24.46 ± 3.35* |

Note:
compared with normal control group,
P < 0 05,
P < 0.01;
compared with model control group,
*P < 0.05,
**P < 0.01

Additional polypeptides derived from HBV listed in Table 1 were also tested to confirm their effects on serum TC in vivo. The experiment was conducted by following the same experimental protocol described above. All polypeptide was administrated at a dose molarly equivalent to 30 mg/kg/day of Cmyr-47.

also significantly lowered the serum TG levels in the animals as compared with the model controls. Similar to the effect on serum TC, the effect of Cmyr-47 on serum TG were also dose-dependent. Of note, CsA treatment increased the serum TG levels in the animals as compared with the model controls.

TABLE 15

Effect of Cmyr-47 on Serum TG (mmol/L, $\bar{\chi} \pm S$)

| Group | Dosage/injection | n | Before dosing | TG level after weeks of dosing | |
|---|---|---|---|---|---|
| | | | | 2 w | 4 w |
| Normal control | 10 mL/kg PBS | 10 | 2.85 ± 1.24 | 2.23 ± 0.76 | 2.29 ± 0.84 |
| Model control | 10 mL/kg PBS | 8 | 5.65 ± 1.78## | 7.81 ± 3.24## | 7.54 ± 3.10## |
| Positive Control | 50 mg/kg FENO | 8 | 6.16 ± 1.30 | 3.14 ± 0.4** | 2.68 ± 0.30** |
| Low-dose | 10 mg/kg Cmyr-47 | 8 | 6.15 ± 1.14 | 6.29 ± 2.48 | 4.39 ± 1.21 |
| High-dose | 30 mg/kg Cmyr-47 | 8 | 6.35 ± 2.00 | 5.31 ± 1.76* | 3.81 ± 0.95* |
| CsA treatment | 5 mg/kg CsA | 8 | 6.23 ± 0.90 | 8.81 ± 0.50 | 10.23 ± 0.61** |

Note:
compared with normal control,
P < 0.05,
P < 0.01;
compared with model control,
*P < 0.05,
**P < 0.01

Figure 7:
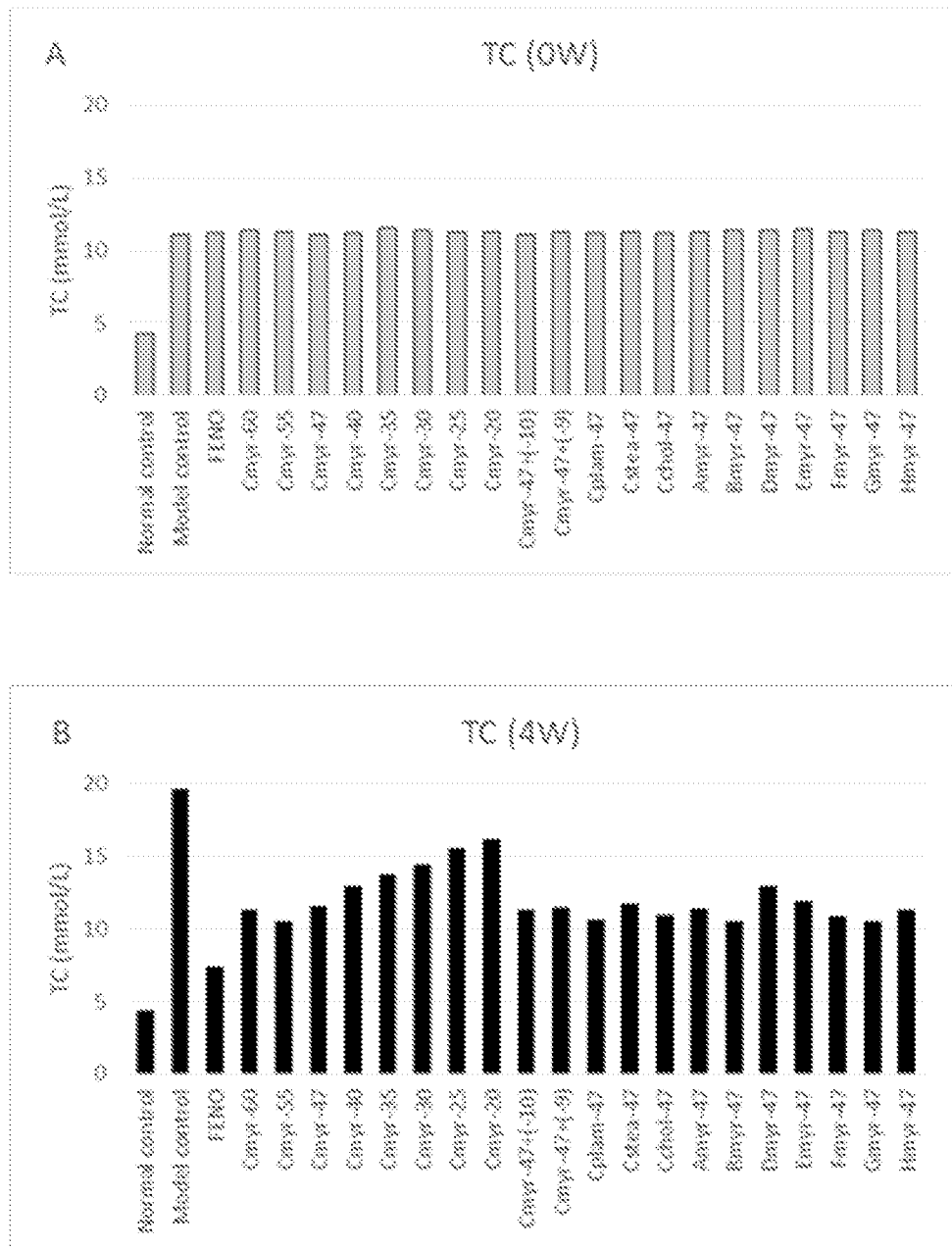
FIG. 7A shows the level of serum TC prior to treatments with polypeptides derived from HBV.
FIG. 7B shows the level of serum TC after 4 weeks of the treatments.

FIGS. 7A and 7B confirmed that animals fed with the high-fat diet were hyperlipidemic (compare the serum TC levels of normal controls and model controls). As previously shown, FENO was capable of decreasing the serum TC levels in the animals. At week 4, animals treated with other HBV-derived peptides (Cmyr-60, Cmyr-55, Cmyr-40, Cmyr-35, Cmyr-30, Cmyr-25, Cmyr-20, Cmyr-47+(-10), Cmyr-47+(-9), Cplam-47, Cstea-47, Cchol-47, Amyr-47, Bmyr-47, Dmyr-47, Emyr-47, Fmyr-47, Gmyr-47 or Hmyr-47) also showed lower serum TC levels than that of the model controls.

Example 3.3. Effect of Cmyr-47 and Additional Polypeptides Derived from HBV on Serum Triglycerides (TG)

Figure 8:
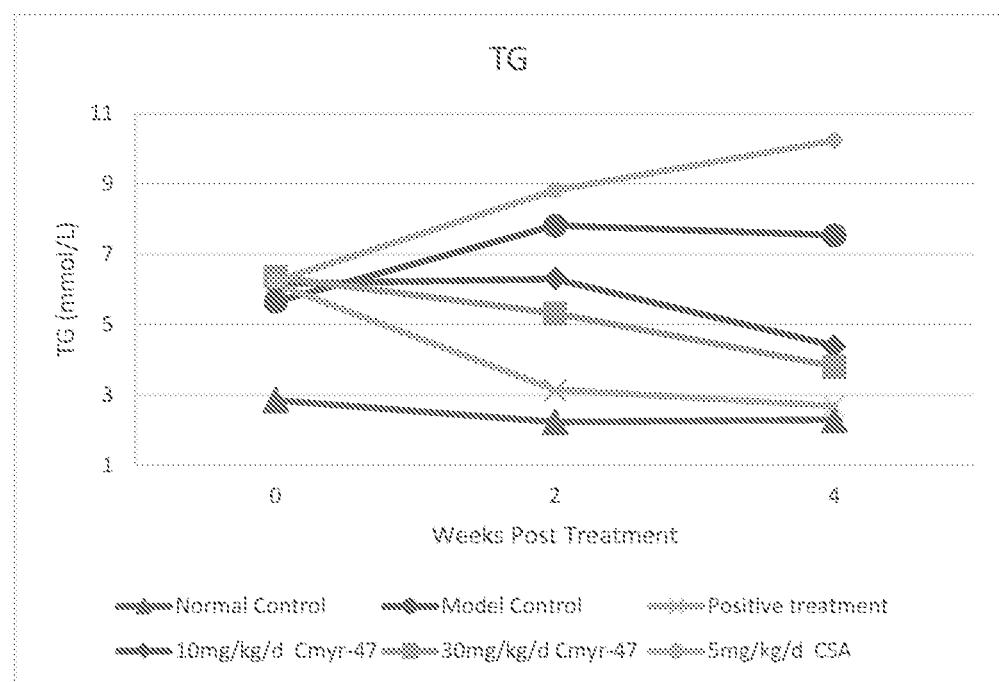
FIG. 8 depicts the changes of serum triglycerides ("TG") of hyperlipidemic golden hamsters during 4 weeks of Cmyr-47 treatment.

As shown in Table 15 and FIG. 8, the serum TG levels in the model controls were significantly higher than the normal controls throughout the experiment (all values of P<0.01). Measurements at week 2 and week 4 confirmed that FENO significantly decreased the serum TG levels in the animals (all of P values less than 0.01). The high dose of Cmyr-47

Figure 9:
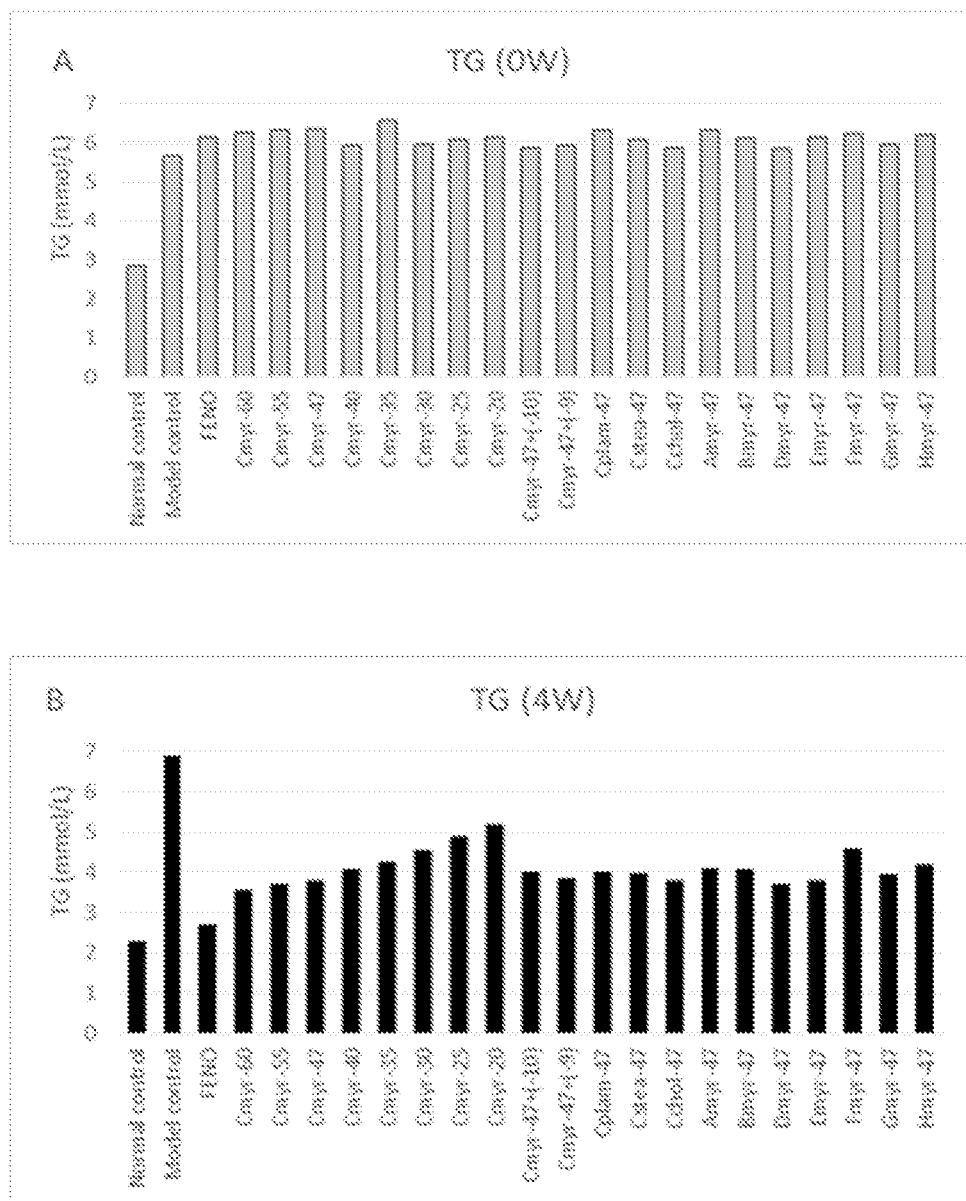
FIG. 9A shows the level of serum TG prior to treatments with polypeptides derived from HBV.
FIG. 9B shows the level of serum TG after 4 weeks of the treatments.

The serum TG levels of animals treated with additional polypeptides derived from HBV (Cmyr-60, Cmyr-55, Cmyr-40, Cmyr-35, Cmyr-30, Cmyr-25, Cmyr-20, Cmyr-47+(-10), Cmyr-47+(-9), Cplam-47, Cstea-47, Cchol-47, Amyr-47, Bmyr-47, Dmyr-47, Emyr-47, Fmyr-47, Gmyr-47 or Hmyr-47) were also measured by following the protocol described above. As shown in FIGS. 9A and 9B, the serum TG levels of animals treated with these HBV-derived polypeptides were lower than that of the model controls, indicating all the tested polypeptides derived from HBV are capable of lowering serum TG in vivo.

Figure 10:
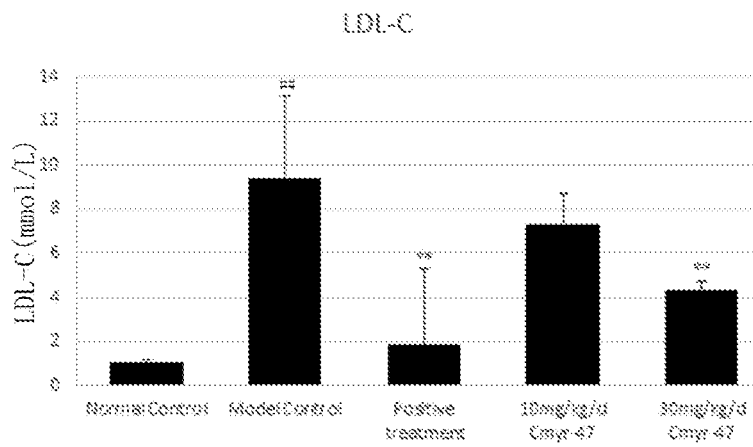
FIG. 10 depicts the level of serum LDL-C of hyperlipidemic golden hamsters after 4 weeks of Cmyr-47 treatment.

Example 3.4. Effect of Cmyr-47 and Additional Polypeptides Derived from HBV on Serum LDL-C Table 16 and FIG. 10 summarize the measurements of serum LDL-C levels from the animals treated with PBS, FENO, or Cmyr-47. As expected, the serum LDL-C levels in the model controls significantly increased as compared with the normal controls, confirming the hyperlipidemic phenotype (P<0.01). The positive controls treated with FENO displayed significantly lower serum LDL-C levels than the model controls. Consistent with the effect of Cmyr-47 on serum TC and TG, animals treated with Cmyr-47 (particularly with the high dose of 30 mg/kg) showed significantly decreased serum LDL-C levels as compared with the model controls.

TABLE 16

Effect of Cmyr-47 on Serum LDL-C
(4 weeks post the treatment)

| Group | Dosage/injection | n | LDL-C (mmol/L) |
|---|---|---|---|
| Normal control | 10 mL/kg PBS | 10 | 1.09 ± 0.11 |
| Model control | 10 mL/kg PBS | 8 | 9.38 ± 3.75## |
| Positive Control | 50 mg/kg FENO | 8 | 1.88 ± 0.40** |
| Low-dose | 10 mg/kg Cmyr-47 | 8 | 7.33 ± 3.40 |
| High-dose | 30 mg/kg Cmyr-47 | 8 | 4.34 ± 1.36** |

Figure 11:
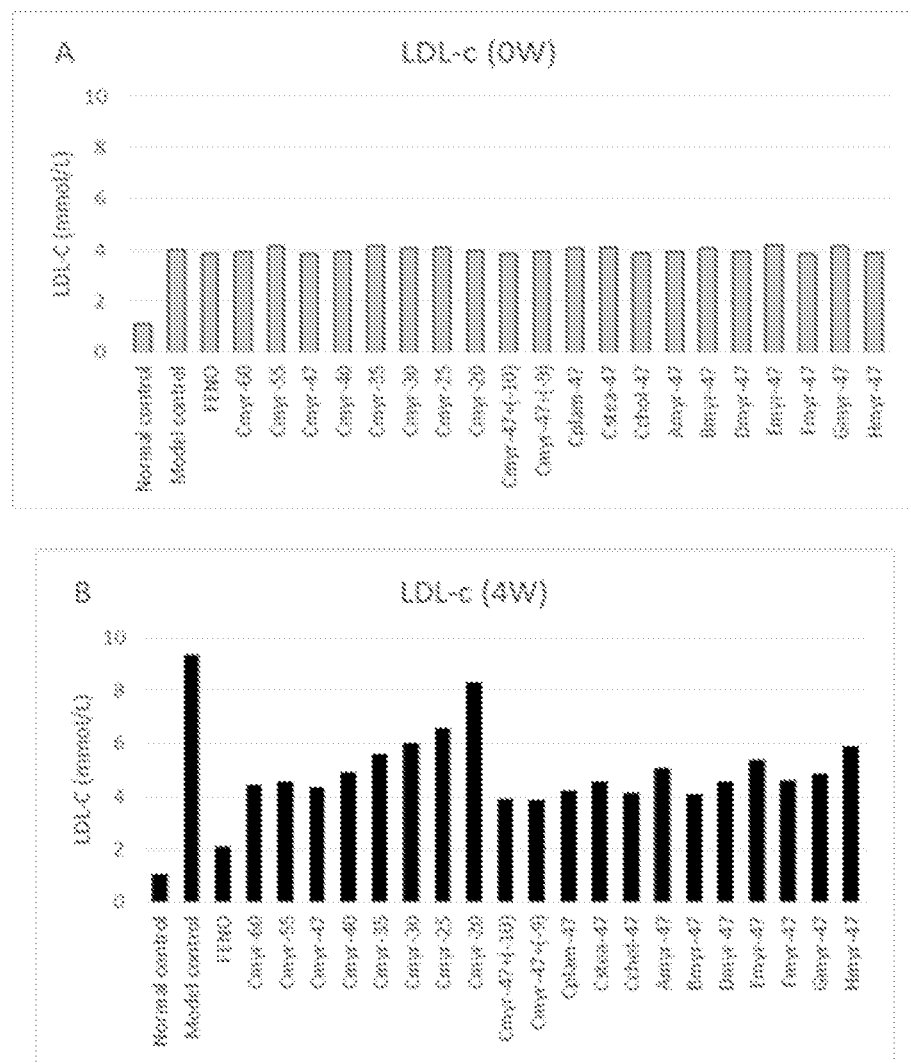
FIG. 11A shows the level of serum LDL-C before being treated with polypeptides derived from HBV.
FIG. 11B shows the level of serum LDL-C after 4 weeks of the treatments.

Note:
compared with normal control,
$p < 0.05$,
$p < 0.01$;
compared with model control,
*$p < 0.05$,
**$p < 0.01$ The serum LDL-C levels of animals treated with additional polypeptides derived from HBV (Cmyr-60, Cmyr-55, Cmyr-40, Cmyr-35, Cmyr-30, Cmyr-25, Cmyr-20, Cmvr-47+(-10), Cmyr-47+(-9), Cplam-47, Cstea-47, Cchol-47, Amyr-47, Bmyr-47, Dmyr-47, Emyr-47, Fmyr-47, Gmyr-47 or Hmyr-47) were also measured by following the protocol described above. As shown in FIGS. 11A and 11B, the serum LDL-C levels of those animals were lower than that of the model controls.

Example 3.5. Effect of Cmyr-47 on Serum HDL-C and AI

Figure 12:
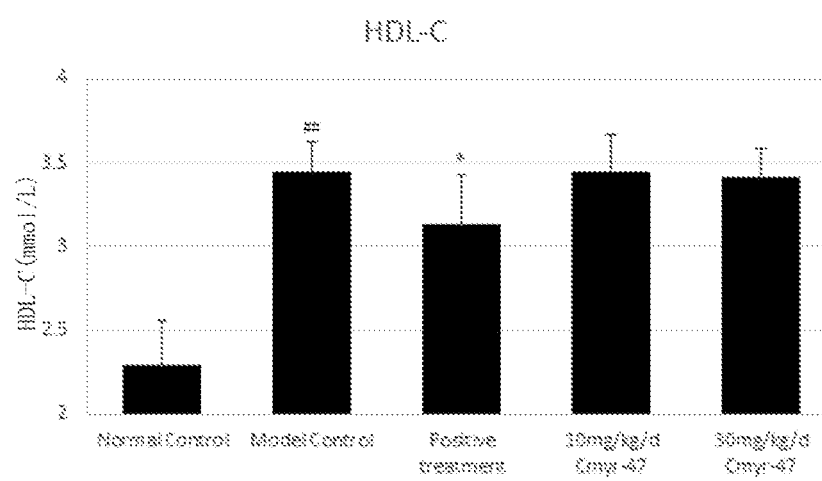
FIG. 12 shows the level of serum HDL-C of hyperlipidemic golden hamsters after 4 weeks of Cmyr-47 treatment.
Figure 13:
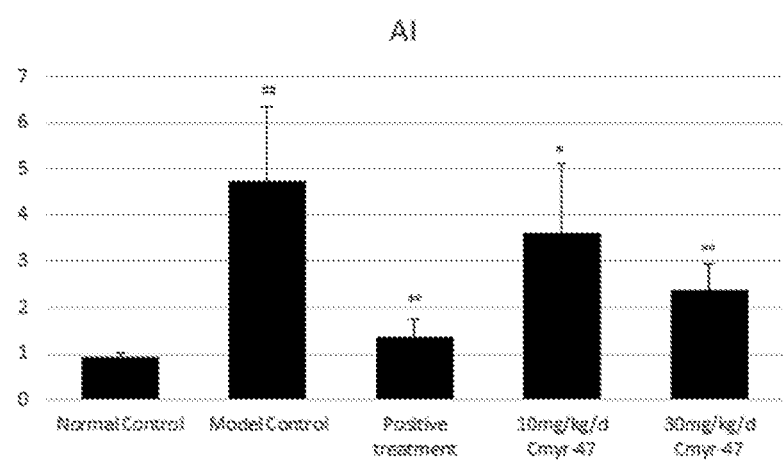
FIG. 13 depicts atherosclerosis index ("AI") of hyperlipidemic golden hamsters after 4 weeks of Cmyr-47 treatment.

Table 17 and FIG. 12 provide the measurements of serum HDL-C levels. Based on the values obtained in this study, an AI value of each animal was calculated by following the formula discussed above. The average AI value of each group is provided in Table 17 and FIG. 13. Although Cmyr-47 did not lower serum HDL-C in vivo, the average AI value of animals treated with Cmyr-47 was significantly lower than the average value of the model controls, indicating that Cmyr-47 may be protective against atherosclerosis and other vascular disease including cardiovascular diseases that are caused by accumulation of fat.

TABLE 17

Effect of Cmyr-47 on Serum HDL-C and AI
(4 weeks post the treatment)

| Group | Dosage/injection | n | HDL-C (mmol/L) | AI |
|---|---|---|---|---|
| Normal control | 10 mL/kg PBS | 10 | 2.29 ± 0.27 | 0.92 ± 0.11 |
| Model control | 10 mL/kg PBS | 8 | 3.44 ± 0.19## | 4.75 ± 1.59## |
| Positive Control | 50 mg/kg FENO | 8 | 3.13 ± 0.30** | 1.36 ± 0.38** |
| Low-dose | 10 mg/kg Cmyr-47 | 8 | 3.45 ± 0.22 | 3.62 ± 1.49* |
| High-dose | 30 mg/kg Cmyr-47 | 8 | 3.41 ± 0.18 | 2.39 ± 0.55** |

Note:
compared with normal control,
$p < 0.05$,
$p < 0.01$;
compared with model control,
*$p < 0.05$,
**$p < 0.01$ Example 3.6. Effect of Cmyr-47 on Serum Total Bile Acid (TBA)

Figure 14:
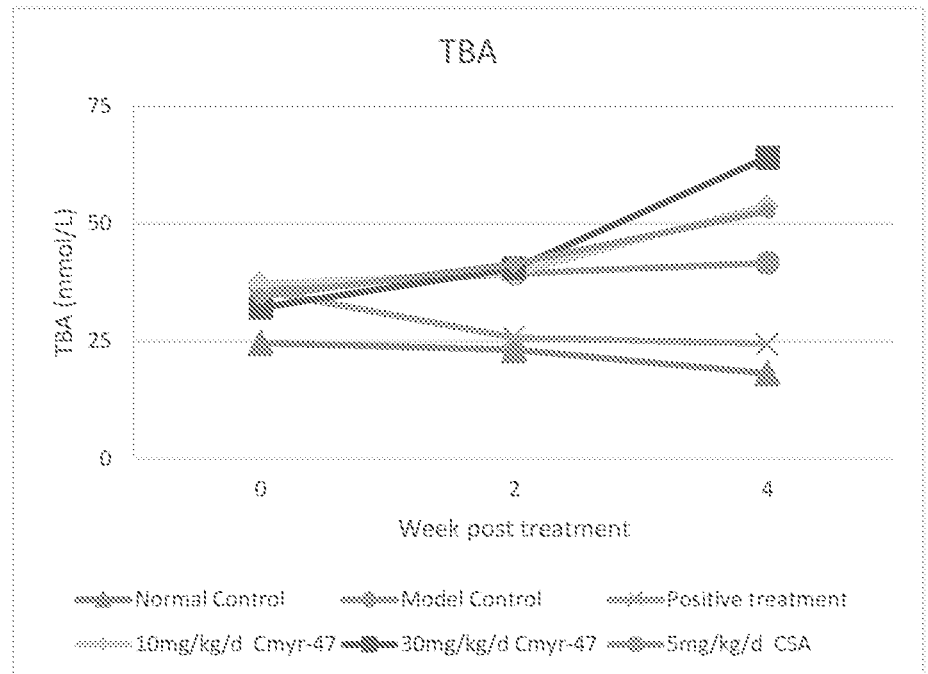
FIG. 14 shows the changes of serum total bile acids (TBA) of hyperlipidemic golden hamsters after 4 weeks of Cmyr-47 treatment. Fenofibrate and CsA were also tested for comparison.

Table 18 and FIG. 14 provide the measurements of serum TBA levels. As expected, the serum TBA levels in the model controls were higher than the normal controls. As compared with the model control group, the serum TBA levels of animals treated with Cmyr-47 were further elevated in a dose-dependent fashion, confirming that Cmyr-47 is capable of inhibiting bile acid uptake in vivo. Measurements at week 4 confirmed that the high dose of Cmyr-47 significantly increased the serum TBA levels (P values less than 0.05). CsA and the low dose of Cmyr-47 also moderately elevated the serum TBA levels after 4 weeks of treatment, though the significance was not reached.

TABLE 18

Effect of Cmyr-47 on Serum TBA (mmol/L, $\bar{\chi}$ ± S)

| Group | Dosage/injection | n | Before dosing | TG level after weeks of dosing | |
|---|---|---|---|---|---|
| | | | | 2 w | 4 w |
| Normal control | 10 mL/kg PBS | 10 | 24.61 ± 3.69 | 23.14 ± 2.65 | 18.13 ± 3.81 |
| Model control | 10 mL/kg PBS | 8 | 36.19 ± 7.00 | 39.35 ± 12.04## | 41.63 ± 18.61## |
| Positive Control | 50 mg/kg FENO | 8 | 35.74 ± 4.47 | 25.74 ± 4.25* | 24.45 ± 2.52* |
| Low-dose | 10 mg/kg Cmyr-47 | 8 | 37.28 ± 7.55 | 39.42 ± 11.18 | 53.94 ± 32.15 |
| High-dose | 30 mg/kg Cmyr-47 | 8 | 32.15 ± 7.82 | 40.43 ± 5.96 | 64.08 ± 5.47* |
| CsA treatment | 5 mg/kg CSA | 8 | 34.55 ± 6.67 | 41.38 ± 11.83 | 52.73 ± 9.83 |

Note:
compared with normal control,
$p < 0.05$,
$p < 0.01$;
compared with model control,
*$p < 0.05$,
**$p < 0.01$

Example 3.7. Effect of Cmyr-47 on Serum Glucose (GLU)

As shown in Table 19, hyperlipidemic animals did not show any significant hyperglycemic phenotype as compared with the normal controls (all values of $P>0.05$). The high and low doses of Cmyr-47 did not reduce the serum GLU levels below the normal glycemia displayed in the normal controls and the model controls (all values of $P>0.05$).

TABLE 19

Effect of Cmyr-47 on Serum GLU in Golden Hamster (mmol/L, $\bar{\chi}$ ± SEM)

| Group | Dosage/injection | n | Before dosing | GLU level after weeks of dosing | |
|---|---|---|---|---|---|
| | | | | 2 w | 4 w |
| Normal control | 10 mL/kg PBS | 10 | 4.09 ± 0.3 | 4.63 ± 0.8 | 4.99 ± 1.4 |
| Model control | 10 mL/kg PBS | 8 | 3.99 ± 0.4 | 4.52 ± 0.9 | 4.34 ± 0.7 |
| Low-dose | 10 mg/kg Cmyr-47 | 8 | 4.18 ± 0.3 | 3.87 ± 0.7 | 4.55 ± 1.0 |
| High-dose | 30 mg/kg Cmyr-47 | 8 | 4.11 ± 0.5 | 4.10 ± 0.7 | 4.38 ± 0.4 |

Note:
compared with normal control group,
$p < 0.05$,
$p < 0.01$;
compared with model control group,
*$p < 0.05$,
**$p < 0.01$ As discussed above, Cmyr-47 was capable of reversing hyperlipidemic phenotype in golden hamsters fed with a high-fat diet. In particular, the high dose of Cmyr-47 was capable of lowering all biological indicators measured in this study. In contrast, CsA, a bile acid uptake inhibitor, failed to produce a similar effect. Furthermore, despite the effective inhibition of bile acid uptake demonstrated by CsA in vitro, CsA treatment in vivo caused an increase of the serum TG and TC levels, confirming the hyperlipidemic effect of CsA.

Consistent with the effects on serum TC and TG levels of Cmyr-47, the AI values of Cmyr-47 treated animals were significantly lower than that of the non-treated hyperlipidemic animals, further demonstrating the efficacy of Cmyr-47 as a preventive medicine in cardiovascular diseases. In addition, other polypeptides derived from HBV showed similar efficacy in lowering serum TG, TC, and LDL-C, indicating that those polypeptides are also capable of reversing hyperlipidemic phenotype in vivo.

Example 3.8. Effects of Various Doses of Cmyr-47 on Serum TC and TG

The hyperlipidemic golden hamster model was established as described in Example 3.1. After 2 weeks of the high-fat diet treatment, the hyperlipidemic phenotype of hamsters was confirmed when the animals had serum total cholesterol (TC) levels higher than 10 mmol/L. A total of 32 hyperlipidemic hamsters were randomly stratified into 4 groups (N=8/group): a model control group (10 mL/kg PBS, subcutaneously (sc)), a low-dose treatment group (Cmyr-47, 1 mg/kg/day, sc), a middle-dose treatment group (Cmyr-47, 3 mg/kg/day, sc) and a high-dose treatment group (10 mg/kg/day Cmyr-47, sc). Eight hamsters fed with the normal chow diet were used as a normal control group (10 mL/kg PBS, sc).

By following the protocol described in Example 3.1, Cmyr-47 was administered for 4 consecutive weeks. During the experiment, all animals in the model control group, low, middle and high dose groups were fed with the high fat diet, while the normal control group was fed with the normal chow diet. Cmyr-47 or PBS was subcutaneously injected to the hamsters twice a day (9:00-10:00 in the morning and 16:00-17:00 in the afternoon). Each morning, food and water consumption, feces, and animal grooming were monitored. The serum TC and TG levels of all animals were measured on week 2 and week 4 of treatment as described in Example 3.1 and the results are summarized in Tables 20 and 21. The data was analyzed as described in Example 3.1.

Figure 15:
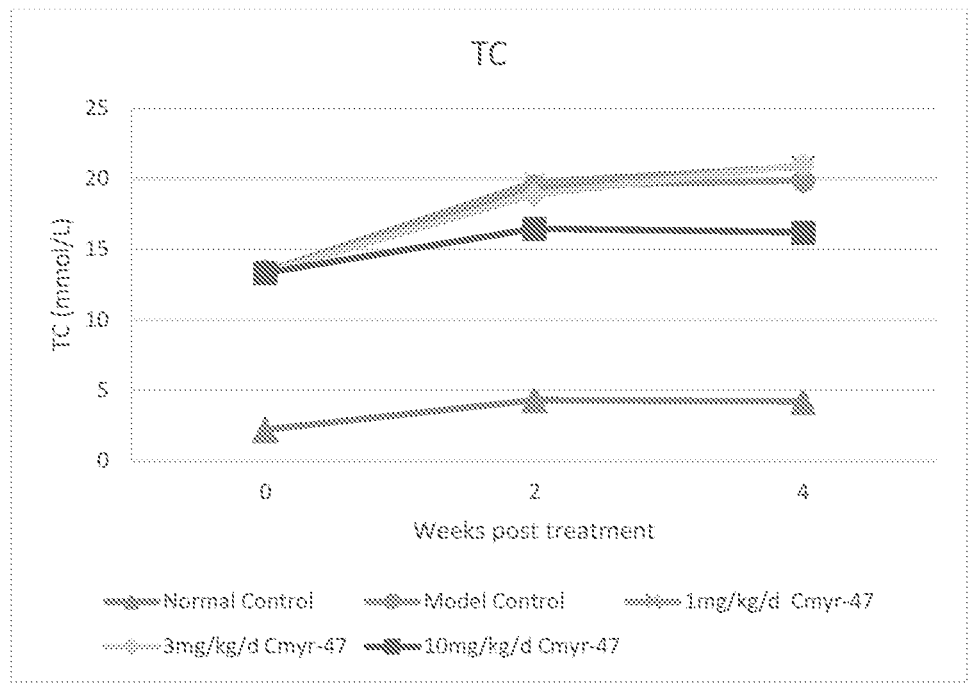
FIG. 15 shows the changes of serum TC of hyperlipidemic golden hamsters treated with three different doses (1 mg/kg, 3 mg/kg, and 10 mg/kg) of Cmyr-47 for 4 weeks. Golden hamsters fed with regular diet were treated with PBS and used as a "Normal Control," while hyperlipidemic golden hamsters treated with PBS were used as a "Model Control."

As shown in Table 20 and FIG. 15, the serum TC levels in the model controls were significantly higher than those in the normal controls during the experiment (all values of P<0.01). The treatment with Cmyr-47 at a dose of 1 mg/kg or 3 mg/kg had no effect on serum TC. However, hyperlipidemic animals treated with 10 mg/kg Cmyr-47 for 4 weeks showed moderately reduced levels of serum TC as compared with the model control group (P<0.05).

TABLE 20

Effect of Cmyr-47 on Serum TC (mmol/L, $\bar{\chi} \pm S$)

| | | | | TC level after weeks of dosing | |
|---|---|---|---|---|---|
| Group | Dosage/injection | n | Before dosing | 2 w | 4 w |
| Normal control | 10 mL/kg PBS | 8 | 2.21 ± 0.3 | 4.3 ± 0.3 | 4.25 ± 0.3 |
| Model control | 10 mL/kg PBS | 8 | 13.45 ± 1.6## | 19.47 ± 4.9## | 19.88 ± 3.9## |
| Low-dose | 1 mg/kg Cmyr-47 | 8 | 13.42 ± 1.5 | 19.75 ± 2.5 | 20.88 ± 4.0 |
| Middle-dose | 3 mg/kg Cmyr-47 | 8 | 13.33 ± 1.4 | 18.88 ± 2.1 | 20.99 ± 6.9 |
| High-dose | 10 mg/kg Cmyr-47 | 8 | 13.34 ± 1.4 | 16.47 ± 5.1 | 16.21 ± 4.2* |

Note:
compared with normal control group,
P < 0.05,
P < 0.01;
compared with model control group,
*P < 0.05,
**P < 0.01

Figure 16:
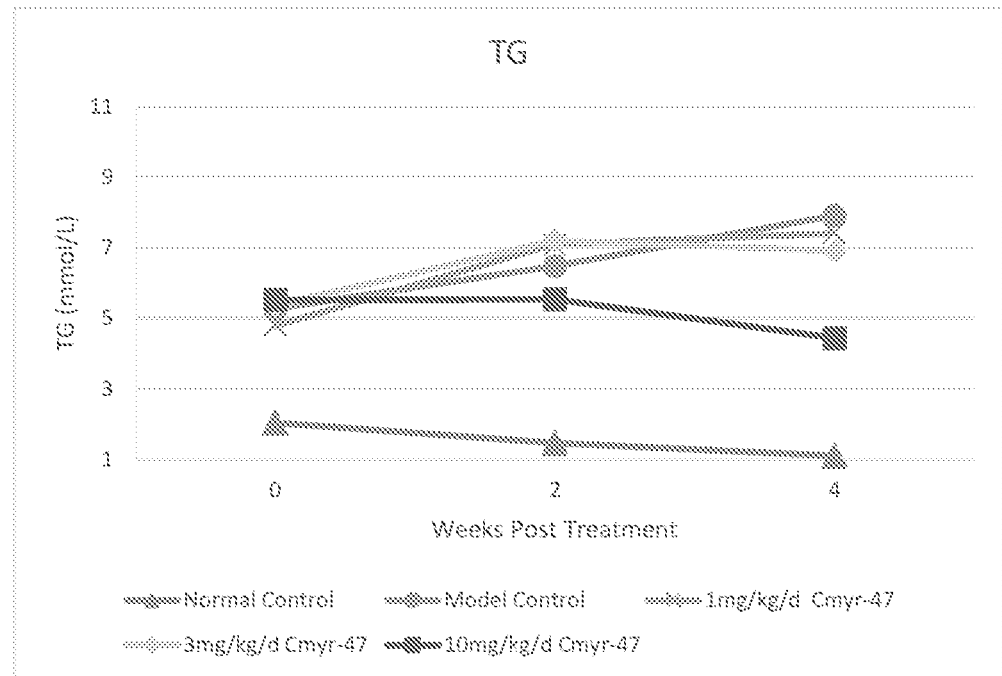
FIG. 16 shows the changes of serum TG of hyperlipidemic golden hamsters treated with 1 mg/kg, 3 mg/kg, or 10 mg/kg of Cmyr-47 for 4 weeks.

As shown in Table 21 and FIG. 16, the serum TG levels in the model controls were significantly higher than the normal controls throughout the experiment (all values of P<0.01). The treatment with Cmyr-47 at dose of 1 mg/kg or 3 mg/kg had no effect on serum TG. Hyperlipidemic animals treated with 10 mg/kg Cmyr-47 for 4 weeks expressed moderately lowered serum TG levels comparing to the model control group (P<0.05). These data suggest that administering a therapeutically effective amount of Cmyr-47 to reach serum concentrations of Cmyr-47 capable of bidirectionally regulating NTCP-mediated bile acid uptake may be beneficial for lowering serum TC and TG levels in hyperlipidemic patients.

TABLE 21

Effect of Cmyr-47 on Serum TG (mmol/L, $\bar{\chi} \pm S$)

| | | | | TG level after weeks of dosing | |
|---|---|---|---|---|---|
| Group | Dosage/injection | n | Before dosing | 2 w | 4 w |
| Normal control | 10 mL/kg PBS | 8 | 2.04 ± 0.8 | 1.46 ± 0.3 | 1.11 ± 0.2 |
| Model control | 10 mL/kg PBS | 8 | 5.28 ± 1.0## | 6.48 ± 1.6## | 7.92 ± 5.2## |
| Low-dose | 1 mg/kg Cmyr-47 | 8 | 4.78 ± 0.8 | 7.11 ± 2.1 | 7.41 ± 2.1 |
| Middle-dose | 3 mg/kg Cmyr-47 | 8 | 5.37 ± 1.3 | 7.21 ± 2.7 | 6.91 ± 1.9 |
| High-dose | 10 mg/kg Cmyr-47 | 8 | 5.52 ± 1.3 | 5.55 ± 2.4 | 4.44 ± 2.1* |

Note:
compared with normal control group,
P < 0.05,
P < 0.01;
compared with model control group,
*P < 0.05,
**P < 0.01

Example 4

Example 4.1. Methods and Materials Used in Treatment of Zucker Diabetic Fatty Rats with Cmyr-47

The efficacy of Cmyr-47 as an anti-diabetic, anti-hyperlipidemic, and/or anti-hypercholesterolemic agent was tested in Zucker Diabetic Fatty (ZDF) rats, a spontaneous type II diabetes animal model. Male 60-days old ZDF rats (n=40) and Zucker Lean (ZL) rats (n=6) were purchased from Vital River Laboratory Animal Technology Co., Ltd. (SCXK (Beijing) 2012-0001) with animal quality certification numbers 11400700109970 and 11400700109972. All animals were housed at 23 PC with 50-70% humidity under specific-pathogen-free (SPF) environment and under a 12 hour light:dark cycle (150-200 Lx), in a noise-controlled room (<50 dB) at the Zhejiang Traditional Chinese Medicine University Animal Experimental Research Center [SYXK (Zhe)2013-0184]. Animals had a free access to filtered and sterilized water in autoclaved water bottle. ZDF rats were fed with Purina #5008 diet purchased from Specialty Feeds, Inc. (Memphis, Tenn.; Purina 5008; Catalogue No. SF06-019). ZL rats were fed with a normal chow diet (basic feed) sterilized by $Co^{60}$ gamma irradiation. Two ZDF rats or ZL rats were housed in each cage and cage bedding was changed once every 2 days. The experimental rat breeding and all other operations were in accordance with the principle of 3R with humane care.

After 2 weeks of Purina #5008 diet or the normal chow diet, all animals were fasted for 10 h with access to water. Each animal was then weighed and tail-bled to collect 0.3 mL of blood. The blood samples were further analyzed for glycated hemoglobin (HbA1c). Additional 0.5 mL of blood was collected and centrifuged at 3,000 rpm for 10 min in order to separate serum. The HbA1c, serum glucose (GLU), and insulin levels in the animals were measured by kits provided below. Hitachi 7020 automatic biochemical analyzer was used for all the measurements.

30 animals with the fasting serum GLU levels close to the average level were selected and randomly divided into 5 groups: a model control group (10 ml·kg$^{-1}$ PBS), a low-dose treatment group (10 mg·kg$^{-1}$ Cmyr-47), a high-dose treatment group (30 mg·kg$^{-1}$ Cmyr-47), a positive control group (300 mg·kg$^{-1}$ Metformin), and a CsA treatment group (20 mg·kg$^{-1}$ CSA) with 6 animals per group. Six ZL rats were used as a normal control group (10 ml·kg$^{-1}$ PBS). PBS or Cmyr-47 was injected to animals subcutaneously twice per day (at 09:00 and 17:00). Meformin (MET) and CsA solutions were given via oral gavage twice per day in the morning and afternoon. The dosing was conducted for 4 weeks. During the experiment, ZDF rats were fed with Purina #5008 diet while ZL rats were fed the normal chow diet.

Cmyr-47 was synthesized as described above, purified as a white powder by Shanghai HEP Pharmaceutical Co., Ltd (Shanghai, China; Lot number 14011801), and stored at −20° C. Cmyr-47 was weighed and dissolved in PBS right before use. MET was manufactured by Bristol-Myers Squibb Co., Ltd. (Shanghai, China) with approval number H20023370 and lot number of AAD7878. CsA (Sandimmune®) was purchased from Novartis.

At the second-week of dosing, the animals were fasted for 10 h with free access to water, and 0.3 mL of blood from each animal was collected via tail vein bleeding for measuring serum GLU, total cholesterol (TC), triglycerides (TG) and blood urea nitrogen (BUN). At the fourth-week of dosing, the animals were fasted for 10 h and the blood was then collected for the measurement of serum GLU, TC, TG and BUN, HbA1c and insulin. After the last dose of drugs, the animals were fasted for 12 h and then anesthetized via intraperitoneal injection of 3% sodium pentobarbital and cervical dislocation. Heart, kidneys, scapular fat, and abdominal fat of each animal were dissected for visual observation and weighed to calculate heart, kidney, and total fat index.

Pentobarbital sodium (content ≥95.0%; Lot number 20130112) was purchased from Merck. TC, TG, GLU and BUN kits were purchased from DiaSys Diagnostic Systems (Shanghai, China). HbA1c detection reagent was purchased from Trinity Biotech Inc., Ireland. Insulin ELISA detection kit (Lot number: 0469636-1) was purchased from Bertin Pharma (France). All measurements using the purchased kits were conducted following the manufacturers' protocols provided in the kits.

SQP electronic balance was purchased from Sartorius Scientific Instruments (Beijing) Co., Ltd. (Beijing, china). MLS-3750 autoclave was purchased from Sanyo, Japan. RO-MB-50 ultrapure water system was manufactured by Hangzhou Yongjieda Cleaning Science and Technology, Co., Ltd. (Zhejiang, China). KQ-300DE ultrasound was purchased from Kunshan Ultrasonic Instruments Co., Ltd. (Jiangsu, China). Hitachi 7020 automatic biochemical analyzer was purchased from Hitachi, Japan. Hb9210 glycated hemoglobin analyzer, Trinity Biotech Inc, Ireland. Multifunctional microplate reader was purchased from Thermo Fisher Scientific, Co. (MA, USA).

SPSS 19.0 software (SPSS, Chicago, Ill.) was used for statistical analysis. All data were presented as mean standard error mean ($\bar{\chi}$±SEM). ANOVA variance analysis was used to evaluate the data from the test results. LSD test was used for pairwise comparisons. Values of the statistical analyses were rounded to 2 decimal places.

Example 4.2. Effect of Cmyr-47 and Additional Polypeptides Derived from HBV on Serum Glucose (GLU)

Figure 17:
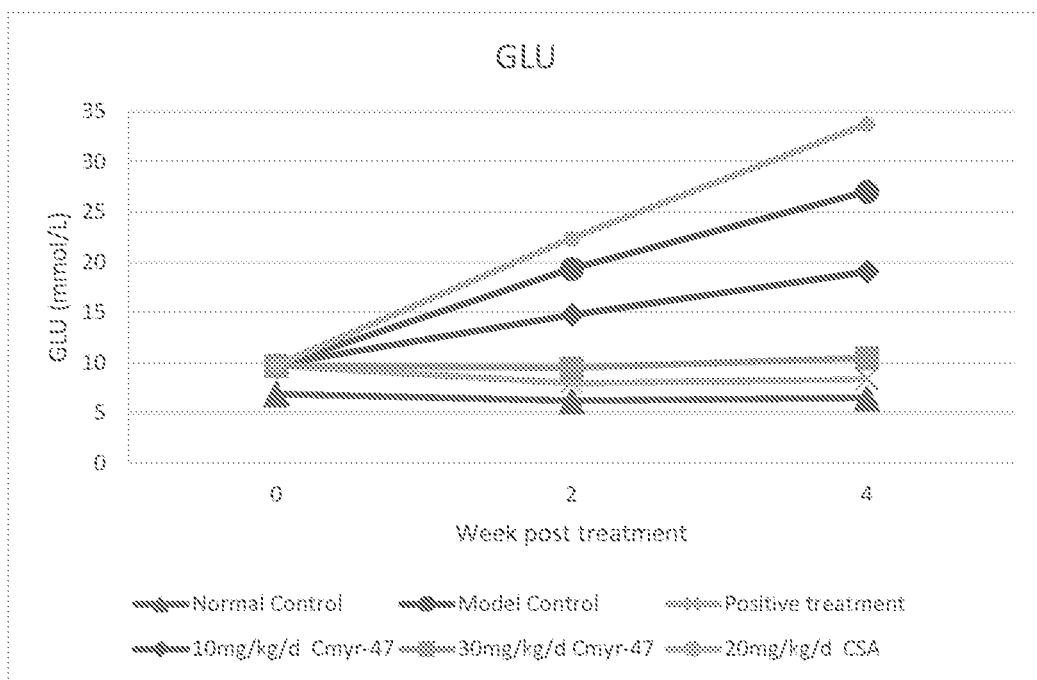
FIG. 17 shows the changes of serum glucose ("GLU") in Zucker diabetic fatty rats during 4 weeks of Cmyr-47 or CsA treatment. Zucker lean rats treated with PBS were used as a "Normal Control" while Zucker diabetic fatty rats treated with PBS were used as a "Model Control." Zucker diabetic fatty rats treated with metformin ("Positive Treatment") were used as a positive control.

Hyperglycemia (i.e., increased blood glucose) is one of the most prominent symptoms of type II diabetes. As shown in Table 22 and FIG. 17, hyperglycemic phenotype of ZDF rats was confirmed by comparing the serum GLU levels of the model controls with the normal controls (all values of $P<0.01$). MET is a well-known anti-diabetic agent that effectively lowers glycemia in diabetic patients. As expected, ZDF rats treated with MET showed significantly decreased fasting serum GLU as compared with the model controls. Cmyr-47 was also capable of lowering glycemia in ZDF rats. In particular, by 4 weeks of treatments, both low and high doses of Cmyr-47 effectively reduced the serum GLU levels in the animals. The effect of Cmyr-47 on glycemia was dose-dependent. In contrast, CsA treatment significantly elevated the serum GLU levels in the animals as compared with the model control.

TABLE 22

Effect of Cmyr-47 on Fasting Serum GLU in ZDF Rats (mmol/L, $\bar{\chi}$ ± SEM)

| Group | Dosage/injection | GLU level after weeks of dosing | | |
|---|---|---|---|---|
| | | 0 | 2 | 4 |
| Normal control | 10 mL/kg PBS | 6.91 ± 0.22 | 6.23 ± 0.27 | 6.51 ± 0.19 |
| Model control | 10 mL/kg PBS | 9.68 ± 0.90# | 19.36 ± 3.35## | 27.03 ± 1.07## |
| Positive control | 300 mg/kg Met | 9.71 ± 0.96 | 7.98 ± 1.02** | 8.35 ± 0.58** |
| Cmyr-47Lo | 10 mg/kg Cmyr-47 | 9.82 ± 1.19 | 14.74 ± 0.68 | 19.16 ± 1.23** |
| Cmyr-47Hi | 30 mg/kg Cmyr-47 | 9.73 ± 1.01 | 9.50 ± 1.72* | 10.50 ± 2.34** |
| CsA treatment | 20 mg/kg CsA | 9.76 ± 1.22 | 22.38 ± 3.08 | 33.75 ± 6.68* |

Note:

compare to normal control group,

$P < 0.05$,

$P < 0.01$;

compare to model control group,

*$P < 0.05$,

**$P < 0.01$

Additional polypeptides derived from HBV listed in Table 1 were also tested in order to analyze their effects on glycemia in vivo by following the same protocol described above. All polypeptide was administrated at a dose molarly equivalent to 30 mg/kg/day of Cmyr-47.

Figure 18:
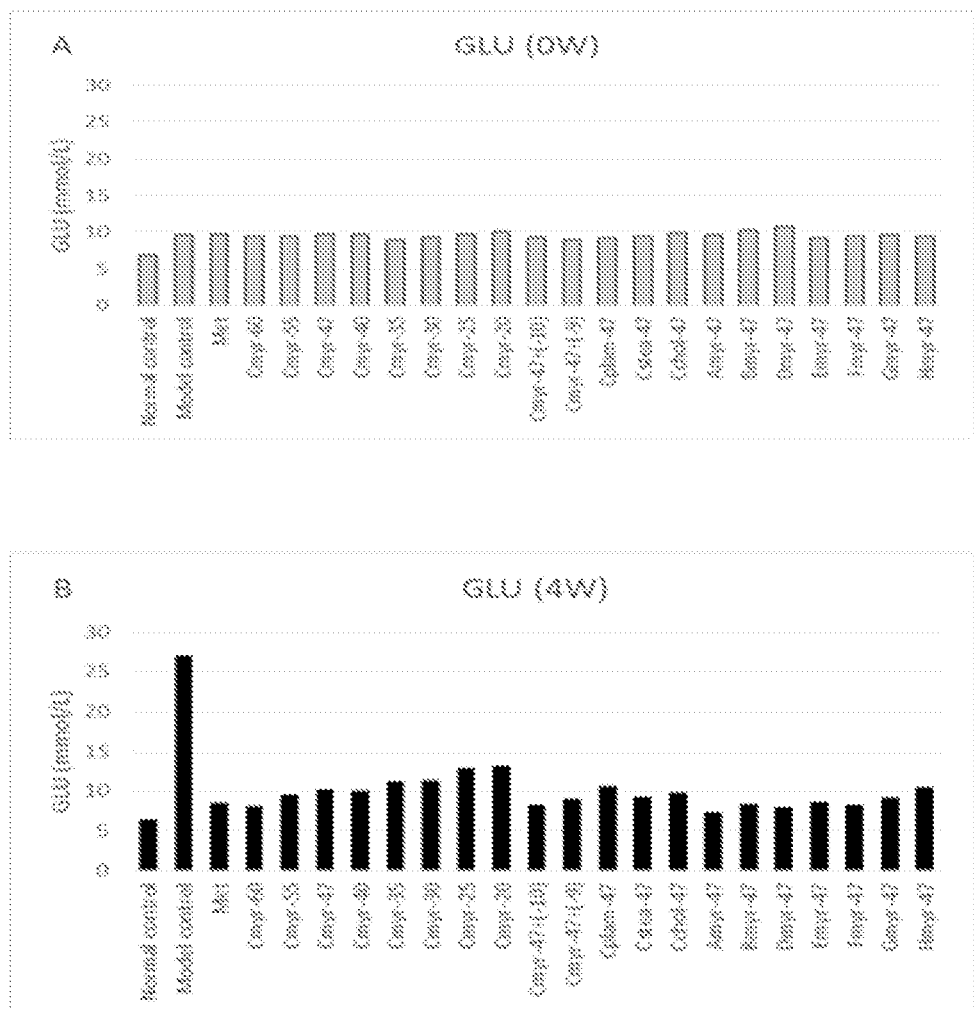
FIG. 18A shows the level of serum GLU before being treated with polypeptides derived from HBV.
FIG. 18B shows the level of serum GLU after 4 weeks of the treatments.

As shown in FIGS. 18A and 18B, hyperglycemic phenotype of ZDF rats was confirmed. As observed in the study above, the treatment with MET significantly decreased fasting serum GLU in vivo. After 4 weeks of treatment with HBV-derived peptides (Cmyr-60, Cmyr-55, Cmyr-40, Cmyr-35, Cmyr-30, Cmyr-25, Cmyr-20, Cmyr-47+(-10), Cmyr-47+(-9), Cplam-47, Cstea-47, Cchol-47, Amyr-47, Bmyr-47, Dmyr-47, Emyr-47, Fmyr-47, Gmyr-47 or Hmyr-47), the fasting serum GLU levels of ZDF rats decreased as compared with the model controls, indicating the efficacy of the polypeptides as an anti-diabetic agent.

Figure 19:
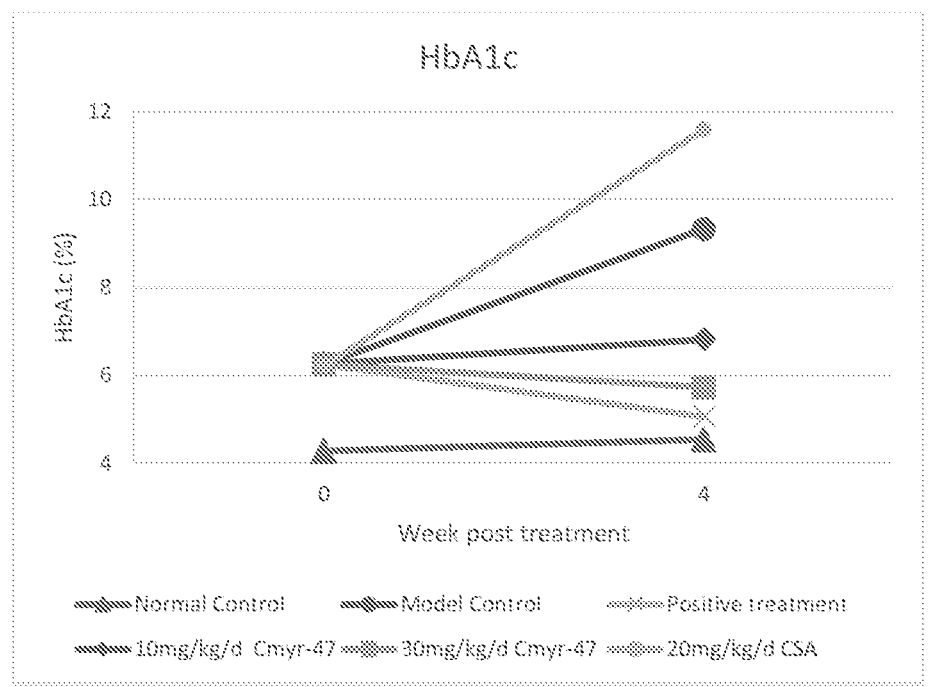
FIG. 19 shows the changes of HbA1c of Zucker diabetic fatty rats during 4 weeks of Cmyr-47 treatment.

Example 4.3. Effect of Cmyr-47 and Additional Polypeptides Derived from HBV on HbA1c HbA1c refers to glycated hemoglobin, and its level significantly increases when a subject is experiencing chronic hyperglycemia. As shown in Table 23 and FIG. 19, consistent with hyperglycemic phenotype of ZDF rats, the HbA1c levels in the model controls were significantly higher than the normal control throughout the study (all values of $P<0.01$). Also, consistent with the effect of MET on glycemia, the treatment with MET significantly decreased the HbA1c levels in ZDF rats ($P<0.01$). ZDF rats treated with Cmyr-47 also showed significantly reduced HbA1c levels as compared with the model controls in a dose-dependent fashion, confirming the efficacy of Cmyr-47 as an anti-diabetic agent that regulates glycemia in vivo. Consistent with the effect of CsA on the serum GLU levels, CsA treatment significantly increased the serum HbA1c after 4 weeks of treatment.

TABLE 23

Effect of Cmyr-47 on HbA1c Level in ZDF Rats (%, $\bar{\chi} \pm$ SEM)

| Group | Dosage/injection | HbA1c level after weeks of dosing | |
|---|---|---|---|
| | | 0 | 4 |
| Normal control | 10 mL/kg PBS | 4.28 ± 0.02 | 4.55 ± 0.02 |
| Model control | 10 mL/kg PBS | 6.27 ± 0.25## | 9.33 ± 0.40## |
| Positive control | 300 mg/kg Met | 6.25 ± 0.31 | 5.07 ± 0.23** |
| Cmvr-47Lo | 10 mg/kg Cmyr-47 | 6.27 ± 0.24 | 6.82 ± 0.44** |
| Cmyr-47Hi | 30 mg/kg Cmyr-47 | 6.25 ± 0.31 | 5.73 ± 0.39** |
| CsA treatment | 20 mg/kg CsA | 6.23 ± 0.44 | 11.60 ± 1.03** |

Figure 20:
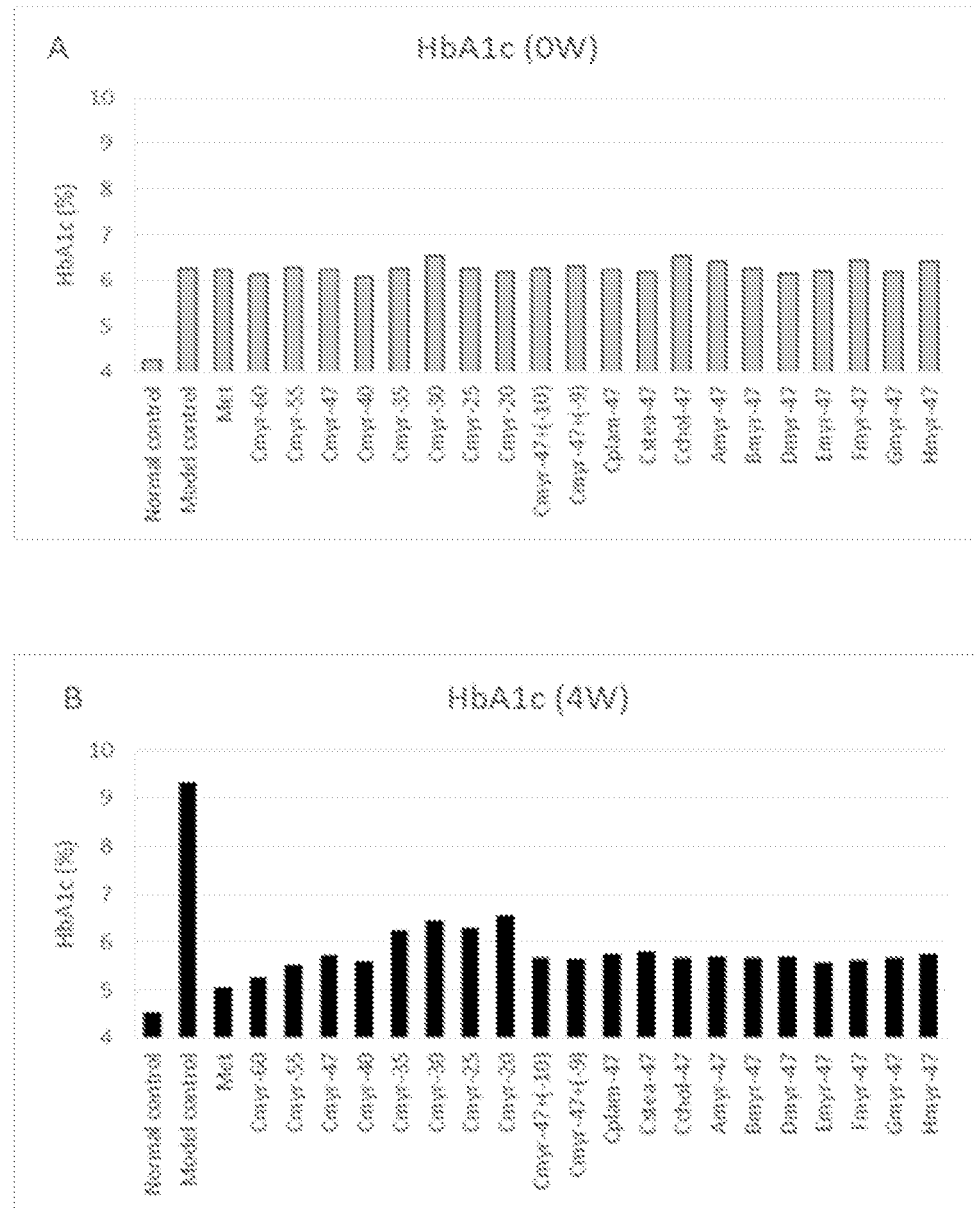
FIG. 20A shows the level of HbA1c prior to treatments with polypeptides derived from HBV.
FIG. 20B shows the level of HbA1c after 4 weeks of the treatments.

Note:
compare to normal control,
$P < 0.05$,
$P < 0.01$;
compare to model control,
*$P < 0.05$,
$P < 0.01$ Additional polypeptides derived from HBV listed in Table 1 also showed a similar effect on HbA1c when tested in the same animal model as described above. As shown in FIGS. 20A and 20**B, the HbA1c levels of the model controls were higher than that of the ZDF rats treated with the polypeptides. These results demonstrate that the polypeptides derived from HBV are capable of effectively lowering glycemia and HbA1c, and confirm the hyperglycemic effect of CsA.

Example 4.4. Effect of Cmyr-47 on Serum Insulin

Figure 21:
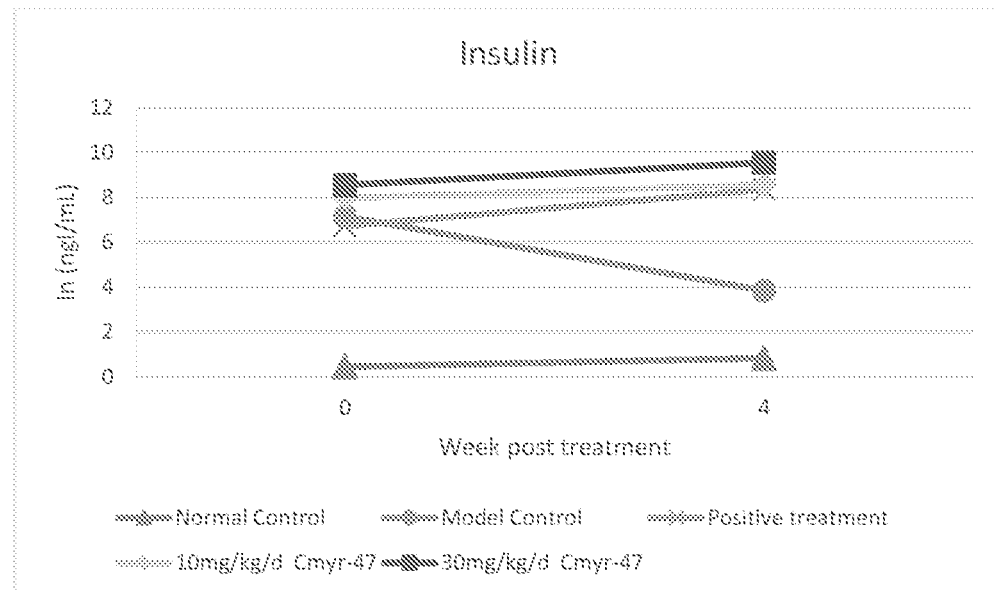
FIG. 21 shows the changes of insulin in Zucker diabetic fatty rats during 4 weeks of Cmyr-47 treatment.

Type II diabetic patients experience insulin resistance, overproduction of insulin, and ultimately insulin deprivation due to pancreatic damage. To confirm that Cmyr-47 is capable of modulating insulin by preventing pancreatic damage, the insulin levels of animals treated with Cmyr-47 were compared with animals treated with PBS or MET. As shown in Table 24 and FIG. 21, the initial serum insulin levels of ZDF rats were significantly higher than the normal controls. While the insulin levels of ZDF rats remained higher than the normal controls at week 4, the absolute levels significantly dropped as compared with the initial levels. This change indicates that insulin resistance in ZDF rats progressed during the study, resulting in pancreatic failure. The treatment with MET appeared to be protective against the loss of serum insulin, although the difference between the fasting insulin levels of the model controls and positive controls was not statistically significant ($P>0.05$). Cmyr-47 treatment, however, completely stabilized insulin secretion, if not increased, at both doses, indicated by the significant difference between the model controls and the Cmyr-47 treated animals (all values of $P<0.05$). These results demonstrate that Cmyr-47 may prevent pancreatic damage and therefore help a diabetic patient to maintain proper insulin secretion.

TABLE 24

Effect of Cmyr-47 on Serum Insulin in ZDF Rats (ng/mL, $\bar{\chi} \pm$ SEM)

| Group | Dosage/injection | Insulin level after weeks of dosing | |
|---|---|---|---|
| | | 0 | 4 |
| Normal control | 10 mL/kg PBS | 0.46 ± 0.06 | 0.84 ± 0.06 |
| Model control | 10 mL/kg PBS | 7.15 ± 1.38## | 3.85 ± 1.25## |
| Positive control | 300 mg/kg Met | 6.74 ± 0.62 | 8,36 ± 3.68 |
| Cmyr-47Lo | 10 mg/kg Cmyr-47 | 7.99 ± 1.17 | 8.57 ± 2.18* |
| Cmyr-47Hi | 30 mg/kg Cmyr-47 | 8.55 ± 1.07 | 9.56 ± 4.26* |

Note:
compared with normal control group,
$P < 0.05$,
$P < 0.01$;
compared with model control group,
*$P < 0.05$,
**$P < 0.01$ Example 4.5. Effect of Cmyr-47 and Additional Polypeptides Derived from HBV on Serum Total Cholesterol (TC)

Figure 22:
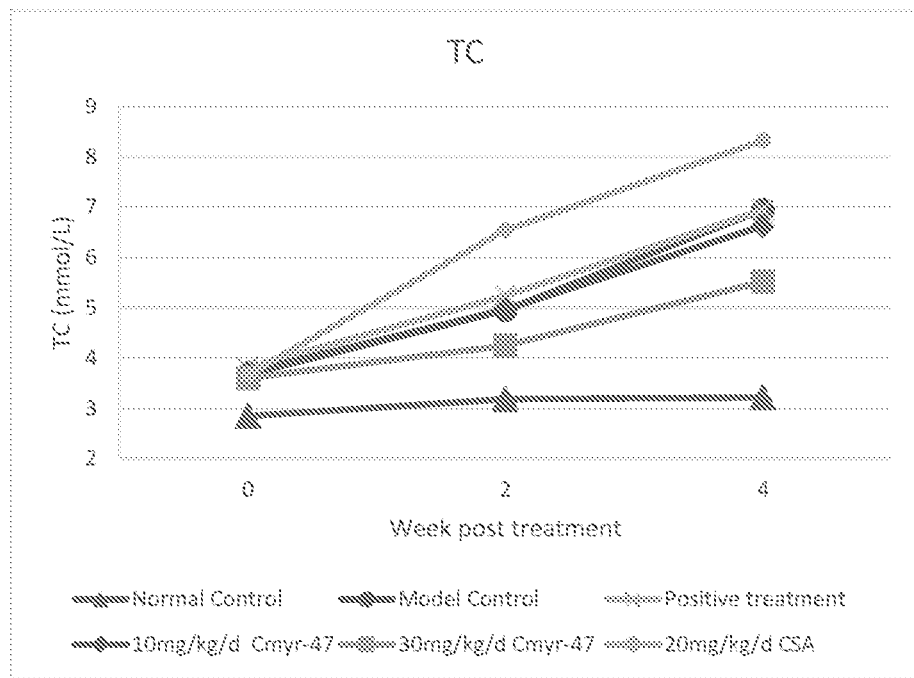
FIG. 22 shows the changes of serum TC in Zucker diabetic fatty rats during 4 weeks of Cmyr-47 treatment.

As discussed above, diabetic phenotypes include lipid dysregulation including elevated cholesterol and triglycerides in the blood stream. As shown in Table 25 and FIG. 22, the serum TC levels in the model controls were consistently elevated as compared with the normal controls (all values of $P<0.05$). In contrast to the effect of MET on glycemia, however, MET appeared to be completely ineffective in lowering the serum TC levels in ZDF rats. CsA was also ineffective in lowering the serum TC levels in ZDF rats and by 4 weeks of treatment, CsA significantly increased the serum TC levels as compared with the model control. Notably, the high dose of Cmyr-47 significantly reduced the serum TC levels in ZDF rats as compared with the model controls, confirming that Cmyr-47 can regulate a wide array of biomarkers that are severely elevated in diabetic patients.

TABLE 25

Effect of Cmyr-47 on Serum TC in ZDF Rats (mmol/mL, $\bar{\chi} \pm$ SEM)

| Group | Dosage/injection | TC level after weeks of dosing | | |
|---|---|---|---|---|
| | | 0 | 2 | 4 |
| Normal control | 10 mL/kg PBS | 2.85 ± 0.03 | 3.18 ± 0.06 | 3.22 ± 0.04 |
| Model control | 10 mL/kg PBS | 3.68 ± 0.46# | 4.95 ± 0.15## | 6.95 ± 0.21## |
| Positive control | 300 mg/kg Met | 3.82 ± 0.11 | 5.24 ± 0.35 | 6.95 ± 0.54 |
| Cmyr-47Lo | 10 mg/kg Cmyr-47 | 3.72 ± 0.15 | 4.97 ± 0.19 | 6.63 ± 0.18 |
| Cmyr-47Hi | 30 mg/kg Cmyr-47 | 3.60 ± 0.18 | 4.25 ± 0.27* | 5.52 ± 0.41** |
| CsA treatment | 20 mg/kg CsA | 3.65 ± 0.48 | 6.54 ± 0.63** | 8.33 ± 0.65** |

Note:
compared with normal control group,
P < 0.05,
P < 0.01;
compared with model control group,
*P < 0.05,
**P < 0.01

Figure 23:
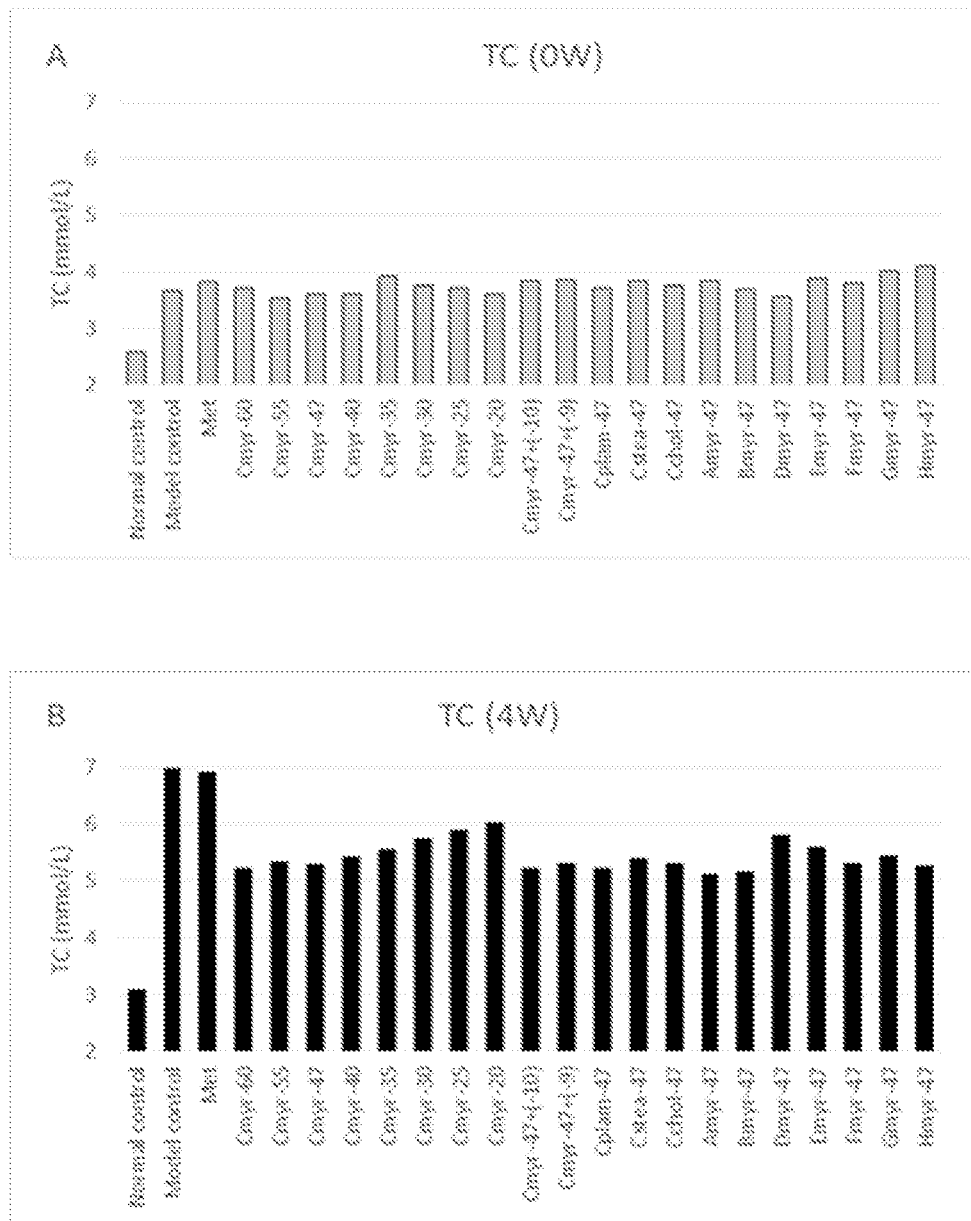
FIG. 23A shows the level of serum TC prior to treatments with polypeptides derived from HBV.
FIG. 23B shows the level of serum TC after 4 weeks of the treatments.

Animals treated with additional polypeptides derived from HBV also showed that those polypeptides are capable of reducing serum TC in vivo. As shown in FIGS. 23A and 23B, after 4 weeks of treatment with HBV-derived peptides (Cmyr-60, Cmyr-55, Cmyr-40, Cmyr-35, Cmyr-30, Cmyr-25, Cmyr-20, Cmyr-47+(-10), Cmyr-47+(-9), Cplam-47, Cstea-47, Cchol-47, Amyr-47, Bmyr-47, Dmyr-47, Emyr-47, Fmyr-47, Gmyr-47 or Hmyr-47), the serum TC levels of ZDF rats were lower than that of the model controls. These results demonstrate that while MET may target only one particular symptom, a polypeptide derived from HBV is capable of targeting multiple pathways and therefore beneficial to manage diabetes-related symptoms simultaneously.

Example 4.6. Effect of Cmyr-47 and Additional Polypeptides Derived from HBV on Serum Triglycerides (TG)

Figure 24:
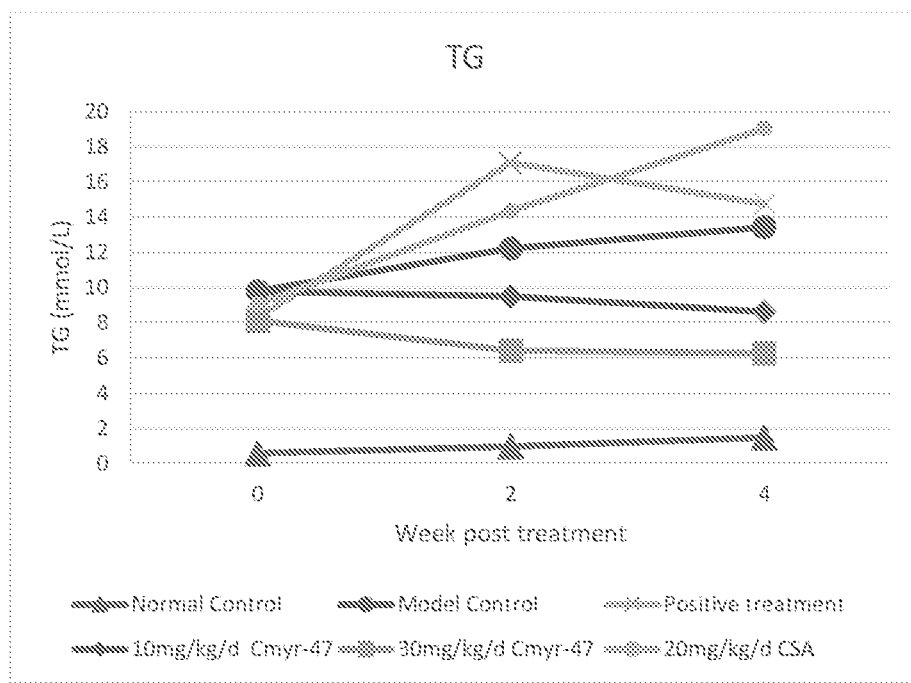
FIG. 24 shows the changes of serum TG in Zucker diabetic fatty rats during 4 weeks of Cmyr-47 treatment.

In addition to serum TC, serum TG is also a biomarker for hyperlipidemia that may be caused by diabetes. As expected, Table 26 and FIG. 24 show that the serum TG levels in the model controls were significantly higher than that of the normal controls throughout the study (all values of P<0.01). Of note, MET significantly elevated the serum TG levels in ZDF rats at week 2 (P<0.01). While the difference was not significant, the serum TC levels in ZDF rats treated with MET remained higher than the model controls at week 4. Consistent with the effect on serum TC levels, CsA further increased the serum TG levels in ZDF rats. In contrast, both doses of Cmyr-47 were capable of lowering the serum TG levels of ZDF rats and the effect of Cmyr-47 was dose-dependent.

TABLE 26

Effect of Cmyr-47 on Serum TG in ZDF Rats (mmol/mL, $\bar{\chi} \pm$ SEM)

| Group | Dosage/injection | TG level after weeks of dosing | | |
|---|---|---|---|---|
| | | 0 | 2 | 4 |
| Normal control | 10 mL/kg PBS | 0.58 ± 0.03 | 0.96 ± 0.08 | 1.47 ± 0.15 |
| Model control | 10 mL/kg PBS | 9.80 ± 2.95## | 12.23 ± 1.36## | 13.43 ± 2.21## |
| Positive control | 300 mg/kg Met | 8.32 ± 0.65 | 17.10 ± 2.02** | 14.74 ± 1.99 |
| Cmyr-47Lo | 10 mg/kg Cmyr-47 | 9.78 ± 0.48 | 9.50 ± 0.58 | 8.62 ± 0.41* |
| Cmyr-47Hi | 30 mg/kg Cmyr-47 | 8.11 ± 0.72 | 6.42 ± 0.92** | 6.26 ± 0.64** |
| CsA treatment | 20 mg/kg CsA | 9.04 ± 0.84 | 14.34 ± 1.88** | 19.03 ± 2.65** |

Note:
compared with normal control, #P <0.5, ##P <0.01;
compared with model control, *P <0.05, **P <0.01

Figure 25:
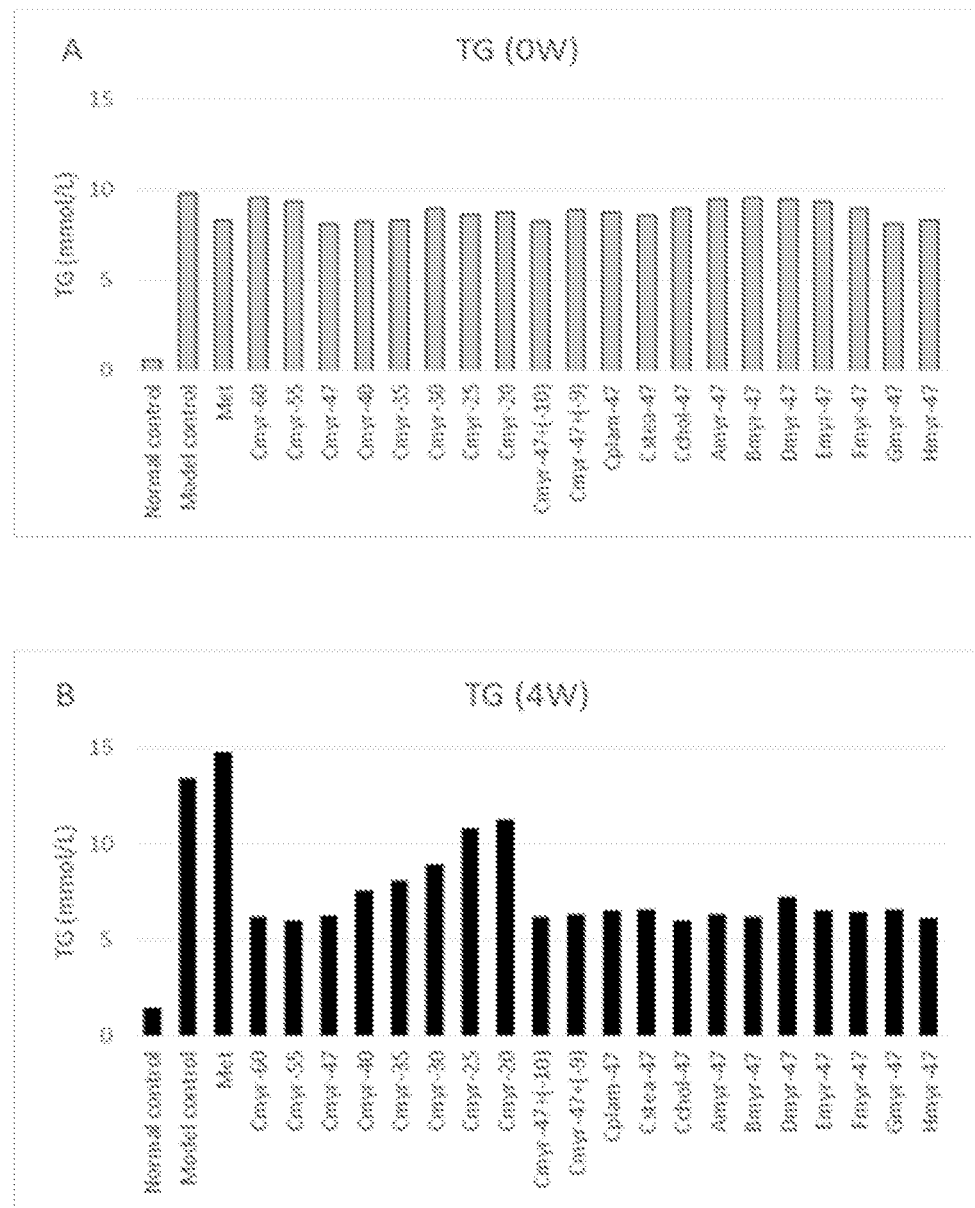
FIG. 25A shows the level of serum TG prior to treatments with polypeptides derived from HBV.
FIG. 25B shows the level of serum TG after 4 weeks of the treatments.

Additional polypeptides derived from HBV were also capable of reducing serum TG in vivo when tested in the same animal model described above. As shown in FIGS. 25A and 25B, the serum TG levels of the model controls remained higher than ZDF rats treated with HBV-derived peptides (Cmyr-60, Cmyr-55, Cmyr-40, Cmyr-35, Cmyr-30, Cmyr-25, Cmyr-20, Cmyr-47+(-10), Cmyr-47+(-9), Cplam-47, Cstea-47, Cchol-47, Amyr-47, Bmyr-47, Dmyr-47, Emyr-47, Fmyr-47, Gmyr-47 or Hmyr-47), further confirming that polypeptides derived from HBV are capable of regulating glucose metabolism and lipid metabolism simultaneously.

Example 4.7. Effect of Cmyr-47 on Serum Blood Urea Nitrogen (BUN)

Figure 26:
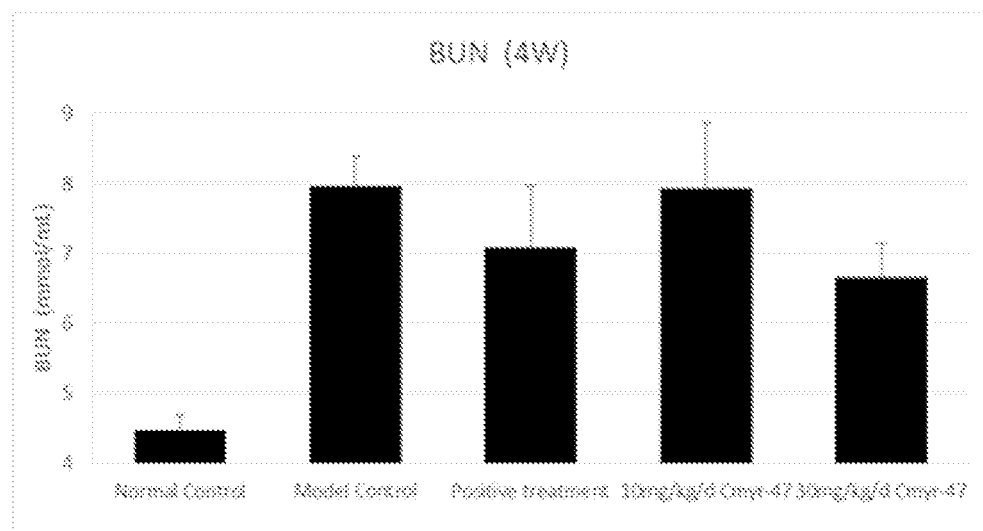
FIG. 26 shows the level of blood urea nitrogen ("BUN") in Zucker diabetic fatty rats after 4 weeks of Cmyr-47 treatment.

Elevated serum BUN reflects impaired renal function, which often occurs in human diabetic patients. In ZDF model, diabetic phenotypes lead to renal dysfunction and the correlative elevation of serum BUN. As expected, Table 27 and FIG. 26 show that the serum BUN levels in the model controls were significantly higher than that of the normal controls throughout the study. The treatment of MET was not capable of reversing renal dysfunction as no significant BUN difference was found between the model controls and the positive controls. However, the high dose of Cmyr-47 significantly lowered the serum BUN levels in ZDF rats at week 4 (P<0.01), indicating that Cmyr-47 may protect a diabetic subject against kidney damage and renal dysfunction.

TABLE 27

Effect of Cmyr-47 on Serum BUN in ZDF Rats (mmol/mL, $\bar{\chi}$ ± SEM)

| Group | Dosage/injection | BUN level after weeks of dosing | | |
|---|---|---|---|---|
| | | 0 | 2 | 4 |
| Normal control | 10 mL/kg PBS | 4.71 ± 0.22 | 5.54 ± 0.06 | 4.48 ± 0.09 |
| Model control | 10 mL/kg PBS | 6.13 ± 0.51# | 6.62 ± 0.35 | 7.96 ± 0.18## |
| Positive control | 300 mg/kg Met | 5.52 ± 0.21 | 6.58 ± 0.52 | 7.09 ± 0.36 |
| Cmyr-47Lo | 10 mg/kg Cmyr-47 | 5.26 ± 0.29 | 6.83 ± 0.48 | 7.93 ± 0.38 |
| Cmyr-47Hi | 30 mg/kg Cmyr-47 | 5.83 ± 0.37 | 6.44 ± 0.45 | 6.65 ± 0.20** |

Note:
compared with normal control group,
P < 0.05,
P < 0.01;
compared with model control group,
*P < 0.05,
**P < 0.01

Example 4.8. Effect of Cmyr-47 on Organ Index

Diabetic patients have an increased risk of developing cardiovascular diseases, renal dysfunction, and obesity. As discussed above, various indexes such as heart index (HI), kidney index (KI), and total fat index (TFI) can be used as a quantitative indicator of the risk. As shown in Table 28 and FIG. 27A, the HI values of the model controls were higher than the normal controls. The treatment with MET had no effect on the HI values. Surprisingly, both doses of Cmyr-47 significantly decreased the HI values of ZDF rats, indicating that Cmyr-47 can be beneficial to prevent adverse cardiovascular events.

Figure 27:
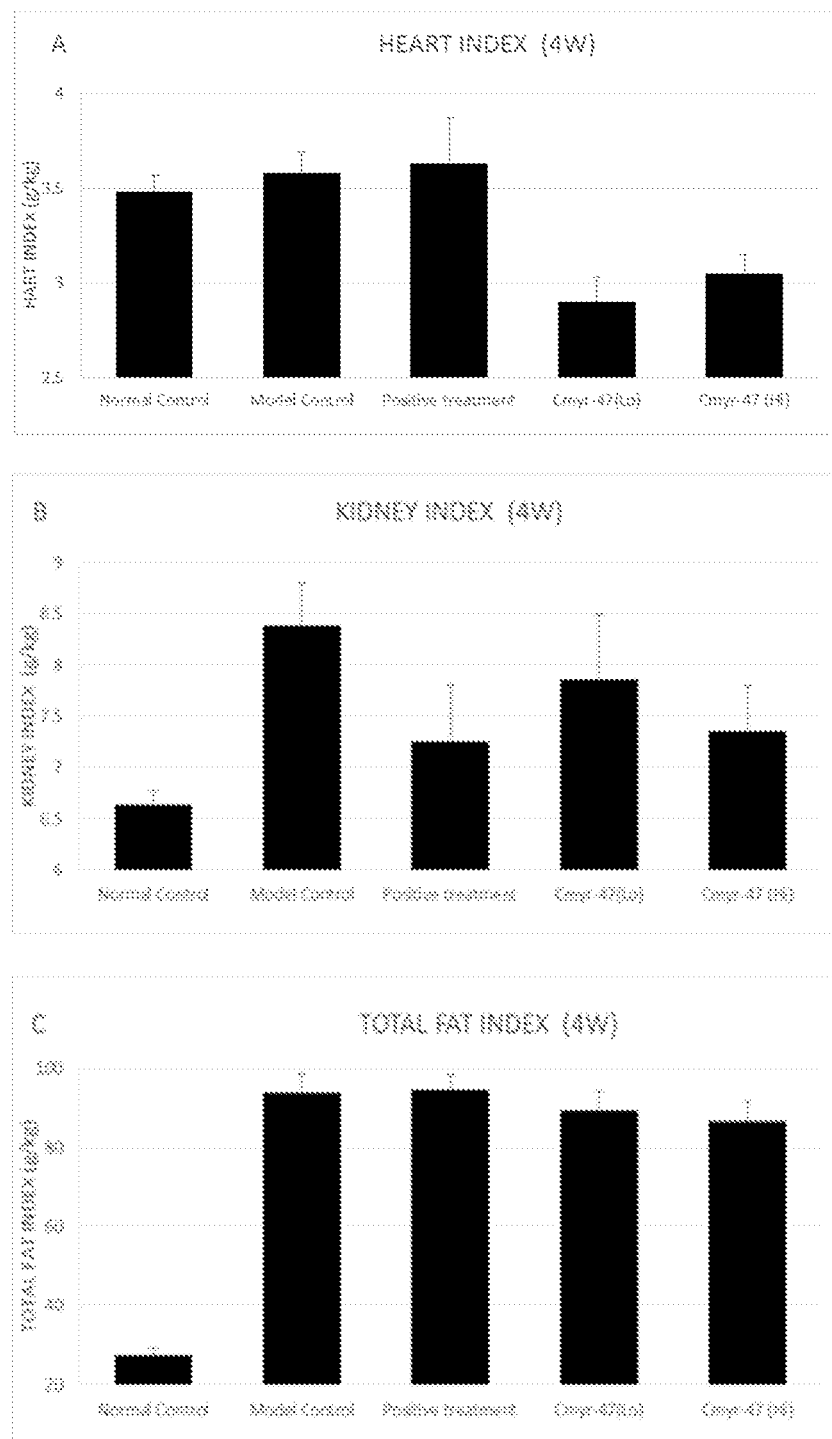
FIGS. 27A-C depict heart index, kidney index, and total fat index of Zucker diabetic fatty rats after 4 weeks of Cmyr-47 treatment. "Cmyr-47(L)" indicates the dose of 10 mg/kg/d of Cmyr-47 while "Cmyr-47(Hi)" indicates the dose of 30 mg/kg/d of Cmyr-47.

As shown in Table 28 and FIG. 27B, the KI values of the model controls were significantly higher than the normal controls (P<0.01), confirming that ZDF rats developed renal dysfunction during the study. Consistent with the effect of Cmyr-47 on serum BUN, Cmyr-47 treatment also lowered the KI values in ZDF rats, although the difference did not meet the statistical significance.

Table 28 and FIG. 27C show that the TFI values of the model controls were significantly higher than normal controls (P<0.01), indicating that ZDF rats reached morbid obesity. Although not significant, ZDF rats treated with Cmyr-47 showed a trend of TFI values lower than the model controls. Of note, MET did not show the similar trend and rather, it appeared to increase the TFI values in ZDF rats.

TABLE 28

Effect of Cmyr-47 on Organ Index in ZDF Rats After 4 Weeks of Treatment (g/kg, $\bar{\chi}$ ± SEM)

| Group | Dosage/injection | Heart index | Kidney index | Total fat index |
|---|---|---|---|---|
| Normal control | 10 mL/kg PBS | 3.48 ± 0.09 | 6.64 ± 0.13 | 27.47 ± 1.63 |
| Model control | 10 mL/kg PBS | 3.63 ± 0.19 | 8.39 ± 0.41# | 93.70 ± 5.01## |
| Positive control | 300 mg/kg Met | 3.63 ± 0.24 | 7.26 ± 0.55 | 94.64 ± 3.79 |
| Cmyr-47Lo | 10 mg/kg Cmyr-47 | 2.90 ± 0.13* | 7.86 ± 0.63 | 89.18 ± 4.95 |
| Cmyr-47Hi | 30 mg/kg Cmyr-47 | 3.05 ± 0.10* | 7.36 ± 0.44 | 86.61 ± 5.03 |

Note:
compared with normal control,
P < 0.05,
P < 0.01;
compared with model control,
*P < 0.05,
**P < 0.01

Example 4.9. Effect of Cmyr-47 on Serum Total Bile Acid (TBA)

Figure 28:
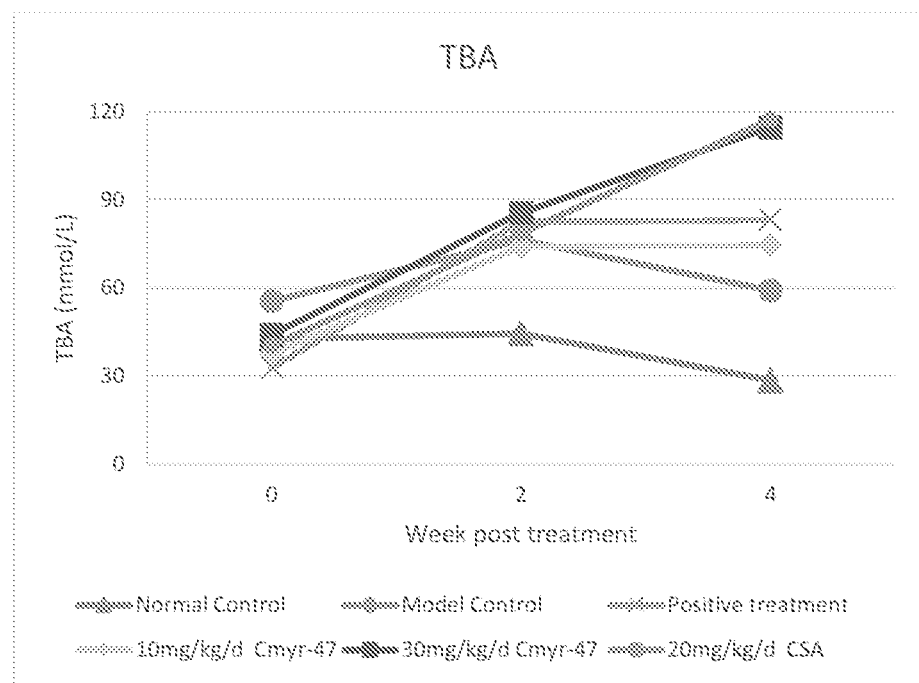
FIG. 28 shows the level of serum TBA in Zucker diabetic fatty rats after 4 weeks of Cmyr-47 treatment.

To confirm that Cmyr-47 is capable of regulating the serum TBA level, the serum TBA level of each animal was measured. As shown in Table 29 and FIG. 28, the serum TBA levels in the model controls were higher than the normal controls. As compared with the model control group, the serum TBA levels of ZDF rats treated with Cmyr-47 were further elevated in a dose-dependent fashion. Measurements at week 4 confirmed that the high dose of Cmyr-47 significantly increased the serum TBA levels (P values less than 0.05). Also, CsA significantly elevated the serum TBA levels after 4 weeks of treatment (P values less than 0.01).

TABLE 29

Effect of Cmyr-47 on Serum TBA in ZDF Rats (mmol/mL, $\bar{\chi}$ ± SEM)

| Group | Dosage/injection | TBA level after weeks of dosing | | |
|---|---|---|---|---|
| | | 0 | 2 | 4 |
| Normal control | 10 mL/kg PBS | 42.61 ± 10.94 | 44.52 ± 8.62 | 28.51 ± 8.13 |
| Model control | 10 mL/kg PBS | 55.51 ± 36.96 | 76.24 ± 31.22 | 59.15 ± 22.38# |
| Positive control | 300 mg/kg Met | 32.83 ± 12.29 | 82.48 ± 27.02 | 82.97 ± 15.82* |
| Cmyr-47Lo | 10 mg/kg Cmyr-47 | 37.51 ± 13.17 | 74.04 ± 33.35 | 74.38 ± 28.53 |
| Cray r-4 7Hi | 30 mg/kg Cmyr-47 | 44.09 ± 12.20 | 85.47 ± 24.03 | 114.58 ± 45.31* |
| CsA treatment | 20 mg/kg CsA | 40.29 ± 6.69 | 78.53 ± 7.38 | 117.35 ± 9.33** |

Note:
compared with normal control group,
P < 0.05,
P < 0.01;
compared with model control group,
*P < 0 05,
**P < 0.01

MET is a widely used antidiabetic drug that can efficiently modulate glycemia in vivo. As presented above, the efficacy of MET in glycemia regulation was also confirmed in this study. However, MET failed to provide benefits against lipid dysregulation and associated diseases, as evident by the results that MET was not capable of lowering serum TC, TG, and BUN levels, and HI values in ZDF rats. As shown in hyperlipidemic animal models, CsA treatment not only increased the serum TG and TC levels, but further increased the serum GLU levels, suggesting that effective inhibition of bile acid uptake in vitro does not always translate to a therapeutic effect on lipid and glucose metabolism in vivo. In contrast, Cmyr-47 performed well all across the tests. As demonstrated above, Cmyr-47 was capable of modulating glycemia and lipid metabolism while providing protection against pancreas damage, renal dysfunction, and cardiovascular diseases. Thus, Cmyr-47 performed superior as an anti-hyperglycemia, anti-hypercholesterolemia, anti-hyperlipidemia, and anti-adiposity agent over MET and showed a comprehensive effect on multiple diabetic phenotypes simultaneously.

The invention claimed is:

1. A method of regulating a serum lipid level and/or a blood glucose level in a subject in need thereof, comprising administering to the subject a therapeutically effective amount of a linear polypeptide or a pharmaceutical composition comprising the linear polypeptide to produce a serum concentration of the administered polypeptide at a concentration above a concentration threshold of 93 nmol/L to inhibit $Na^+$-taurocholate cotransporting polypeptide (NTCP)-mediated bile acid uptake in the subject, thereby lowering the serum lipid level and/or the blood glucose level, and/or administering to the subject a therapeutically effective amount of the linear polypeptide or a pharmaceutical composition comprising the linear polypeptide to produce a serum concentration of the administered polypeptide at or below the concentration threshold of 93 nmol/L to enhance NTCP-mediated bile acid uptake in the subject, thereby increasing the serum lipid level and/or the blood glucose level, and wherein the linear polypeptide comprises an amino acid sequence derived from Hepatitis B virus (HBV), and wherein the amino acid sequence derived from HBV is selected from SEQ ID NOs: 21-40.

2. The method of claim 1, wherein the serum lipid comprises one or more lipids chosen from cholesterol, triglycerides, and LDL-C (low density lipoproteins-cholesterol).

3. The method of claim 1, wherein the linear polypeptide further comprises at the N-terminus and/or the C-terminus a native flanking amino acid sequence from the pre-S1 region of HBV.

4. The method of claim 3, wherein the native flanking amino acid sequence from the pre-S1 region of HBV has 1-10, 1-8, 1-5, or 1-3 amino acids in length.

5. The method of claim 1, wherein the linear polypeptide comprises the glycine corresponding to amino acid residue 1 of SEQ ID NO: 23, and/or the asparagine corresponding to amino acid residue 8 of SEQ ID NO: 23.

6. The method of claim 1, wherein the linear polypeptide comprises an N-terminal modification with a hydrophobic group, and/or a C-terminal modification that is capable of stabilizing the polypeptide.

7. The method of claim 6, wherein the hydrophobic group is chosen from myristic acid, palmitic acid, stearic acid, oleic acid, linoleic acid, cholesterol, and arachidonic acid; and the C-terminal modification is amidation (amination) or isopentanediolization.

8. The method of claim 1, wherein the linear polypeptide comprises SEQ ID NO: 23, and wherein the linear polypeptide further comprises an N-terminal modification with myristic acid and a C-terminal modification with amination; or wherein the linear polypeptide comprises SEQ ID NO: 3.

9. The method of claim 1, wherein the linear polypeptide or the pharmaceutical composition comprising the linear polypeptide is administered to the subject before, concurrently with, or after the administration of a therapeutically effective amount of at least one second agent.

10. The method of claim 9, wherein the second agent is chosen from an antihyperlipidemic agent, an antihyperglycemic agent, an antidiabetic agent, an antiobesity agent, and a bile acid analogue.

11. The method of claim 10, wherein the second agent is chosen from insulin, metformin, sitagliptin, colesevelam, glipizide, simvastatin, atorvastatin, ezetimibe, fenofibrate, nicotinic acid, orlistat, lorcaserin, phentermine, topiramate, obeticholic acid, and ursodeoxycholic acid.

12. The method of claim 1, wherein the linear polypeptide or the pharmaceutical composition comprising the linear polypeptide is administered to the subject by at least one mode chosen from parenteral, intrapulmonary, intranasal, intralesional, intramuscular, intravenous, intraarterial, intraperitoneal, and subcutaneous administration.

13. The method of claim 8, wherein the administered polypeptide inhibits NTCP-mediated bile acid uptake in the subject at a serum concentration above a concentration threshold of 500 ng/ml, and/or the administered polypeptide enhances NTCP-mediated bile acid uptake in the subject at a serum concentration at or below the concentration threshold is of 500 ng/ml.

14. The method of claim 1, wherein the subject suffers from a metabolic disease that involves dysregulation of lipid metabolism and/or dysregulation of glucose metabolism.

15. The method of claim 8, wherein the subject suffers from a metabolic disease that involves dysregulation of lipid metabolism and/or dysregulation of glucose metabolism.

16. The method of claim 14, wherein the metabolic disease is diabetes.

17. The method of claim 14, wherein the metabolic disease is hyperglycemia.

18. The method of claim 15, wherein the metabolic disease is diabetes.

19. The method of claim 15, wherein the metabolic disease is hyperglycemia.

* * * * *